US007951950B2

(12) United States Patent  (10) Patent No.: US 7,951,950 B2
Little et al. (45) Date of Patent: May 31, 2011

(54) PGD2 RECEPTOR ANTAGONISTS FOR THE TREATMENT OF INFLAMMATORY DISEASES

(75) Inventors: Jeremy D. Little, Wakefield, MA (US); Shomir Ghosh, Brookline, MA (US); Sean Harrison, Belmont, MA (US); Amy M. Elder, Arlington, MA (US); Christelle C. Renou, Somerville, MA (US); Kenneth G. Carson, Princeton, NJ (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1221 days.

(21) Appl. No.: 11/360,885

(22) Filed: Feb. 23, 2006

(65) Prior Publication Data

US 2006/0241109 A1 Oct. 26, 2006

Related U.S. Application Data

(60) Provisional application No. 60/655,927, filed on Feb. 24, 2005.

(51) Int. Cl.
C07D 215/38 (2006.01)
(52) U.S. Cl. ...................................................... 546/159
(58) Field of Classification Search .................. 546/159
See application file for complete search history.

(56) References Cited

U.S. PATENT DOCUMENTS

| | | | |
|---|---|---|---|
| 5,258,510 A | 11/1993 | Ogawa et al. | |
| 6,048,873 A | 4/2000 | Vasudevan et al. | |
| 6,147,089 A | 11/2000 | DeNinno et al. | |
| 6,197,786 B1 | 3/2001 | DeNinno et al. | |
| 6,291,677 B1 | 9/2001 | Vasudevan et al. | |
| 6,310,075 B1 | 10/2001 | DeNinno et al. | |
| 6,313,107 B1 | 11/2001 | Vasudevan et al. | |
| 6,313,142 B1 | 11/2001 | Damon et al. | |
| 6,362,198 B1 | 3/2002 | Goldstein et al. | |
| 6,362,199 B1 | 3/2002 | Di Fabio | |
| 6,395,751 B1 | 5/2002 | DeNinno et al. | |
| 6,489,478 B1 | 12/2002 | DeNinno et al. | |
| 6,586,448 B1 | 7/2003 | DeNinno et al. | |
| 6,600,045 B2 | 7/2003 | Damon et al. | |
| 7,211,672 B2 | 5/2007 | Ghosh et al. | |
| 7,504,508 B2 | 3/2009 | Ghosh et al. | |
| 2002/0022218 A1 | 2/2002 | Li et al. | |

FOREIGN PATENT DOCUMENTS

| | | |
|---|---|---|
| EP | 0987251 A1 | 3/2000 |
| EP | 0992496 A1 | 4/2000 |
| EP | 1125929 A1 | 8/2001 |
| EP | 1221439 A1 | 7/2002 |
| EP | 1413306 A1 | 4/2004 |
| JP | P200253557 A | 2/2002 |
| WO | WO 9105549 | 5/1991 |
| WO | WO 9401113 | 1/1994 |
| WO | WO 0006153 A1 | 2/2000 |
| WO | WO 0017165 A1 | 3/2000 |
| WO | WO 0017166 A1 | 3/2000 |
| WO | WO 0140190 A1 | 6/2001 |
| WO | WO 0149675 A1 | 7/2001 |
| WO | WO 0158875 A2 | 8/2001 |
| WO | WO 0176629 A1 | 10/2001 |
| WO | WO 0211710 A1 | 2/2002 |
| WO | WO 0218361 A2 | 3/2002 |
| WO | WO 0222585 A1 | 3/2002 |
| WO | WO 02058652 A1 | 8/2002 |
| WO | WO 02079165 A1 | 10/2002 |
| WO | WO 02088069 A2 | 11/2002 |
| WO | WO 03097042 A1 | 11/2003 |
| WO | WO 03097598 A1 | 11/2003 |
| WO | WO 03105849 A1 | 12/2003 |
| WO | WO 2004032848 A2 | 4/2004 |
| WO | WO 2004035543 A1 | 4/2004 |
| WO | WO 2004052863 A1 | 6/2004 |
| WO | 2004/085401 * | 10/2004 |
| WO | WO 2005007094 A2 | 1/2005 |
| WO | WO 2005/100321 A1 | 10/2005 |

OTHER PUBLICATIONS

Fugi, abstract only CA 117:58764, abstract nly of JP 03239246, 1991.*
Zalukaev, L.P., et al., "Bimolecular alkylidenearylamines. XI. New data on intermolecular donor-acceptor reactions in 4-anilino-2-methyl-1,2,3,4-tetrahydroquinolines," Chemical Abstracts, Accession No. 67:53250 (1967).
Zalukaev, L.P., et al., "Bimolecular alkylidene aryl amines. X. Intramolecular donor-acceptor interaction in 2-methyl-4-anilino-1,2,3,4-tetra-hydroquinoline," Chemical Abstracts, Accession No. 65:81601 (1966).
Funabashi, Masuo, et al., "Configuration and conformation of so-called bis(alkylidenearlyamines)," Chemical Abstracts, Accession No. 72:31075 (1969).
Zalukajevs, L., "Bimolecular alkylidenearylamines. II. Structure of the products of bromination of 1-benzoyl-2-methyl-4-anilino-1,2,3,4-tetrahydroquinoline," Chemical Abstracts, Accession No. 48:56687 (1951).
Zalukajevs, L., et al., "Bimolecular alkylidenearylamines. IX. Steric structure of 2-methyl-4-anilino-1,2,3,4-tetrahydroquinolines," Chemical Abstracts, Accession No. 62:22149 (1964).
Zalukajevs, L., et al., "Bimolecular alkylidenearylamines. VIII. Synthesis and bromination of 2-methyl-4-N-acetylanilino-1,2,3,4-tetrahydroquinoline," Chemical Abstracts, Accession No. 59:54789 (1963).
International Search Report dated Jun. 7, 2006 from PCT/US06/006287, which corresponds to U.S. Appl. No. 11/360,885, 2006.

* cited by examiner

Primary Examiner — D. Margaret Seaman

(57) ABSTRACT

Disclosed are CRTH2 inhibitors represented by Structural Formula (I):

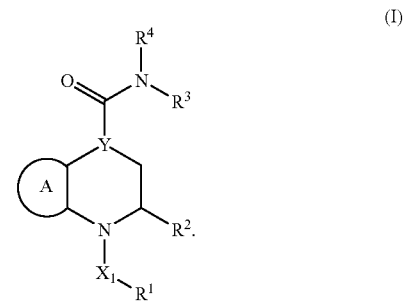

The values for the variables of Structural Formula (I) are provided herein.

39 Claims, No Drawings

PGD2 RECEPTOR ANTAGONISTS FOR THE TREATMENT OF INFLAMMATORY DISEASES

PRIORITY INFORMATION

The present application claims priority under 35 U.S.C. §119(e) to U.S. Provisional application No. 60/655,927, filed Feb. 24, 2005, entitled "PGD2 Receptor Antagonists for the Treatment of Inflammatory Diseases", the entire contents of which is hereby incorporated by reference.

BACKGROUND OF THE INVENTION

CRTH2 is a G protein-coupled chemoattractant receptor expressed on Th2 cells (Nagata et al., *J. Immunol.*, 1999, 162, 1278-1286), eosinophils, and basophils (Hirai et al., *J. Exp. Med.*, 2001, 193, 255-261). Prostaglandin D2 (PGD2) is a natural ligand for CRTH2, and is the major inflammatory mediator produced from mast cells. It has been shown that activation of CRTH2 by PGD2 induces migration and activation of Th2 cells (Hirai et al., *J. Exp. Med.* 2001, 193, 255-261; Gervais et al., *J. Allergy Clin. Immunol.* 2001, 108, 982-988) which in turn are involved in the orchestration of an allergic inflammatory response by directly or indirectly inducing migration, activation, priming and prolonged survival of effector cells, such as eosinophils and basophils (Sanz et al., *J. Immunol.* 1998, 160, 5637-5645; Pope et al., *J. Allergy Clin. Immunol.* 2001, 108, 594-601; Teran L. M., *Clin. Exp. Allergy* 1999, 29, 287-290). The role of PGD2 in the initiation and maintenance of allergic inflammation has also been demonstrated in mouse models of asthma by showing that overproduction of PGD2 in vivo by PGD2 synthase exacerbates airway inflammation (Fujitani et al., *J. Immunol.* 2002, 168, 443-449).

Accordingly, compounds which are modulators, preferably inhibitors, of the interaction between CRTH2 and PGD2 should be useful for the treatment of diseases and disorders that are mediated by CRTH2, PGD2, Th2 cells, eosinophils, and/or basophils. These diseases include but are not limited to allergic disorders, asthmatic disorders, and inflammatory disorders such as allergic rhinitis, allergic asthma, bronchoconstriction, atopic dermatitis and systemic inflammatory disorders.

It has now been found that compounds of this invention, and pharmaceutically acceptable compositions thereof, are effective as inhibitors of the interaction between CRTH2 and its natural ligand PGD2. Thus, compounds of the invention and pharmaceutical compositions thereof are useful for treating inflammatory disorders and/or disorders with an inflammatory component.

DETAILED DESCRIPTION OF THE INVENTION

This invention provides compounds that are inhibitors of CRTH2, and accordingly are useful for the treatment inflammatory disorders and/or disorders with an inflammatory component. The compounds of this invention are represented by formula I:

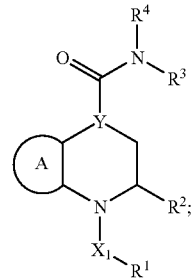

or a pharmaceutically acceptable salt thereof, wherein:

Ring A is an optionally substituted, fused 5-6 membered aryl or heteroaryl ring;

Y is >C($R^x$)— or >N—;

$X_1$ is —C(=O)—, —$SO_2$—, —CONR—, —$C(R)_2$—, or —$CO_2$—, $R^1$ is an optionally substituted group selected from an aliphatic, a monocyclic or bicyclic aryl, a monocyclic or bicyclic heteroaryl, a monocyclic or bicyclic non-aromatic heterocyclic, or a monocyclic or bicyclic non-aromatic carbocyclic group.

$R^2$ is a $C_1$-$C_3$ alkyl group, a $C_1$-$C_3$ haloalkyl group or $C_3$-$C_6$ cycloalkyl group wherein the $C_1$-$C_3$ alkyl group represented by $R^2$ is optionally substituted with $R^5$;

$R^3$ is hydrogen, $C_1$-$C_6$ alkyl optionally substituted by $R^6$, $C_1$-$C_6$ fluoroalkyl, or an optionally substituted group selected from a $C_3$-$C_8$ cycloalkyl, a monocyclic non-aromatic heterocyclic, a monocyclic aryl, or a monocyclic heteroaryl group;

$R^4$ is —[$C(R^7)_2$]$_m$—B; or $R^3$ and $R^4$ may be taken together with the intervening nitrogen atom to form an optionally substituted monocyclic or bicyclic heteroaryl or non-aromatic heterocyclic group; or $R^x$ and $R^4$ may be taken together with the intervening carbon and nitrogen atoms to form an optionally substituted monocyclic non-aromatic nitrogen-containing heterocyclic group;

$R^5$ is —OH, —O($C_{1-4}$ aliphatic), —COOR' or —N(R')$_2$;

$R^6$ is —OH, —O($C_{1-4}$ aliphatic), —N(R')$_2$, —C(O)R', —COOR', C(O)N(R')$_2$, or an optionally substituted group selected from a monocyclic cycloalkyl, a monocyclic aryl, a monocyclic heteroaryl, or a monocyclic non-aromatic heterocyclic group;

each $R^7$ is independently hydrogen, fluoro, or $C_1$-$C_3$ alkyl;

each R, $R^x$ or R' is independently hydrogen or a $C_1$-$C_4$ aliphatic group or N(R')$_2$ is a monocyclic non-aromatic nitrogen-containing heterocyclic group;

m is zero or one; and

B is —H, —$C(R^7)_3$, —$C(R^7)_2$—$C(R^7)_3$, or an optionally substituted group selected from a monocyclic or bicyclic cycloalkyl, a monocyclic or bicyclic aryl, a monocyclic or bicyclic heteroaryl, or a monocyclic or bicyclic non-aromatic heterocyclic group.

In some embodiments, compounds of the invention include compounds of formula (I) other than compounds where $X_1$ is —COO— and $R^1$ is ethyl and ring A is substituted with: a) two occurrences of OMe, b) two occurrences of Me, or c) one occurrence of $CF_3$. In some other embodiments, compounds of the invention include those compounds where $X_1$ is other than —COO—

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic", "cycloalkyl", or "cycloalkenyl"). For example, suitable aliphatic groups include substituted or unsubstituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-20, 1-15, 1-12, 1-10, 1-8, 1-6, 1-4, or 1-3 carbon atoms.

The terms "cycloaliphatic", "carbocycle", "carbocyclyl", "carbocyclo", or "carbocyclic", used alone or as part of a larger moiety, refer to a saturated or partially unsaturated cyclic aliphatic ring system having from 3 to about 14 members, wherein the aliphatic ring system is optionally substituted. In some embodiments, the cycloaliphatic group includes saturated ring systems ("cycloalkyl") having from about 3 to about 8 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic", "haloalkyl", "haloalkenyl" and "haloalkoxy" refer to an aliphatic, alkyl, alkenyl or alkoxy group, as the case may be, substituted with one or more halogen atoms. As used herein, the term "halogen" or "halo" means F, Cl, Br, or I. Unless otherwise indicated, the terms "alkyl", "alkenyl", and "alkoxy" include haloalkyl, haloalkenyl and haloalkoxy groups, including, in particular, those with 1-5 fluorine atoms. By way of example, the terms "$C_{1-3}$ aliphatic" and "$C_{1-3}$ alkyl" include within their scope trifluoromethyl and pentafluoroethyl groups.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The terms "aryl" and "ar-", used alone or as part of a larger moiety, e.g., "aralkyl", "aralkoxy", or "aryloxyalkyl", refer to a $C_6$ to $C_{14}$ aromatic moiety comprising one to three aromatic rings, which are optionally substituted. Preferably, the aryl group is a $C_{6-10}$ aryl group. Aryl groups include, without limitation, phenyl, naphthyl, and anthracenyl. The term "aryl", as used herein, also includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, unless otherwise indicated, the terms "heterocycle", "heterocyclyl", "heterocyclic radical", and "heterocyclic ring" are used interchangeably and refer to a stable 3- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or ⁺NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. In general, unless otherwise indicated, suitable substituents include those described below for a substituted aliphatic group.

A methylene unit of the alkylene chain also can be optionally replaced by a functional group. In some embodiments, an internal methylene unit is replaced with the functional group. Examples of suitable functional groups are described in the specification and claims herein.

The terms "arylene", "heterocyclene" and "carbocyclene"/ "cycloalkylene" refer to aryl, heteroaryl, non-aromatic heterocyclic or carbocyclic/cycloalkyl ring(s), respectively, in a molecule that are bonded to two other groups in the molecule through a single covalent from two of its ring atoms. Examples of suitable arylene groups include phenylene, pyrrolylene, thienylene, furanylene, imidazolylene, triazolylene, tetrazolylene, oxazolylene, isoxazolylene, oxadiazolylene, pyrazolylene, pyridinylene, pyrimidylene, pyrazinylene, thiazolylene; examples of suitable mono-cyclic carbocyclenes include cyclopropylene, cyclopentylene, cyclohexylene and cycloheptylene; and examples of suitable non-aromatic heterocyclenes include piperidinylene, piperazinylene, pyrrolidinylene, pyrazolidinylene, imidazolidinylene, tetrahydrofuranylene, tetrahydrothienylene, isooxazolidinylene, oxazolidinylene, isothiazolidinylene, thiazolidinylene, oxathiolanylene, dioxolanylene, and dithiolanylene. By way of example, the structure of 1,4-phenylene, 2,5-thienylene, 1,4 cyclohexylene and 2,5-pyrrolodinylene are shown below:

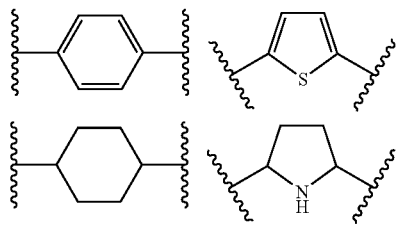

The term "substituted", as used herein, means that one or more hydrogens of the designated moiety are replaced, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

Unless otherwise indicated, an aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from halogen; —R°; —OR°; —SR°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_2$OR°; —SO$_2$N(R°)$_2$; —S(O)R°; —NR°SO$_2$N(R°)$_2$; —NR°SO$_2$R°; —N(OR°)R°; —C(=NH)—N(R°)$_2$; —P(O)$_2$R°; —PO(R°)$_2$; or —OPO(R°)$_2$; wherein each independent occurrence of R° is selected from hydrogen, or an optionally substituted group selected from C$_{1-6}$ aliphatic, aryl, heteroaryl, heterocyclic, or cycloaliphatic or, notwithstanding the definition above, two independent occurrences of R°, on the same substituent or different substituents, taken together with their intervening atom(s) form an optionally substituted 3-12 membered saturated, partially unsaturated, or fully unsaturated monocyclic or bicyclic ring having 0-4 heteroatoms independently selected from nitrogen, oxygen, or sulfur.

Unless otherwise indicated, an aliphatic or heteroaliphatic group, or a non-aromatic heterocyclic ring may contain one or more substituents and thus may be "optionally substituted". In addition to the substituents defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, or an optionally substituted group selected from $C_{1-6}$ aliphatic, aryl, heteroaryl, heterocyclic, or cycloaliphatic or, notwithstanding the definition above, two independent occurrences of R⁺, on the same substituent or different substituents, taken together with their intervening atom(s) form an optionally substituted 3-12 membered saturated, partially unsaturated, or fully unsaturated monocyclic or bicyclic ring having 0-4 heteroatoms independently selected from nitrogen, oxygen, or sulfur.

As detailed above, in some embodiments, two independent occurrences of $R^o$ (or $R^+$ or any other variable similarly defined in the specification and claims herein), are taken together with their intervening atom(s) to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of $R^o$ (or $R^+$, or any other variable similarly defined in the specification and claims herein), are taken together with their intervening atom(s) include, but are not limited to the following: a) two independent occurrences of $R^o$ (or $R^+$, or any other variable similarly defined in the specification or claims herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined in the specification or claims herein) that are bound to different atoms and are taken together with both of those atoms to form a ring, for example where a phenyl group is substituted with two occurrences of $OR^o$

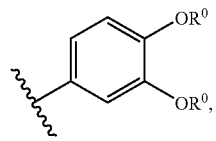

these two occurrences of $R^o$ are taken together with the oxygen atoms to which they are bound to form a fused 6-membered oxygen containing ring:

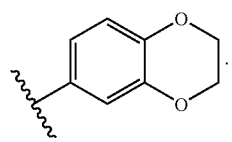

It will be appreciated that a variety of other rings (e.g., also spiro, and bridged rings) can be formed when two independent occurrences of $R^o$ (or $R^+$, or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention.

3. Description of Exemplary Compounds:

As described generally above for compounds of formula I, ring A is an optionally substituted, fused 5-6-membered aryl or heteroaryl ring. In some embodiments, ring A is an optionally substituted group selected from:

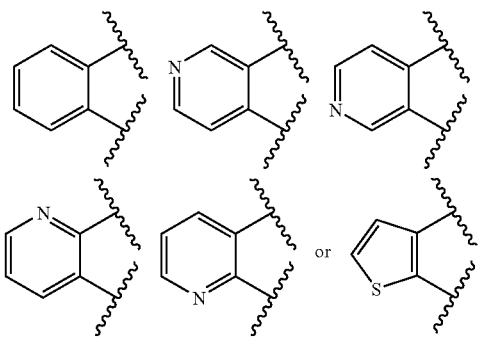

Preferably, Ring A is an optionally substituted, fused phenyl group. In general, suitable Ring A substituents are as provided in the section describing suitable aryl and heteroaryl group substituents. Preferably, Ring A, as defined generally and in preferred embodiments above, is substituted by n substituents represented by $R^8$, wherein n is 0, 1, 2, 3 or 4, preferably 0 or 1. Each $R^8$ is independently halo, —$OR^9$, —$SR^9$, —CN, —NO₂, —$N(R^{10})_2$, —$N(R^{10})C(O)R^9$, —$N(R^{10})CO_2R^{9a}$, —$N(R^{10})C(O)N(R^{10})_2$, —$C(O)N(R^{10})_2$, —$OC(O)R^9$, —$OC(O)N(R^{10})_2$, —$C(O)R^9$, —$CO_2R^9$, —$SO_2R^{9a}$, —$S(O)R^{9a}$, —$SO_2N(R^{10})_2$, —$N(R^{10})SO_2R^{9a}$ or an optionally substituted group selected from $C_{1-8}$ aliphatic, a monocyclic aryl, a monocyclic heteroaryl, or a monocyclic heterocyclic group, wherein each $R^9$ is independently hydrogen or an optionally substituted $C_{1-6}$ aliphatic group, each $R^{9a}$ is independently an optionally substituted $C_{1-6}$ aliphatic group; and each $R^{10}$ is independently hydrogen, a $C_{1-6}$ aliphatic group, —$CO_2R^{9a}$, —$SO_2R^{9a}$, or —$C(O)R^9$, or $N(R^{10})_2$ is a monocyclic heteroaryl or a monocyclic non-aromatic heterocyclic group. Preferably, each $R^8$ is independently halo, $C_{1-3}$alkyl, $C_{1-3}$haloalkyl, hydroxyl, $C_{1-3}$alkoxy, $C_{1-3}$haloalkoxy, —NO₂, —CN, amine, $C_{1-3}$alkylamine, $C_{1-3}$dialkylamine, $C_{1-3}$hydroxyalkyl or $C_{1-3}$aminoalkyl.

As described generally above for compounds of formula I, Y is >C(Rˣ)— or >N—, wherein Rˣ is hydrogen or a $C_1$-$C_4$ aliphatic group. Y is preferably >C(Rˣ)—. More preferably Y is >CH—.

As described generally above for compounds of formula I, $X_1$ is —C(=O)—, —SO₂—, —CONR—, —C(R)₂—, or —CO₂—. Preferably, $X_1$ is —C(=O)—.

As described generally above for compounds of formula I, $R^1$ is an optionally substituted group selected from an aliphatic, a monocyclic or bicyclic aryl, a monocyclic or bicyclic heteroaryl, a monocyclic or bicyclic non-aromatic heterocyclic, or a monocyclic or bicyclic non-aromatic carbocyclic group. Preferably, $R^1$ is an optionally substituted monocyclic or bicyclic aryl or heteroaryl group. In other preferred embodiments, $R^1$ is an optionally substituted group selected from phenyl, pyridyl, pyrimidyl, oxazolyl, isoxazolyl, thiazolyl, isothiazolyl, furanyl, thiophenyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl. In yet other preferred embodiments, $R^1$ is an optionally substituted monocyclic non-aromatic heterocyclic or non-aromatic carbocyclic group. In preferred embodiments, $R^1$ is an optionally substituted monocyclic non-aromatic heterocyclic or non-aromatic carbocyclic group selected from cyclopropyl, cyclobutyl, azetidinyl, cyclopentyl, pyrrolidinyl, cyclohexyl, cycloheptyl, morpholinyl, piperidinyl, piperazinyl, or thiomorpholinyl. In still other preferred embodiments, $R^1$ is optionally substituted phenyl or pyridyl. In yet other preferred embodiments, $R^1$ is optionally substituted phenyl.

In general, suitable substituents for a substitutable aromatic ring carbon or nitrogen atom of an aryl or heteroaryl group represented by $R^1$ are as provided in the section describing suitable substituents for an aryl or heteroaryl group; suitable substituents for a substitutable ring carbon or nitrogen atom of a non-aromatic heterocyclic ring in the group represented by $R^1$ are as provided in the section describing suitable substituents for a non-aromatic heterocyclic group; and suitable substituents for an aliphatic group or a substitutable ring carbon of a carbocyclic group represented by $R^1$ are as provided in the section describing suitable substituents for an aliphatic group.

In some embodiments, $R^1$ is substituted with one or more occurrences of $R^{11}$, wherein each $R^{11}$ is independently halo, $-OR^{12}$, $-SR^{12}$, $-CN$, $-NO_2$, $-N(R^{12}R^{13})$, $-N(R^{13})C(O)R^{12}$, $-N(R^{13})CO_2R^{12a}$, $-N(R^{13})C(O)N(R^{12}R^{13})$, $-C(O)N(R^{12}R^{13})$, $-OC(O)R^{12}$, $-OC(O)N(R^{12}R^{13})$, $-C(O)R^{12}$, $-CO_2R^{12}$, $-SO_2R^{12a}$, $-S(O)R^{12a}$, $-SO_2N(R^{12}R^{13})$, $-N(R^{13})SO_2R^{12a}$, or an optionally substituted group selected from $C_{1-8}$aliphatic, a monocyclic aryl, a monocyclic heteroaryl, or a monocyclic non-aromatic carbocyclic group, wherein each $R^{12}$ is independently hydrogen or an optionally substituted $C_{1-6}$ aliphatic group, each $R^{12a}$ is an optionally substituted $C_{1-6}$ aliphatic group, and each $R^{13}$ is independently hydrogen, a $C_{1-6}$ aliphatic group, $-CO_2R^{12a}$, $-SO_2R^{12a}$, or $-C(O)R^{12}$, or $-N(R^{12}R^{13})$ is an optionally substituted monocyclic heteroaryl or non-aromatic heterocyclic group. Preferably, each $R^{11}$ is independently halo, $C_{1-3}$ alkyl, $C_{1-3}$ haloalkyl, hydroxyl, $C_{1-3}$ alkoxy, $C_{1-3}$ haloalkoxy, $-NO_2$, $-CN$, amine, $C_{1-3}$ alkyl amine, $C_{1-3}$ dialkylamine, $C_{1-3}$ hydroxyalkyl or $C_{1-3}$ aminoalkyl. More preferably, $R^1$ is a phenyl, pyridyl, pyrimidyl, oxazolyl, isoxazolyl, thiazolyl, isothiazolyl, furanyl, thiophenyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each optionally substituted at any one or more substitutable ring carbon atoms with $R^{11}$. Even more preferably, $R^1$ is a phenyl group represented by the following structural formula:

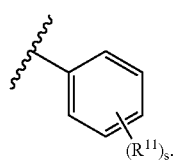

s is 0, 1, 2, 3 or 4, preferably 0-2, and more preferably 0 or 1.

Alternatively, $R^1$ is substituted with $T_2$-$V_2$-$T_3$-M-$R^Y$, and $R^1$ is further optionally substituted at any one or more substitutable ring carbon atoms with $R^{11}$.

M is absent or an optionally substituted monocyclic arylene, an optionally substituted monocyclic non-aromatic carbocyclene or an optionally substituted monocyclic non-aromatic heterocylene. Examples of suitable arylene groups include phenylene, pyrrolylene, thienylene, furanylene, imidazolylene, triazolylene, tetrazolylene, oxazolylene, isoxazolylene, oxadiazolylene, pyrazolylene, pyridinylene, pyrimidylene, pyrazinylene, thiazolylene; examples of suitable monocyclic carbocyclenes include cyclopropylene, cyclopentylene, cyclohexylene and cycloheptylene; and examples of suitable non-aromatic heterocyclenes include piperidinylene, piperazinylene, pyrrolidinylene, pyrazolidinylene, imidazolidinylene, tetrahydrofuranylene, tetrahydrothienylene, isooxazolidinylene, oxazolidinylene, isothiazolidinylene, thiazolidinylene, oxathiolanylene, dioxolanylene, and dithiolanylene. Phenylene, [2,5]thienylene and [2,5]furanylene are preferred arylene groups. Suitable substituents for an arylene are as provided in the section describing aryl and heteroaryl group substituents; and suitable substituents for non-aromatic heterocyclene and carbocyclene are as described in the sections providing suitable substituents for a non-aromatic heterocyclic group and aliphatic group, respectively. Preferred substituents for a substitutable aromatic ring carbon in a group represented by M and a substitutable ring carbon or ring nitrogen atom in a non-aromatic ring represented by M are as described above for an aryl or heteroaryl group.

$V_2$ is absent, $-O-$, $-C(O)-$, $-N(R^{19})-$, $-S-$, $-S(O)-$, $-C(O)NR^{19}-$, $-NR^{19}C(O)-$, $-S(O)_2NR^{19}-$, $-NR^{19}S(O)_2-$, or $-S(O)_2-$. Preferably, $V_2$ is absent or $-O-$.

$R^Y$ is $-C(O)OR^{18}$, $-C(O)R^{18}$, $-OC(O)R^{18}$, $-C(O)N(R^{19})_2$, $-NR^{19}C(O)R^{18}$, $-NR^{19}C(O)OR^{18a}$, $-S(O)_2R^{18a}$, $-S(O)_2COR^{18}$, $-S(O)_2N(R^{19})_2$, $-NR^{19}S(O)_2R^{18a}$, $-NR^{19}S(O)_2R^{18a}$, $S(O)_2OR^{18}$, $-S(O)OR^{18}$, $-S(O)R^{18a}$, $-SR^{18}$, $-C(O)NR^{19}S(O)_2R^{18a}$, $-CN$, $-NR^{19}C(O)N(R^{19})_2$, $-OC(O)NR^{19})_2$, $-N(R^{19})_2$, $-OR^{18}$, an optionally substituted non-aromatic heterocyclic group or an optionally substituted heteroaryl group. Suitable substituents for the non-aromatic heterocyclic group and the heteroaryl group represented by $R^Y$ are provided in the section below describing suitable substituents for a heterocyclic group and heteroaryl group, respectively. Preferably, $R^Y$ is $-C(O)OR^{18}$, $-C(O)N(R^{19})_2$, $-NR^{19}C(O)R^{18}$, $-NR^{19}C(O)OR^{18a}$, $-S(O)_2N(R^{19})_2$, $-NR^{19}S(O)_2R^{18a}$, $-NR^{19}C(O)N(R^{19})_2$, an optionally substituted non-aromatic heterocyclic group represented by $R^{20}$ or an optionally substituted heteroaryl group represented by $R^{21}$. More preferably, $R^Y$ is $-C(O)OR^{18}$, $-C(O)N(R^{19})_2$, optionally N-substituted tetrazolyl or optionally N-substituted imidazolyl.

Each $R^{18}$ is independently hydrogen or $C_{1-6}$ aliphatic group. Preferably, each $R^{18}$ is independently H or $C_1$-$C_3$ alkyl. More preferably, $R^{18}$ is $-H$, methyl, or ethyl.

Each $R^{18a}$ is independently $C_{1-6}$ aliphatic group. Preferably, each $R^{18a}$ is independently H or $C_1$-$C_3$ alkyl. More preferably, $R^{18a}$ is $-H$, methyl, or ethyl.

Each $R^{19}$ is independently selected from hydrogen, a $C_{1-6}$ aliphatic group, $-CO_2R^{18}$, $-SO_2R^{18}$, or $-C(O)R^{18}$, or $-NR^{19}$ is a monocyclic heteroaryl or a monocyclic non-aromatic heterocyclic group. Preferably, each $R^{19}$ is H or $C_1$-$C_3$ alkyl or $N(R^{19})_2$ is a nitrogen-containing non-aromatic heterocyclic group. More preferably, $R^{19}$ is $-H$, methyl, or ethyl.

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl. $R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl.

$T_2$ is absent, or a $C_{1-10}$ straight chain alkylene, and $T_3$ is a $C_{1-10}$ straight chain alkylene wherein $T_2$ and $T_3$ together contain no more than 10 carbon atoms, and provided that $T_3$ is a $C_{2-10}$ straight chained alkylene when M is absent and $V_2$ is —O—, —S—, —N($R^{19}$)—, —C(O)N($R^{19}$)— or —S(O)$_2$N($R^{19}$)— and $R^Y$ is —$NR^{19}S(O)_2R^{18a}$, —$NR^{19}S(O)_2R^{18a}$, —$NR^{19}C(O)R^{18}$, —$NR^{19}C(O)OR^{18a}$, —$NR^{19}C(O)N(R^{19})_2$, —CN, —OH, —SH, —N($R^{19}$)$_2$. $T_2$ and $T_3$ are optionally and independently substituted at any one or more substitutable carbon atoms with halide, alkyl, gem dialkyl, gem dihalo, haloalkyl, alkoxy, haloalkoxy, spiro cycloalkyl, optionally N-substituted nitrogen containing spiro non-aromatic heterocyclic group, oxygen-containing spiro non-aromatic heterocyclic group, amine, alkylamine, dialkylamine or hydroxyl. $T_2$ is preferably absent. Preferably, $T_3$ is a $C_{1-6}$ straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl.

In some embodiments, $R^1$ is a monocyclic aryl or heteroaryl group substituted with -$T_2$-$V_2$-$T_3$-M-$R^Y$ and is further optionally substituted at any one or more substitutable ring carbon atoms with $R^{11}$.

Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each substituted with —$V_2$-$T_3$-$R^Y$, and each optionally substituted at any one or more substitutable ring carbon atoms with $R^{11}$.

More preferably, $R^1$ is a phenyl group represented by the following structural formula:

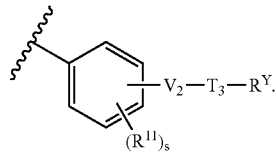

—$V_2$-$T_3$-$R^Y$ is preferably para to the $X_1$ moiety as referred to in compounds of formula I.

In another alternative, $R^1$ is substituted by —$V_3$—$R^{22}$; and is optionally further substituted at any one or more substitutable carbon atoms with $R^{11}$. $V_3$ is a covalent bond, —O—, —C(O)—, —N($R^{13}$)—, —S—, —S(O)—, —C(O)N$R^{13}$—, —$NR^{13}$C(O)—, —S(O)$_2$N$R^{13}$—, —$NR^{13}$S(O)$_2$—, or —S(O)$_2$—. Preferably, $V_3$ is a covalent bond or —O—. $R^{22}$ is an optionally substituted monocyclic or bicyclic non-aromatic carbocyclic or an optionally substituted monocyclic or bicyclic non-aromatic heterocyclic group. Preferably, $R^{22}$ is an optionally substituted moncyclic non-aromatic heterocyclic group. More preferably, $R^{22}$ is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, or piperidinyl. Even more preferably, $R^{22}$ is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl. Suitable substituents for the non-aromatic carbocyclic group and non-aromatic heterocyclic group represented by $R^{22}$ are as defined below for aliphatic and non-aromatic heterocyclic groups, respectively. Preferred substituents at a substitutable ring carbon atom of a non-aromatic carbocyclic ring or a substitutable carbon atom of a non-aromatic heterocyclic group represented by $R^{22}$ are alkyl, halide, haloalkyl, hydroxyalkyl, —C(O)O$R^{23}$, —C(O)$R^{23}$, —OC(O)$R^{23}$, or —C(O)N$R^{23}_2$. Preferred substituents at a substitutable ring nitrogen atom of a non-aromatic heterocyclic group represented by $R^{22}$ are alkyl, haloalkyl, hydroxyalkyl, —C(O)O$R^{23}$, —C(O)$R^{23}$, —(CH$_2$)$_q$CO$_2$H, —(CH$_2$)$_q$C(O)N($R^{23}$)$_2$, —(CH$_2$)$_q$CH(CH$_3$)CON($R^{23}$)$_2$; —(CH$_2$)$_q$C(CH$_3$)$_2$CON($R^{23}$)$_2$; —(CH$_2$)$_q$C(CH$_3$)$_2$CO$_2R^{23}$ or —(CH$_2$)$_q$CH(CH$_3$)CO$_2R^{23}$, wherein q is an integer from 1-4, and each $R^{23}$ is independently —H, alkyl, haloalkyl, or hydroxyalkyl.

In some embodiments, $R^1$ is a monocyclic aryl or heteroaryl group, substituted by —$V_3$—$R^{22}$; and the monocyclic aryl or heteroaryl group represented by $R^1$ optionally is further substituted at any one or more substitutable carbon atoms represented by $R^{11}$. Preferably, $R^1$ is a phenyl group represented by the following structural formula:

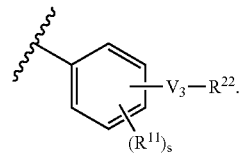

—$V_3$—$R^{22}$ is preferably para to the $X_1$ moiety as referred to in compounds of formula I.

In yet another alternative, $R^1$ is a substituted or unsubstituted aliphatic group. Preferably, $R^1$ is -$T_2$-$V_2$-$T_3$-M-$R^Y$. More preferably, $R^1$ is —$V_2$-$T_3$-$R^Y$.

As described generally above, $R^2$ is a $C_1$-$C_3$ alkyl group, a $C_1$-$C_3$ haloalkyl group or $C_3$-$C_6$ cycloalkyl group. The $C_1$-$C_3$ alkyl group represented by $R^2$ is optionally substituted with $R^5$. Preferably, $R^2$ is $C_1$-$C_2$ alkyl or $C_3$-$C_6$ cycloalkyl.

As described generally above, $R^3$ is hydrogen, $C_1$-$C_6$ alkyl optionally substituted by $R^6$, $C_1$-$C_6$ fluoroalkyl, or an optionally substituted group selected from a $C_3$-$C_8$ cycloalkyl, a monocyclic non-aromatic heterocyclic, a monocyclic aryl, or a monocyclic heteroaryl group. Suitable substituents for the monocyclic non-aromatic heterocyclic group and monocyclic aryl or heteroaryl group represented by $R^3$ are as provided in the section describing suitable substituents for an aryl or heteroaryl group and a non-aromatic heterocyclic group, respectively. Preferably, $R^3$ is a $C_1$-$C_4$ alkyl group.

As described generally above, $R^4$ is —[C($R^7$)$_2$]$_m$—B, or $R^3$ and $R^4$ may be taken together with the intervening nitrogen atom to form an optionally substituted monocyclic or bicyclic heteroaryl or non-aromatic heterocyclic group, or $R^x$ and $R^4$ may be taken together with the intervening carbon and nitrogen atoms to form an optionally substituted monocyclic non-aromatic nitrogen-containing heterocyclic group. In another alternative, $R^4$ is —(CH$_2$)$_m$—B.

$R^5$ is —OH, —O($C_{1-4}$aliphatic), —COOR' or —N(R')$_2$.

$R^6$ is —OH, —O($C_{1-4}$aliphatic), —N(R')$_2$, —C(O)R', —COOR', C(O)N(R')$_2$, or an optionally substituted group selected from a monocyclic cycloalkyl, a monocyclic aryl, a monocyclic heteroaryl, or a monocyclic non-aromatic heterocyclic group. Suitable substituents for the monocyclic cycloalkyl group, the monocyclic non-aromatic heterocyclic group, the monocyclic aryl group, and the monocyclic heteroaryl group represented by $R^6$ are as provided in the section describing suitable substituents for an aliphatic group, a non-aromatic heterocyclic group, an aryl group, and a heteroaryl group, respectively.

Each $R^7$ is independently hydrogen, fluoro, or $C_1$-$C_3$ alkyl. Preferably, $R^7$ is hydrogen or methyl, more preferably hydrogen.

Each R, $R^x$ or R' is independently hydrogen or a $C_1$-$C_4$ aliphatic group or N(R')$_2$ is a monocyclic non-aromatic nitrogen-containing heterocyclic group.

m is zero or one.

B is —H, —C($R^7$)$_3$, —C($R^7$)$_2$—C($R^7$)$_3$, an optionally substituted group selected from a monocyclic or bicyclic cycloalkyl, a monocyclic or bicyclic aryl, a monocyclic or bicyclic heteroaryl, or a monocyclic or bicyclic non-aromatic heterocyclic group. Suitable substituents for these groups are as provided in the section describing suitable substituents for the monocyclic or bicyclic cycloalkyl group, the monocyclic or bicyclic aryl group, the monocyclic or bicyclic heteroaryl group, and the monocyclic or bicyclic non-aromatic heterocyclic group. Preferred substituents for a substitutable ring carbon atom of a group represented by B is $R^{14}$. Preferably B is a monocyclic aryl or heteroaryl group or a monocyclic cycloalkyl group, each optionally substituted at any one or more substitutable ring carbon atoms with $R^{14}$. More preferably, B is a phenyl group represented by the following structural formula:

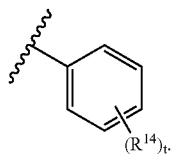

t is 0, 1, 2, 3 or 4, preferably 0-2 and more preferably 0-1.

Each $R^{14}$ is independently $C_1$-$C_4$ alkyl, $C_1$-$C_4$ haloalkyl, $C_1$-$C_4$ haloalkoxy, $R^{14a}$, $R^{14b}$, -T-$R^{14a}$, -T-$R^{14b}$, —V-$T_1$-$R^b$, —V-T-$R^{14a}$, —$V_1$-T-$R^{14a}$ or —$V_1$-$T_1$-$R^{14b}$. Preferably, each $R^{14}$ is independently, halo, $C_{1-3}$ alkyl, $C_{1-3}$ haloalkyl, hydroxyl, $C_{1-3}$ alkoxy, $C_{1-3}$haloalkoxy, —NO$_2$, —CN, amine, $C_{1-3}$ alkyl amine, $C_{1-3}$ dialkylamine, $C_{1-3}$ hydroxyalkyl or $C_{1-3}$ aminoalkyl. $R^{14}$ are independently, halo, $C_{1-3}$ alkyl, $C_{1-3}$ haloalkyl, hydroxyl, $C_{1-3}$ alkoxy, $C_{1-3}$ haloalkoxy, —NO$_2$, —CN, amine, $C_{1-3}$ alkyl amine, $C_{1-3}$ dialkylamine, $C_{1-3}$ hydroxyalkyl or $C_{1-3}$ aminoalkyl.

V is —O—, —N(R)—, —C(O)N(R)— or —S(O)$_2$N(R)—.

$V_1$ is —S(O)$_2$—, —C(O)—, —N(R)C(O)— or —N(R)SO$_2$—.

T is a $C_1$-$C_4$ optionally substituted alkylene. Examples of suitable substituents for the alkylene group represented by T include halide, alkyl, gem dialkyl, gem dihalo, haloalkyl, alkoxy, haloalkoxy, spiro cycloalkyl, optionally N-substituted nitrogen containing spiro non-aromatic heterocyclic group, oxygen-containing spiro non-aromatic heterocyclic group, amine, alkylamine, dialkylamine or hydroxyl.

$T_1$ is a $C_2$-$C_4$ optionally substituted alkylene. Examples of suitable substituents for the alkylene group represented by $T_1$ include halide, alkyl, gem dialkyl, gem dihalo, haloalkyl, alkoxy, haloalkoxy, spiro cycloalkyl, optionally N-substituted nitrogen containing spiro non-aromatic heterocyclic group, oxygen-containing spiro non-aromatic heterocyclic group, amine, alkylamine, dialkylamine or hydroxyl.

Each $R^{14a}$ is independently selected from —OR$^{15a}$, —SR$^{15a}$, —C(O)N(R$^{16}$)$_2$, —C(O)R$^{15}$, —CO$_2$R$^{15}$, —SO$_2$R$^{15a}$, —S(O)R$^{15a}$, —SO$_2$N(R$^{16}$)$_2$, an optionally substituted monocyclic aryl or heteroaryl group, or an optionally substituted monocyclic non-aromatic heterocyclic group. Suitable substituents for the monocyclic aryl or heteroaryl group and the monocyclic non-aromatic heterocyclic group represented by $R^{14a}$ are as provided in the section below describing suitable substituents for an aryl, heteroaryl, and a non-aromatic heterocyclic group, respectively.

Each $R^{14b}$ is independently selected from halo, —OH, —SH, —CN, —NO$_2$, —N(R$^{16}$)$_2$, —N(R$^{16}$)C(O)R$^{15}$, —N(R$^{16}$)CO$_2$R$^{15a}$, —N(R$^{16}$)C(O)N(R$^{16}$)$_2$, —OC(O)R$^{15}$, —OC(O)N(R$^{16}$)$_2$ or —N(R$^{16}$)SO$_2$R$^{15a}$.

Each $R^{15}$ is independently hydrogen or a $C_{1-6}$ aliphatic group.

Each $R^{15a}$ is a $C_{1-6}$ aliphatic group.

Each $R^{16}$ is independently selected from hydrogen, a $C_{1-6}$aliphatic group, —CO$_2$R$^{15a}$, —SO$_2$R$^{15a}$, or —C(O)R$^{15}$, or N(R$^{16}$)$_2$ is a monocyclic heteroaryl or a monocyclic non-aromatic heterocyclic group.

In a preferred embodiment, for compounds of formula (I), $R^1$ is an optionally substituted group selected from a monocyclic or bicyclic aryl, a monocyclic or bicyclic heteroaryl, a monocyclic or bicyclic non-aromatic heterocyclic, or a monocyclic or bicyclic non-aromatic carbocyclic group, and Y is >C($R^x$)—.

In another preferred embodiment, a compound of the invention is represented by Structural Formula (II) or (III):

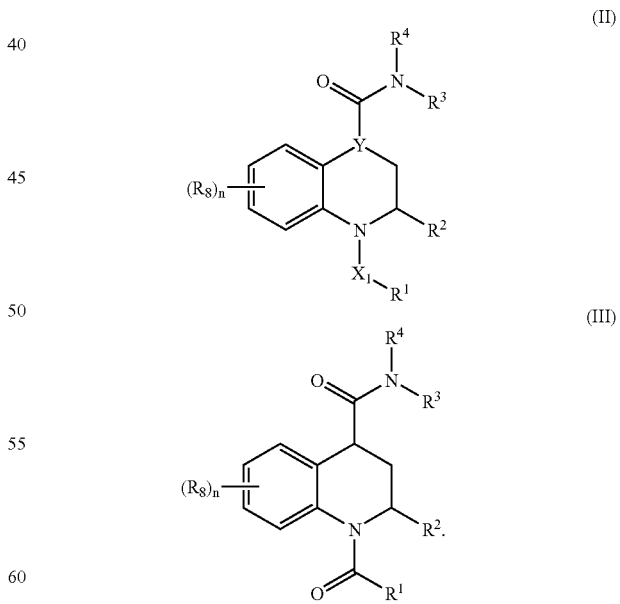

The values and preferred values for the variables in Structural Formulas (II) and (III) are as described above for Structural Formula (I). Preferably in Structural Formula (II), $R^1$ is an optionally substituted group selected from a monocyclic or bicyclic aryl, a monocyclic or bicyclic heteroaryl, a monocyclic or bicyclic non-aromatic heterocyclic, or a monocyclic or bicyclic non-aromatic carbocyclic group, and Y is >C($R^x$)—. Preferably in Structural Formula (III), $R^1$ is an optionally substituted group selected from a monocyclic or bicyclic aryl, a monocyclic or bicyclic heteroaryl, a monocyclic or bicyclic non-aromatic heterocyclic, or a monocyclic or bicyclic non-aromatic carbocyclic group.

It will be appreciated that certain other embodiments are of interest:

In a first preferred embodiment, a compound of the invention is represented by Structural Formulas (II) and (III), wherein:

$R^1$ is a monocyclic or bicyclic aryl or heteroaryl group optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each optionally substituted at any one or more substitutable ring carbon atoms with $R^{11}$; and the values and preferred values for $R^{11}$ and the remainder of the variables in Structural Formulas (II) and (III) are as described above for Structural Fomula (I).

In a second preferred embodiment, a compound of the invention is represented by Structural Formulas (II) and (III), wherein:

$R^1$ is an optionally substituted monocyclic or bicyclic aryl or heteroaryl group optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each optionally substituted at any one or more substitutable ring carbon atoms with $R^{11}$;

B is a monocyclic aryl or heteroaryl group or a monocyclic cycloalkyl group, each optionally substituted at any one or more substitutable ring carbon atoms with $R^{14}$; and the values and preferred values for $R^{11}$, $R^{14}$, and the remainder of the variables in Structural Formulas (II) and (III) are as described above for Structural Formula (I).

In a third preferred embodiment, a compound of the invention is represented by Structural Formulas (II) and (III), wherein:

$R^1$ is an optionally substituted monocyclic or bicyclic aryl or heteroaryl group optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each optionally substituted at any one or more substitutable ring carbon atoms with $R^{11}$;

$R^2$ is $C_1$-$C_2$ alkyl or $C_3$-$C_6$ cycloalkyl;

$R^3$ is a $C_1$-$C_4$ alkyl group;

$R^4$ is —$(CH_2)_m$—B;

B is a monocyclic aryl or heteroaryl group or a monocyclic cycloalkyl group, each optionally substituted at any one or more substitutable ring carbon atoms with $R^{14}$; and the values and preferred values for m, $R^{11}$, $R^{14}$ and the remainder of the variables in Structural Formulas (II) and (III) are as described above for Structural Formula (I).

In a fourth preferred embodiment, a compound of the invention is represented by Structural Formula (II) or (III) wherein:

$R^1$ is a monocyclic or bicyclic aryl or heteroaryl group substituted with -$T_2$-$V_2$-$T_3$-M-$R^Y$ and further optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each substituted with -$T_2$-$V_2$-$T_3$-M-$R^Y$, and each optionally substituted at any one or more substitutable ring carbon atoms with $R^{11}$; and the values and preferred values for $R^Y$, M, $V_2$, $T_2$, $T_3$, $R^{11}$ and the remainder of the variables in Structural Formulas (II) and (III) are as described for Structural Formula (I). M and $T_2$ are preferably absent.

In a fifth preferred, a compound of the invention is represented by Structural Formula (II) or (III), wherein:

$R^1$ is a monocyclic or bicyclic aryl or heteroaryl group substituted with -$T_2$-$V_2$-$T_3$-M-$R^Y$ and further optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each substituted with -$T_2$-$V_2$-$T_3$-M-$R^Y$, and each optionally substituted at any one or more substitutable ring carbon atoms with $R^{11}$;

B is a monocyclic aryl or heteroaryl group or a monocyclic cycloalkyl group, each optionally substituted at any one or more substitutable ring carbon atoms with $R^{14}$; and the values and preferred values for $R^Y$, M, $V_2$, $T_2$, $T_3$, $R^{11}$, $R^{14}$ and the remainder of the variables in Structural Formulas (II) and (III) are as described for Structural Formula (I). M and $T_2$ are preferably absent.

In a sixth preferred, a compound of the invention is represented by Structural Formula (II) or (III), wherein:

$R^1$ is a monocyclic or bicyclic aryl or heteroaryl group substituted with -$T_2$-$V_2$-$T_3$-M-$R^Y$ and further optionally substituted at any one or more substitutable ring carbon atoms with $R^{11}$. Preferably, $R^1$ is a phenyl, pyridyl, pyrimidyl, oxazolyl, isoxazolyl, thiazolyl, isothiazolyl, furanyl, thiophienyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each substituted with -$T_2$-$V_2$-$T_3$-M-$R^Y$, and each optionally substituted at any one or more substitutable ring carbon atoms with $R^{11}$;

$R^2$ is $C_1$-$C_2$ alkyl or $C_3$-$C_6$ cycloalkyl;

$R^3$ is a $C_1$-$C_4$ alkyl group;

$R^4$ is —$(CH_2)_m$—B;

B is a monocyclic aryl or heteroaryl group or a monocyclic cycloalkyl group, each optionally substituted at any one or more substitutable ring carbon atoms with $R^{14}$; and the values and preferred values for m, $R^Y$, M, $V_2$, $T_2$, $T_3$, $R^{11}$, $R^{14}$ and the remainder of the variables in Structural Formulas (II) and (III) are as described for Structural Formula (I). M and $T_2$ are preferably absent.

In a seventh preferred embodiment, a compound of the invention is represented by Structural Formula (II) or (III), wherein:

R$^1$ is a monocyclic aryl or heteroaryl group, substituted by —V$_3$—R$^{22}$. The aryl or heteroaryl group represented by R$^1$ optionally is further substituted at any one or more substitutable carbon atoms represented by R$^{11}$;

the values and preferred values for V$_3$, R$^{11}$, R$^{22}$ and the remainder of the variables in Structural Formulas (II) and (III) are as described for Structural Formula (I).

In an eighth preferred embodiment, a compound of the invention is represented by Structural Formula (II) or (III), wherein:

R$^1$ is a monocyclic aryl or heteroaryl group, substituted by —V$_3$—R$^{22}$. The aryl or heteroaryl group represented by R$^1$ optionally is further substituted at any one or more substitutable carbon atoms represented by R$^{11}$;

B is a monocyclic aryl or heteroaryl group or a monocyclic cycloalkyl group, each optionally substituted at any one or more substitutable ring carbon atoms with R$^{14}$; and the values and preferred values for V$_3$, R$^{11}$, R$^{14}$, R$^{22}$ and the remainder of the variables in Structural Formulas (II) and (III) are as described for Structural Formula (I).

In a ninth preferred embodiment, a compound of the invention is represented by Structural Formula (II) or (III), wherein:

R$^1$ is a monocyclic aryl or heteroaryl group, substituted by —V$_3$—R$^{22}$. The aryl or heteroaryl group represented by R$^1$ optionally is further substituted at any one or more substitutable carbon atoms represented by R$^{11}$;

R$^2$ is C$_1$-C$_2$ alkyl or C$_3$-C$_6$ cycloalkyl;

R$^3$ is a C$_1$-C$_4$ alkyl group;

R$^4$ is —(CH$_2$)$_m$—B;

B is a monocyclic aryl or heteroaryl group or a monocyclic cycloalkyl group, each optionally substituted at any one or more substitutable ring carbon atoms with R$^{14}$; and the values and preferred values for m, V$_3$, R$^{11}$, R$^{14}$, R$^{22}$ and the remainder of the variables in Structural Formulas (II) and (III) are as described for Structural Formula (I).

In a tenth preferred embodiment, a compound of the invention is represented by Structural Formula (II) or (III), wherein:

R$^1$ is a monocyclic aryl or heteroaryl group, substituted by —V$_3$—R$^{22}$. The aryl or heteroaryl group represented by R$^1$ optionally is further substituted at any one or more substitutable carbon atoms represented by R$^{11}$;

R$^2$ is C$_1$-C$_2$ alkyl or C$_3$-C$_6$ cycloalkyl;

R$^3$ is a C$_1$-C$_4$ alkyl group;

R$^4$ is —(CH$_2$)$_m$—B;

R$^{22}$ is an optionally substituted monocyclic non-aromatic heterocyclic group;

B is a monocyclic aryl or heteroaryl group or a monocyclic cycloalkyl group, each optionally substituted at any one or more substitutable ring carbon atoms with R$^{14}$; and the values and preferred values for m, V$_3$, R$^{11}$, R$^{14}$ and the remainder of the variables in Structural Formulas (II) and (III) are as described for Structural Formula (I).

In the first through the tenth preferred embodiments described directly above, Y in Structural Formula (II) is preferably >C(R$^x$)—.

In yet another preferred embodiment, a compound of the present invention is represented by Structural Formula (IV):

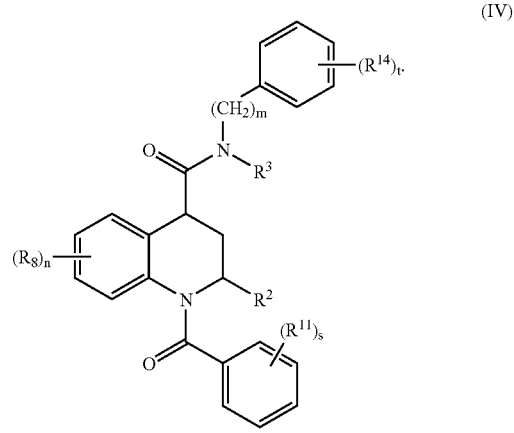

(IV)

The values and preferred values for the variables in Structural Formula (IV) are as described above for Structural Formula (I).

In an eleventh preferred embodiment, a compound of the present invention is represented by Structural Formula (IV), wherein:

R$^2$ is C$_1$-C$_2$ alkyl or C$_3$-C$_6$ cycloalkyl;

R$^3$ is a C$_1$-C$_4$ alkyl group; and the values and preferred values for the remainder of the variables in Structural Formula (IV) are as described above for Structural Formula (I).

In still another preferred embodiment, a compound of the present invention is represented by Structural Formula (V) or (VI):

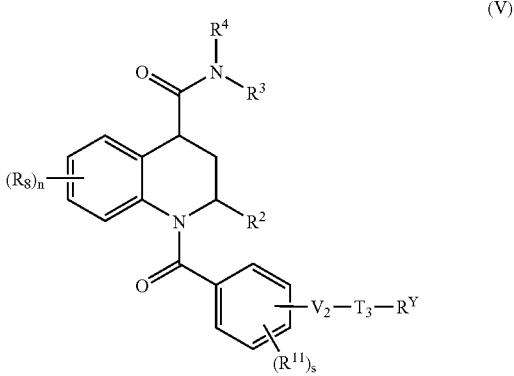

(V)

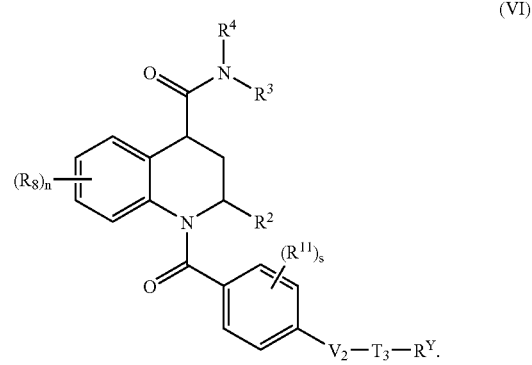

(VI)

The values and preferred values for the variables in Structural Formulas (V) and (VI) are as described above for Structural Formula (I).

In a twelfth preferred embodiment, a compound of the present invention is represented by Structural Formula (V) or (VI), wherein $R^2$ is $C_1$-$C_2$ alkyl or $C_3$-$C_6$ cycloalkyl; $R^3$ is a $C_1$-$C_4$ alkyl group; $R^4$ is —$(CH_2)_m$—B; B is a monocyclic aryl or heteroaryl group or a monocyclic cycloalkyl group, each optionally substituted at any one or more substitutable ring carbon atoms with $R^{14}$; and the values and preferred values for m, $R^{14}$ and the remainder of the variables in Structural Formula (V) and (VI) are as described above for Structural Formula (I).

In a thirteenth preferred embodiment, a compound of the present invention is represented by Structural Formula (V) or (VI), wherein:

$R^2$ is $C_1$-$C_2$ alkyl or $C_3$-$C_6$ cycloalkyl;

$R^3$ is a $C_1$-$C_4$ alkyl group;

$R^4$ is —$(CH_2)_m$—B;

B is a monocyclic aryl or heteroaryl group or a monocyclic cycloalkyl group, each optionally substituted at any one or more substitutable ring carbon atoms with $R^{14}$;

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;

$R^Y$ is —$C(O)OR^{18}$, —$C(O)N(R^{19})_2$, —$NR^{19}C(O)R^{18}$, —$NR^{19}C(O)OR^{18a}$, —$(O)_2N(R^9)_2$, —$NR^{19}S(O)_2R^{18a}$, —$NR^{19}C(O)N(R^{19})_2$, an optionally substituted non-aromatic heterocyclic group represented by $R^{20}$ or an optionally substituted heteroaryl group represented by $R^{21}$. Preferably, $R^Y$ is —$C(O)OR^{18}$, —$C(O)N(R^{19})_2$, an optionally N-substituted tetrazolyl or an optionally N-substituted imidazolyl;

each $R^{18}$ is independently H or $C_1$-$C_3$ alkyl. Preferably, each $R^{18}$ is independently —H, methyl or ethyl;

each $R^{18a}$ is independently $C_1$-$C_3$ alkyl. Preferably, each $R^{18}$ is independently methyl or ethyl;

each $R^{19}$ is H or alkyl or $NR^{19}_2$ is a nitrogen-containing non-aromatic heterocyclic group. Preferably, each $R^{19}$ is independently —H, methyl or ethyl;

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl;

$R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl; and the values and preferred values for m, $R^{14}$ and the remainder of the variables in Structural Formula (V) and (VI) are as described above for Structural Formula (I).

In still another preferred embodiment, a compound of the present invention is represented by Structural Formula (VII):

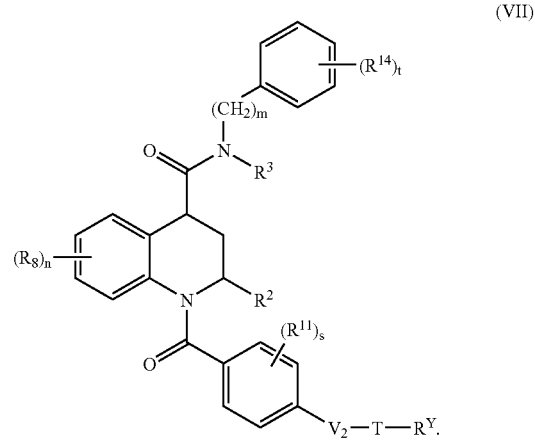

(VII)

The values and preferred values for the variables in Structural Formula (VII) are as described above for Structural Formula (I).

In a fourteenth preferred embodiment, a compound of the present invention is represented by Structural Formula (VII):

$R^2$ is $C_1$-$C_2$ alkyl or $C_3$-$C_6$ cycloalkyl;

$R^3$ is a $C_1$-$C_4$ alkyl group;

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;

$R^Y$ is —$C(O)OR^{18}$, —$C(O)N(R^{19})_2$, —$NR^{19}C(O)R^{18}$, —$NR^{19}C(O)OR^{18a}$, —$S(O)_2N(R^{19})_2$, —$NR^{19}S(O)_2R^{18a}$, —$NR^{19}C(O)N(R^{19})_2$, an optionally substituted non-aromatic heterocyclic group represented by $R^{20}$ or an optionally substituted heteroaryl group represented by $R^{21}$. Preferably, $R^Y$ is —$C(O)OR^{18}$, —$C(O)N(R^{19})_2$, an optionally N-substituted tetrazolyl or an optionally N-substituted imidazolyl;

each $R^{18}$ is independently H or $C_1$-$C_3$ alkyl. Preferably, each $R^{18}$ is independently —H, methyl or ethyl;

each $R^{18a}$ is independently $C_1$-$C_3$ alkyl. Preferably, each $R^{18}$ is independently methyl or ethyl;

each $R^{19}$ is H or alkyl or $N(R^{19})_2$ is a nitrogen-containing non-aromatic heterocyclic group. Preferably, each $R^{19}$ is independently —H, methyl or ethyl;

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl;

$R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl; and the values and preferred values for the remainder of the variables in Structural Formula (V) and (VI) are as described above for Structural Formula (I).

In a fifteenth preferred embodiment, a compound of the present invention is represented by Structural Formula (VII):

$R^2$ is $C_1$-$C_2$ alkyl or $C_3$-$C_6$ cycloalkyl;

$R^3$ is a $C_1$-$C_4$ alkyl group;

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;

$R^Y$ is —C(O)OR$^{18}$, —C(O)N(R$^{19}$)$_2$, optionally N-substituted tetrazolyl or optionally N-substituted imidazolyl;

$R^{18}$ and each $R^{19}$ are independently —H, methyl, or ethyl; and the values and preferred values for the remainder of the variables in Structural Formula (V) and (VI) are as described above for Structural Formula (I).

In another preferred embodiment, a compound of the present invention is represented by Structural Formula (VIII) or (IX):

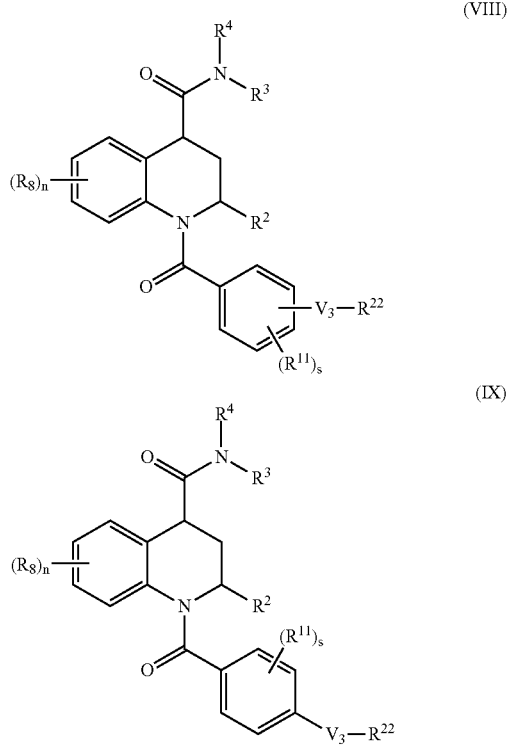

The values and preferred values for the variables in Structural Formula (VIII) and (IX) are as described above for Structural Formula (I).

In a sixteenth preferred embodiment, a compound of the present invention is represented by Structural Formula (VIII) or (IX) wherein: $R^2$ is $C_1$-$C_2$ alkyl or $C_3$-$C_6$ cycloalkyl; $R^3$ is a $C_1$-$C_4$ alkyl group; $R^4$ is —(CH$_2$)$_m$—B; $R^{22}$ is an optionally substituted monocyclic non-aromatic heterocyclic group; B is a monocyclic aryl or heteroaryl group or a monocyclic cycloalkyl group, each optionally substituted at any one or more substitutable ring carbon atoms with $R^{14}$; and the values and preferred values for m, $R^{14}$ and the remainder of the variables in Structural Formulas (VIII) and (IX) are as described for Structural Formula (I).

In a seventeenth preferred embodiment, a compound of the present invention is represented by Structural Formula (VIII) or (IX), wherein:

$R^2$ is $C_1$-$C_2$ alkyl or $C_3$-$C_6$ cycloalkyl;

$R^3$ is a $C_1$-$C_4$ alkyl group;

$R^4$ is —(CH$_2$)$_m$—B;

B is a monocyclic aryl or heteroaryl group or a monocyclic cycloalkyl group, each optionally substituted at any one or more substitutable ring carbon atoms with $R^{14}$;

$R^{22}$ is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, or piperidinyl. Preferably, $R^{22}$ is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl, each optionally substituted at any substitutable carbon atom by alkyl, halide, haloalkyl, hydroxyalkyl, —C(O)OR$^{23}$, —C(O)R$^{23}$, —OC(O)R$^{23}$, or —C(O)N(R$^{23}$)$_2$, and each optionally substituted at any substitutable nitrogen atom with alkyl, haloalkyl, hydroxyalkyl, —C(O)OR$^{23}$, —C(O)R$^{23}$, —(CH$_2$)$_q$CO$_2$H, —(CH$_2$)$_q$C(O)N(R$^{23}$)$_2$, —(CH$_2$)$_q$CH(CH$_3$)CON(R$^{23}$)$_2$; —(CH$_2$)$_q$C(CH$_3$)$_2$CON(R$^{23}$)$_2$; —(CH$_2$)$_q$C(CH$_3$)$_2$CO$_2$R$^{23}$ or —(CH$_2$)$_q$CH(CH$_3$)CO$_2$R$^{23}$; and the values and preferred values for m, q, $R^{14}$, $R^{23}$ and the remainder of the variables in Structural Formulas (VIII) and (IX) are as described for Structural Formula (I).

In an eighteenth preferred embodiment, a compound of the present invention is represented by Structural Formula (VIII) or (IX), wherein:

V is absent or —O—;

$R^2$ is $C_1$-$C_2$ alkyl or $C_3$-$C_6$ cycloalkyl;

$R^3$ is a $C_1$-$C_4$ alkyl group;

$R^4$ is —(CH$_2$)$_m$—B;

B is a monocyclic aryl or heteroaryl group or a monocyclic cycloalkyl group, each optionally substituted at any one or more substitutable ring carbon atoms with $R^{14}$;

$R^{22}$ is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, or piperidinyl. Preferably, $R^{22}$ is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl, each optionally substituted at any substitutable carbon atom by alkyl, halide, haloalkyl, hydroxyalkyl, —C(O)OR$^{23}$, —C(O)R$^{23}$, —OC(O)R$^{23}$, or —C(O)N(R$^{23}$)$_2$, and each optionally substituted at any substitutable nitrogen atom with alkyl, haloalkyl, hydroxyalkyl, —C(O)OR$^{23}$, —C(O)R$^{23}$, —(CH$_2$)$_q$CO$_2$H, —(CH$_2$)$_q$C(O)N(R$^{23}$)$_2$, —(CH$_2$)$_q$CH(CH$_3$)CON(R$^{23}$)$_2$; —(CH$_2$)$_q$C(CH$_3$)$_2$CON(R$^{23}$)$_2$; —(CH$_2$)$_q$C(CH$_3$)$_2$CO$_2$R$^{23}$ or —(CH$_2$)$_q$CH(CH$_3$)CO$_2$R$^{23}$; and the values and preferred values for m, q, $R^{14}$, $R^{23}$ and the remainder of the variables in Structural Formulas (VIII) and (IX) are as described for Structural Formula (I).

In certain preferred embodiments $V_3$ is absent.

In another preferred embodiment, a compound of the present invention is represented by Structural Formula (X):

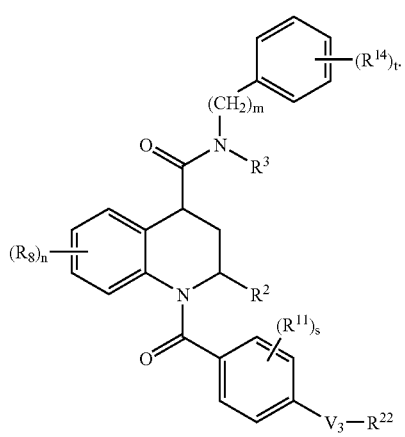

(X)

wherein the values and preferred values for the variables in Structural Formula (X) are as described for Structural Formula (I). In certain preferred embodiments $V_3$ is absent.

In a nineteenth preferred embodiment, a compound of the present invention is represented by Structural Formula (X) wherein:

V is absent or —O—;

$R^2$ is $C_1$-$C_2$ alkyl or $C_3$-$C_6$ cycloalkyl; $R^3$ is a $C_1$-$C_4$ alkyl group; $R^{22}$ is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl, each optionally substituted at any substitutable carbon atom by alkyl, halide, haloalkyl, hydroxyalkyl, —C(O)OR$^{23}$, —C(O)R$^{23}$, —OC(O)R$^{23}$, or —C(O)N(R$^{23}$)$_2$, and each optionally substituted at any substitutable nitrogen atom with alkyl, haloalkyl, hydroxyalkyl, —C(O)OR$^{23}$, —C(O)R$^{23}$, —(CH$_2$)$_q$CO$_2$H, —(CH$_2$)$_q$C(O)N(R$^{23}$)$_2$, —(CH$_2$)$_q$CH(CH$_3$)CON(R$^{23}$)$_2$; —(CH$_2$)$_q$C(CH$_3$)$_2$CON(R$^{23}$)$_2$; —(CH$_2$)$_q$C(CH$_3$)$_2$CO$_2$R$^{23}$ or —(CH$_2$)$_q$CH(CH$_3$)CO$_2$R$^{23}$; and the values and preferred values for m, q, $R^{14}$, $R^{23}$ and the remainder of the variables in Structural Formulas (X) are as described for Structural Formula (I).

In still another preferred embodiment, a compound of the present invention is represented by Structural Formula (XI):

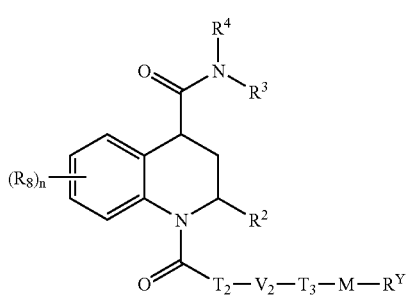

(XI)

wherein the values and preferred values for the variables in Structural Formula (XI) are as described for Structural Formula (I).

In another preferred embodiment, a compound of the present invention is represented by Structural Formula (XII):

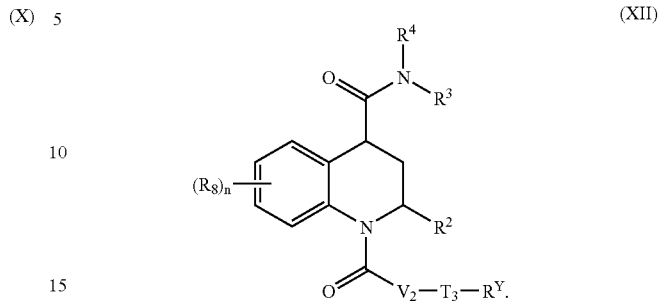

(XII)

wherein the values and preferred values for the variables in Structural Formula (XII) are as described for Structural Formula (I).

In a twentieth preferred embodiment, a compound of the present invention is represented by Structural Formula (XII), wherein:

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;

$R^Y$ is —C(O)OR$^{18}$, —C(O)N(R$^{19}$)$_2$, —NR$^{19}$C(O)R$^{18}$, —NR$^{19}$C(O)OR$^{18a}$, —S(O)$_2$N(R$^{19}$)$_2$, —NR$^{19}$S(O)$_2$R$^{18a}$, —NR$^{19}$C(O)N(R$^{19}$)$_2$, an optionally substituted non-aromatic heterocyclic group represented by $R^{20}$ or an optionally substituted heteroaryl group represented by $R^{21}$;

each $R^{18}$ is independently H or $C_1$-$C_3$ alkyl;
each $R^{18a}$ is independently $C_1$-$C_3$ alkyl;
each $R^{19}$ is H or alkyl or N(R$^{19}$)$_2$ is a nitrogen-containing non-aromatic heterocyclic group;

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl; and $R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl;

and the values and preferred values for the remainder of the variables in Structural Formula (XII) are as described for Structural Formula (I).

In a twenty-first preferred embodiment, a compound of the present invention is represented by Structural Formula (XII), wherein:

B is a monocyclic aryl or heteroaryl group or a monocyclic cycloalkyl group, each optionally substituted at any one or more substitutable ring carbon atoms with $R^{14}$;

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl $R^Y$ is —C(O)OR$^{18}$, —C(O)N(R$^{19}$)$_2$, —NR$^{19}$C(O)R$^{18}$, —NR$^{19}$C(O)OR$^{18a}$, —S(O)$_2$N(R$^{19}$)$_2$, —NR$^{19}$S(O)$_2$R$^{18a}$, —NR$^{19}$C(O)N(R$^{19}$)$_2$, an optionally substituted non-aromatic heterocyclic group represented by $R^{20}$ or an optionally substituted heteroaryl group represented by $R^{21}$. Preferably, $R^Y$ is —C(O)OR$^{18}$, —C(O)N(R$^{19}$)$_2$, optionally N-substituted tetrazolyl or optionally N-substituted imidazolyl;

each $R^{18}$ is independently H or $C_1$-$C_3$ alkyl. Preferably, each $R^{18}$ is independently —H, methyl, or ethyl;

each $R^{18a}$ is independently $C_1$-$C_3$ alkyl. Preferably, each $R^{18}$ is independently methyl, or ethyl;

each $R^{19}$ is H or alkyl or N(R$^{19}$)$_2$ is a nitrogen-containing non-aromatic heterocyclic group. Preferably, each $R^{19}$ is independently —H, methyl, or ethyl;

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl; and $R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl; and and the values and preferred values for $R^{14}$ and the remainder of the variables in Structural Formulas (XII) are as described for Structural Formula (I).

In another preferred embodiment, a compound of the present invention is represented by Structural Formula (XIII):

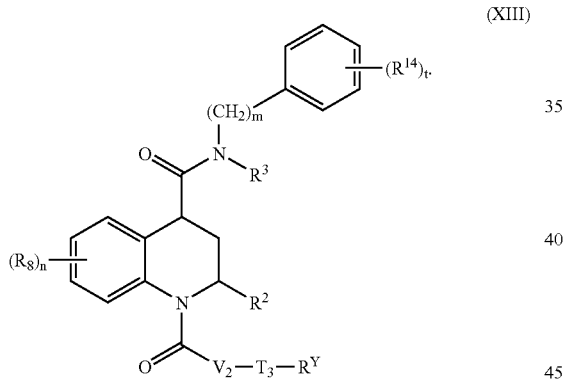

(XIII)

wherein $V_2$, $T_3$, $R^Y$, $R^{18}$, $R^{18a}$ and $R^{19}$ are as described for Structural Formula (XII). The values and preferred values for the remainder of the variables in Structural Formula (XIII) are as described for Structural Formula (I). Preferably, $R^Y$ is —C(O)OR$^{18}$, —C(O)N(R$^{19}$)$_2$, optionally N-substituted tetrazolyl or optionally N-substituted imidazolyl; and $R^{18}$ and each $R^{19}$ are independently —H, methyl, or ethyl.

More preferably in Structural Formulas (I)-(XIII), $R^8$, $R^{11}$ and $R^{14}$ are independently, halo, $C_{1-3}$ alkyl, $C_{1-3}$ haloalkyl, hydroxyl, $C_{1-3}$ alkoxy, $C_{1-3}$ haloalkoxy, —NO$_2$, —CN, amine, $C_{1-3}$ alkyl amine, $C_{1-3}$ dialkylamine, $C_{1-3}$ hydroxyalkyl or $C_{1-3}$ aminoalkyl.

More preferably in Structural Formulas (IIII)-(XIII), $R^2$ and C(O)NR$^3$R$^4$ are trans. In Structural Formulas (I) and (II), $R^2$ and C(O)NR$^3$R$^4$ are preferably trans when Y is >C(R$^x$)—.

Table 1 below depicts certain exemplary compounds of formula I.

TABLE 1

Examples of formula I compounds

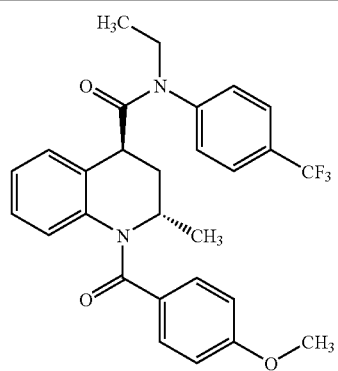

1

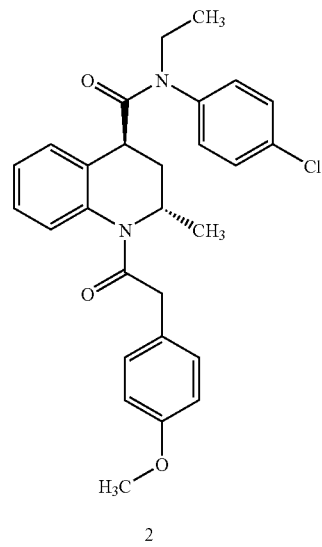

2

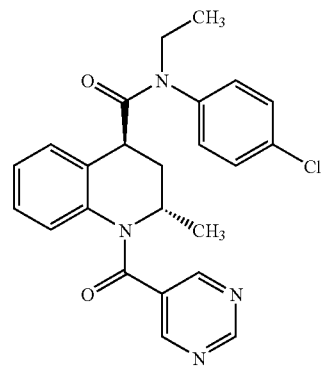

3

TABLE 1-continued
Examples of formula I compounds
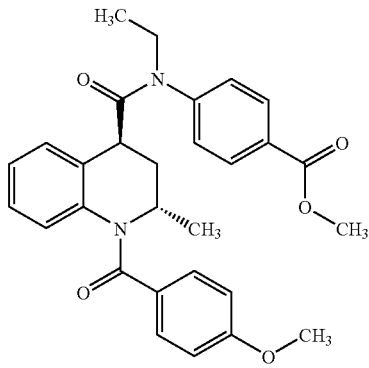
4
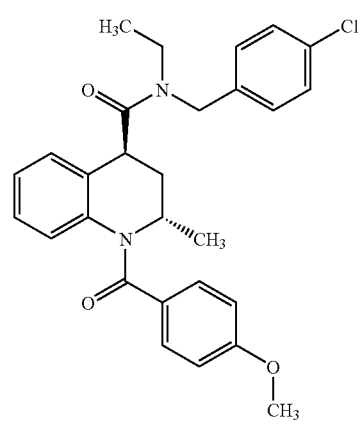
5
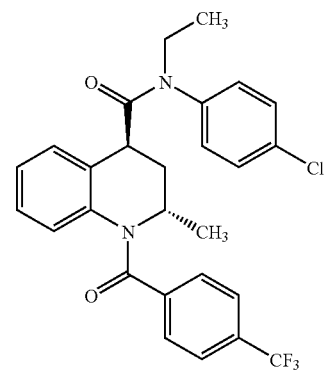
6
TABLE 1-continued
Examples of formula I compounds
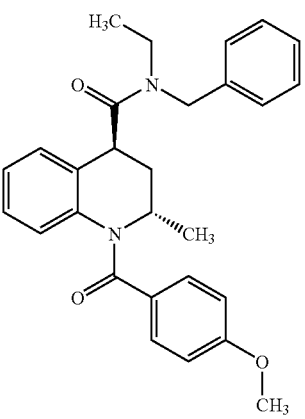
7
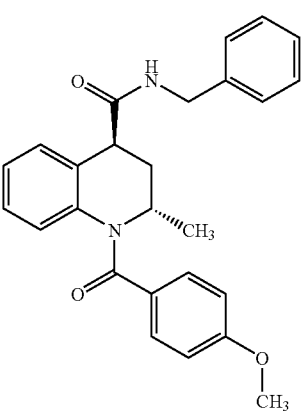
8
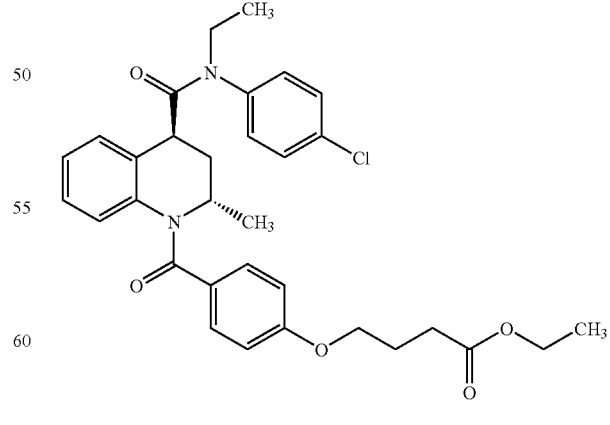
9

TABLE 1-continued
Examples of formula I compounds
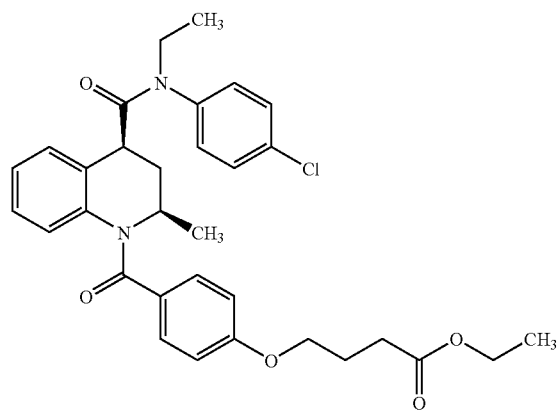
10
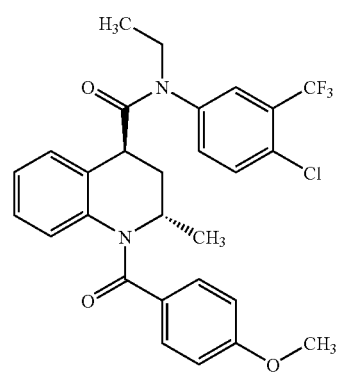
11
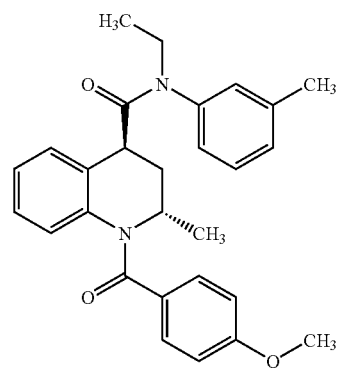
12
TABLE 1-continued
Examples of formula I compounds
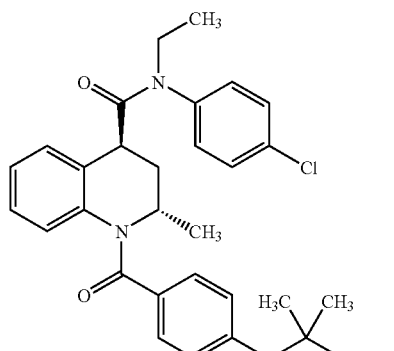
13
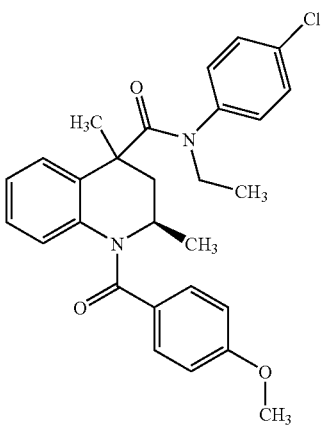
14
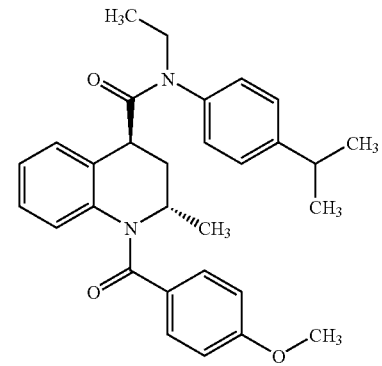
15

TABLE 1-continued
Examples of formula I compounds
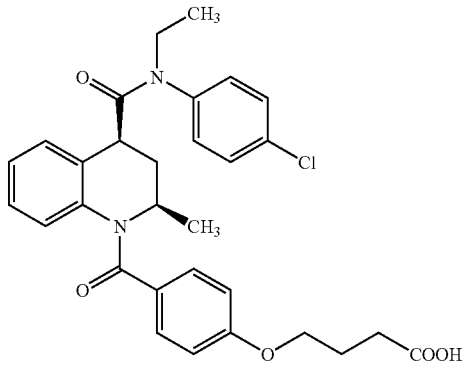
16
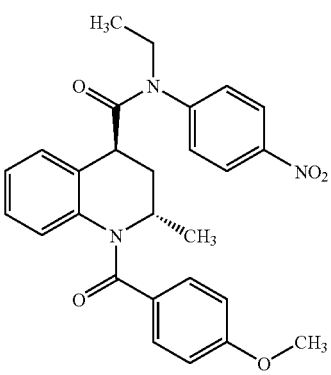
17
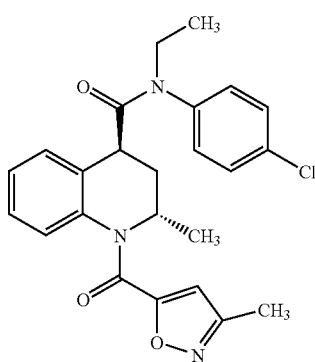
18
TABLE 1-continued
Examples of formula I compounds
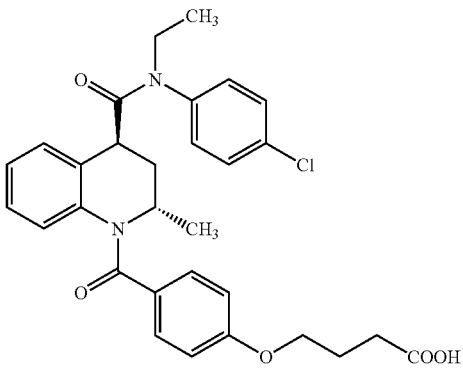
19
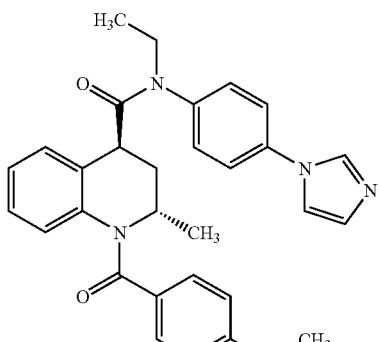
20
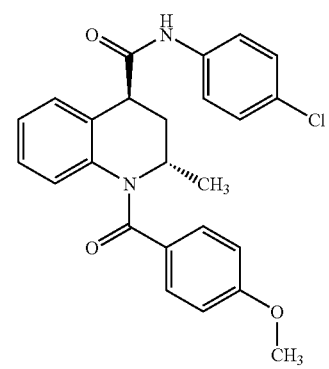
21

TABLE 1-continued
Examples of formula I compounds
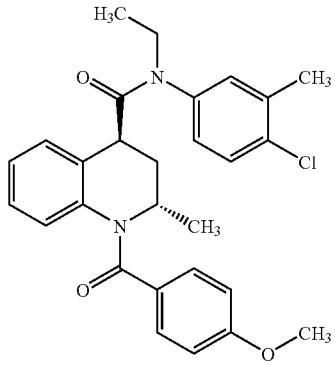
22
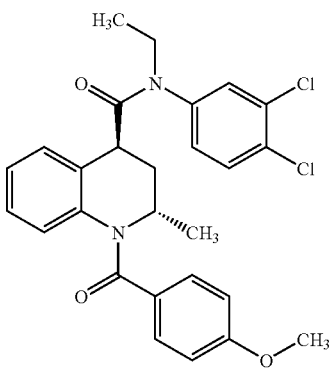
25
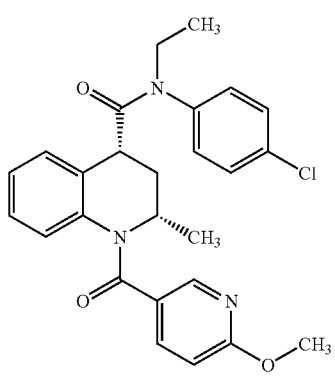
23
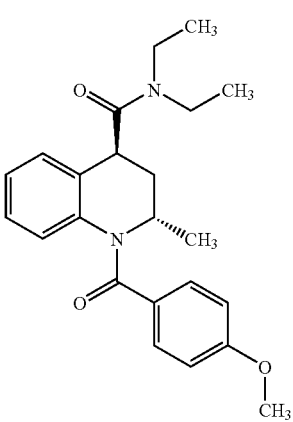
26
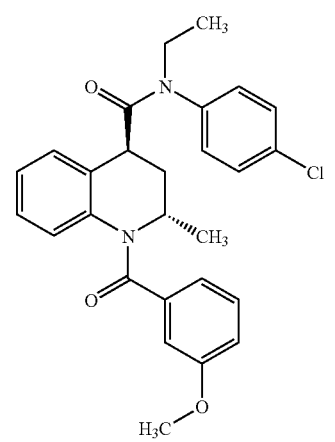
24
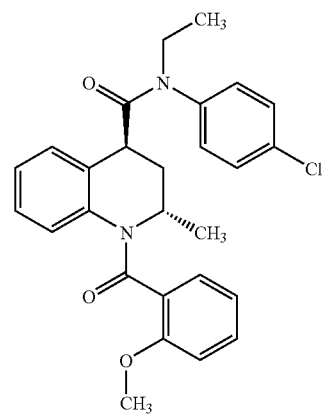
27

TABLE 1-continued
Examples of formula I compounds
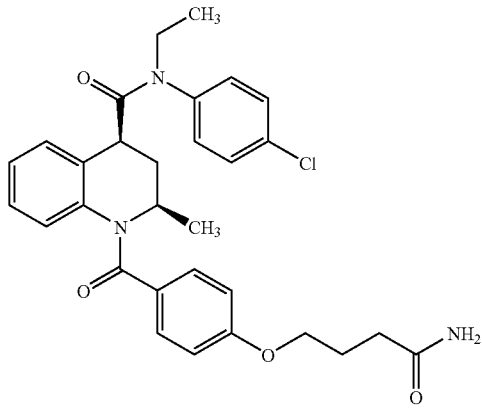
28
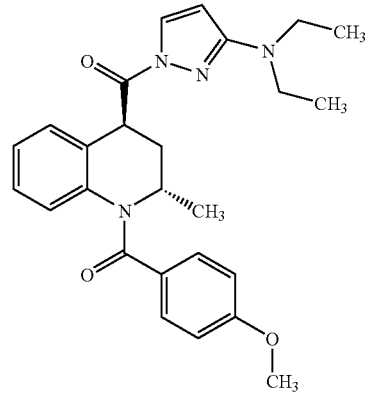
29
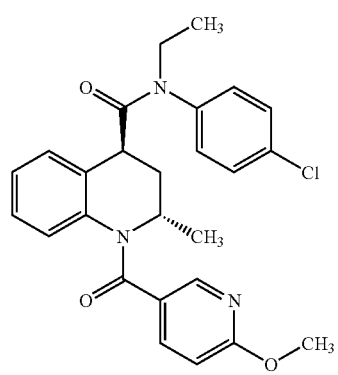
30
TABLE 1-continued
Examples of formula I compounds
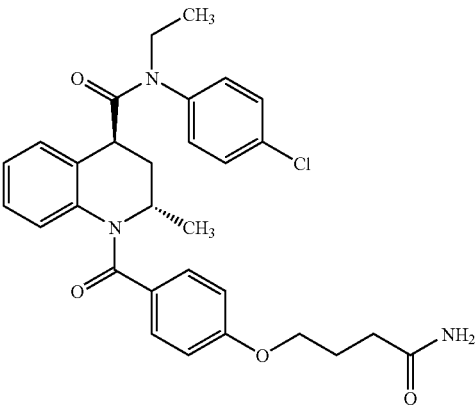
31
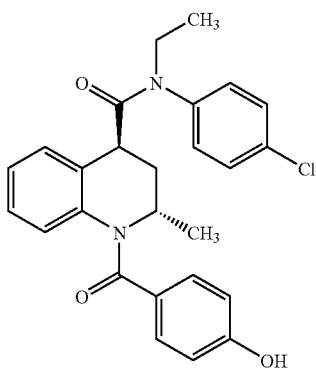
32
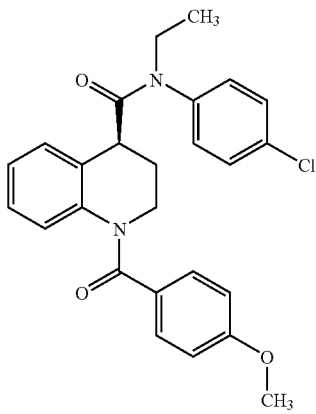
33

TABLE 1-continued
Examples of formula I compounds
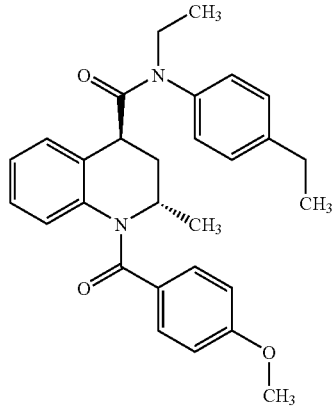
34
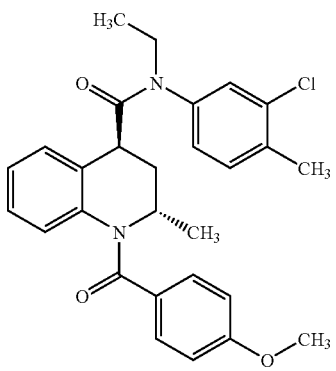
37
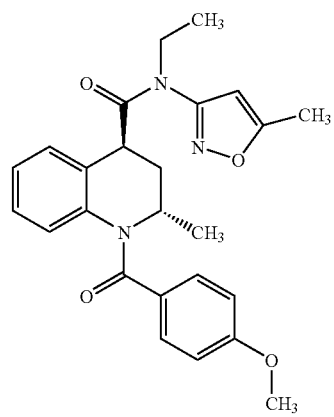
35
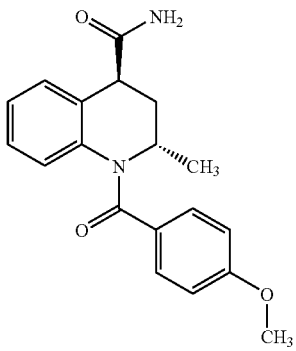
38
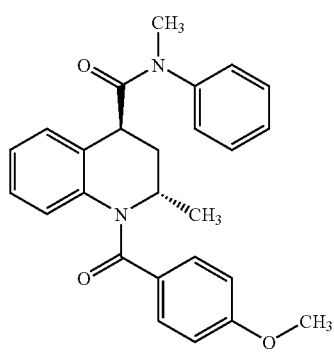
36
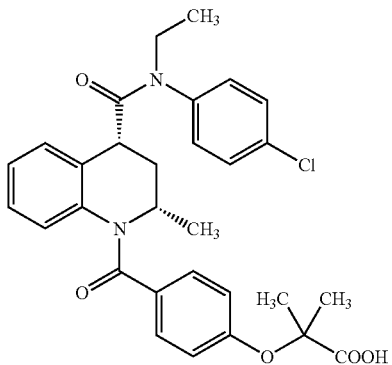
39

TABLE 1-continued
Examples of formula I compounds
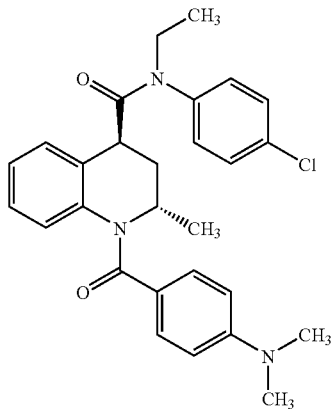
40
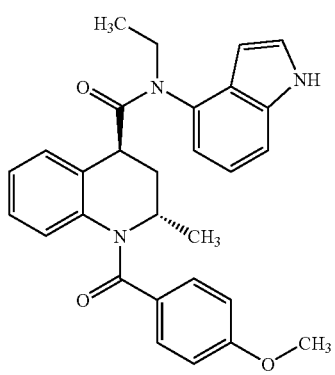
41
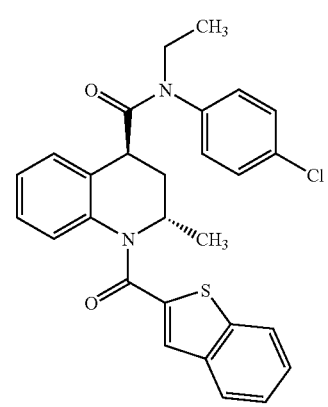
42
TABLE 1-continued
Examples of formula I compounds
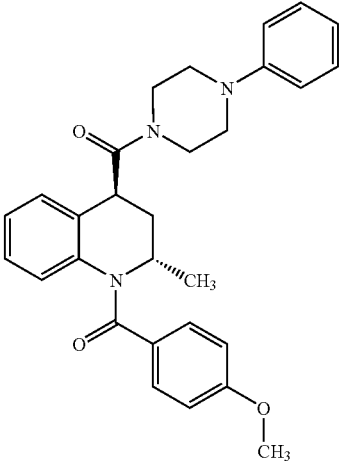
43
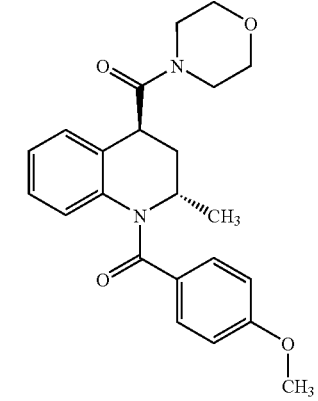
44
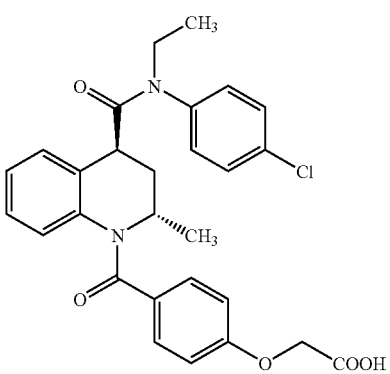
45

TABLE 1-continued
Examples of formula I compounds
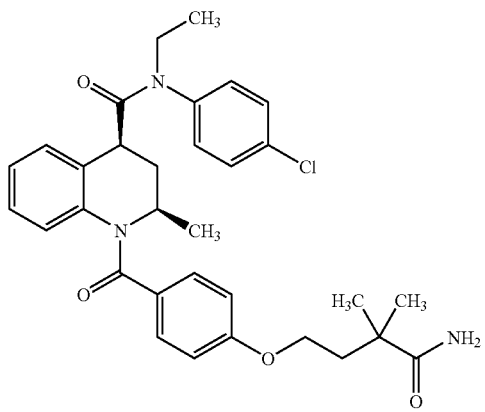
46
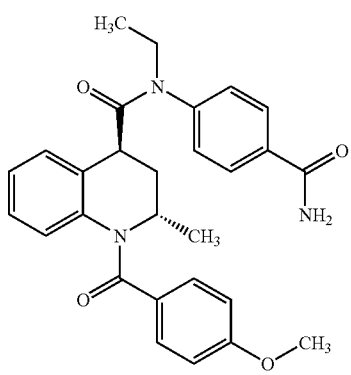
47
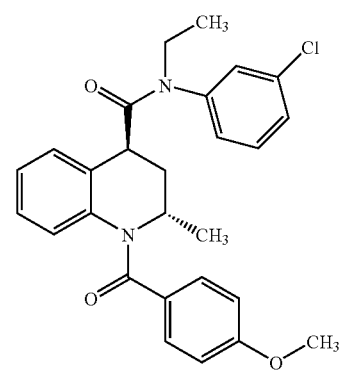
48
TABLE 1-continued
Examples of formula I compounds
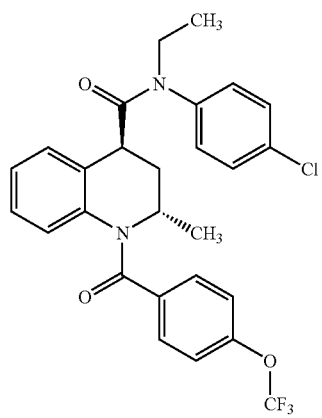
49
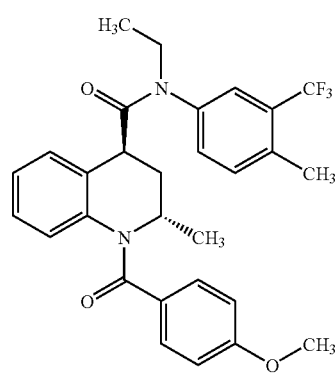
50
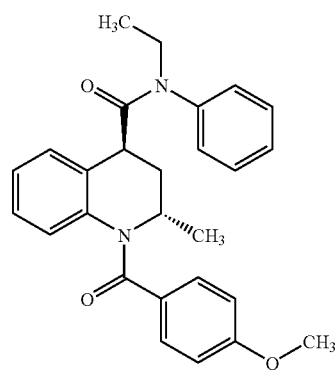
51

TABLE 1-continued
Examples of formula I compounds
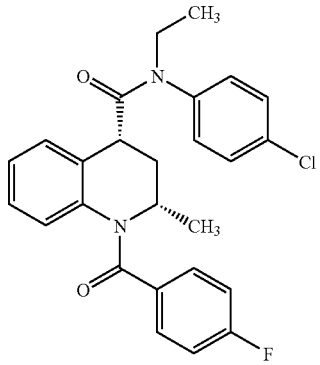
52
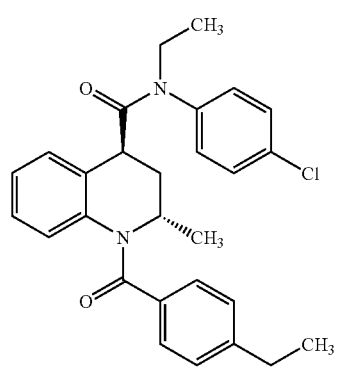
53
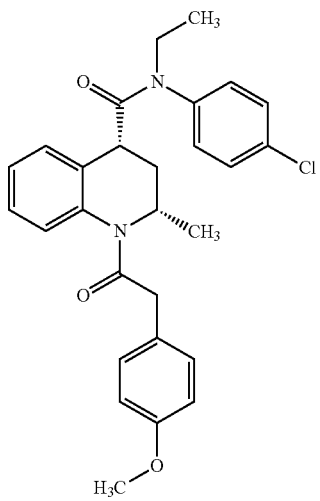
54
TABLE 1-continued
Examples of formula I compounds
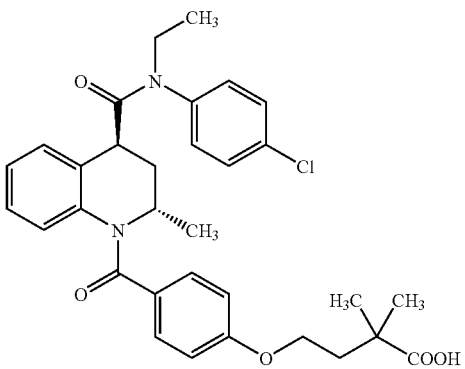
55
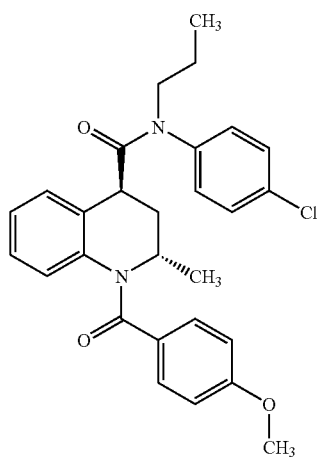
56
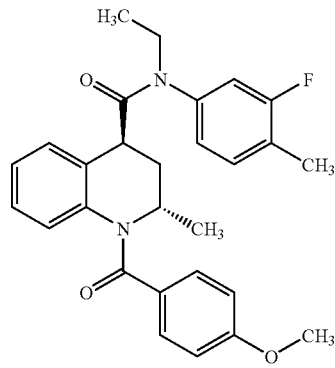
57

TABLE 1-continued
Examples of formula I compounds
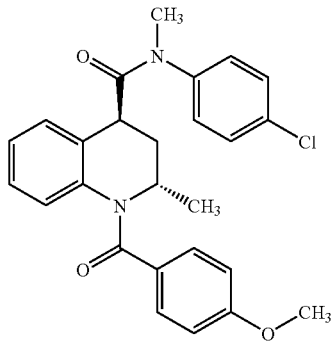
58
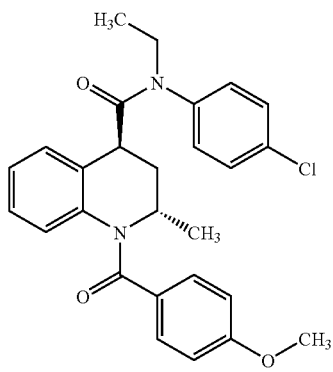
59
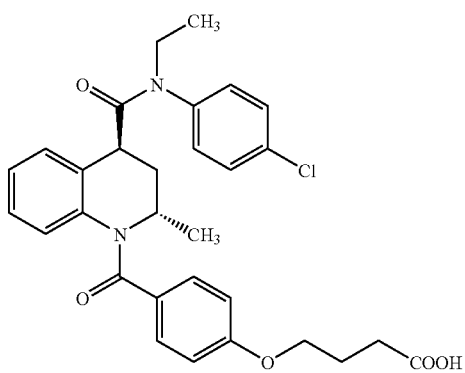
60
TABLE 1-continued
Examples of formula I compounds
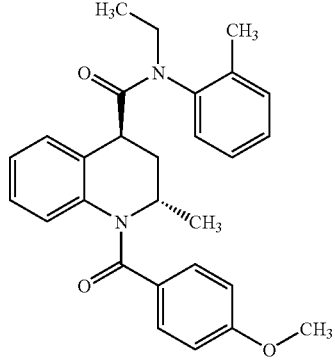
61
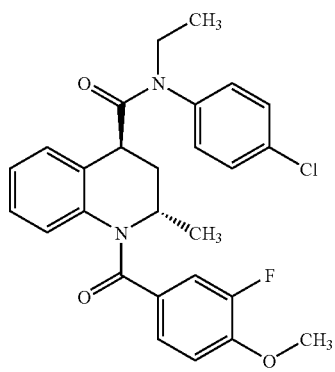
62
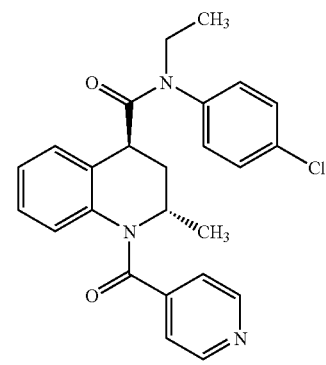
63

TABLE 1-continued
Examples of formula I compounds
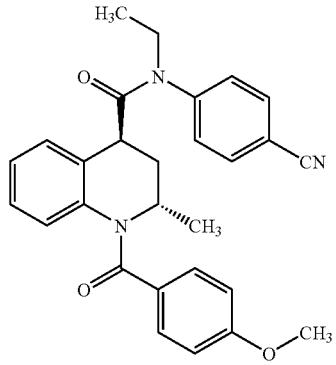
64
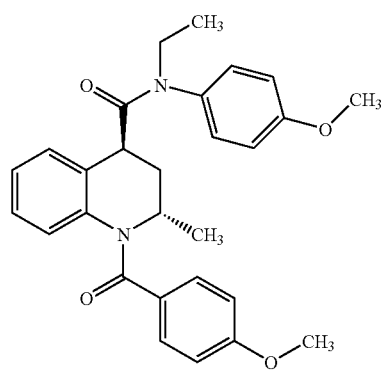
65
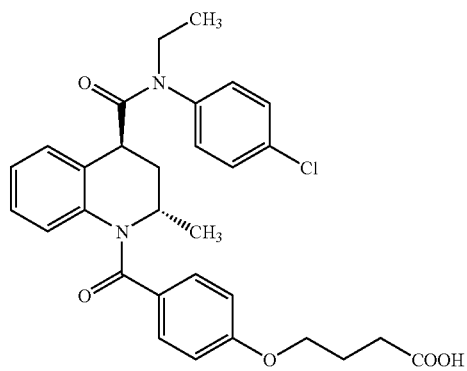
66
TABLE 1-continued
Examples of formula I compounds
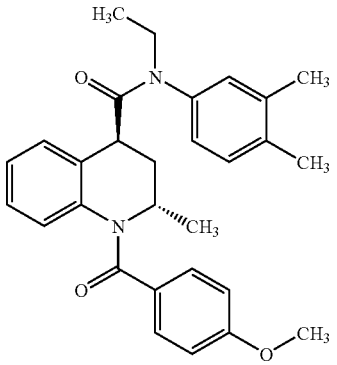
67
68
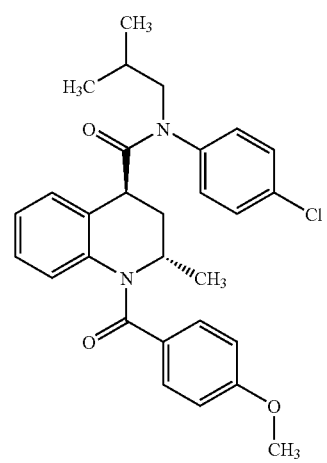
69

TABLE 1-continued
Examples of formula I compounds
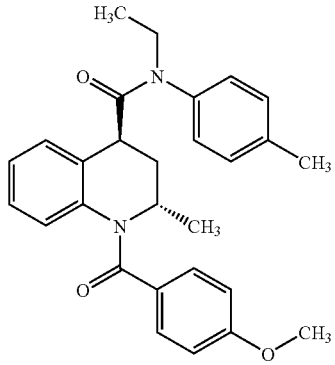
70
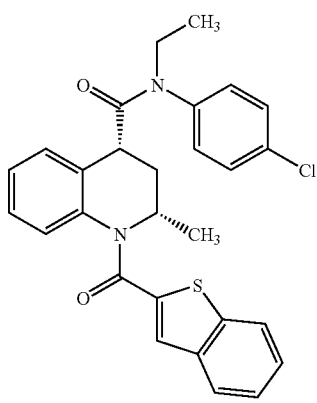
71
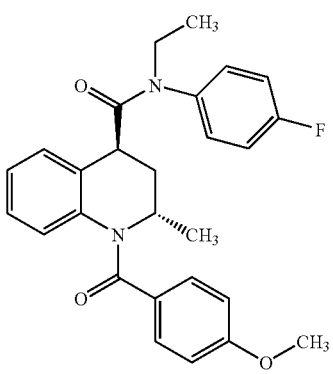
72
TABLE 1-continued
Examples of formula I compounds
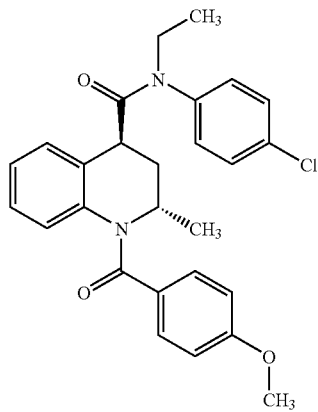
73
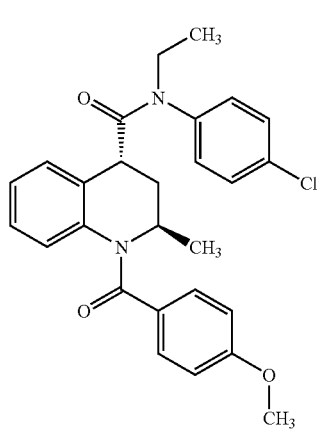
74
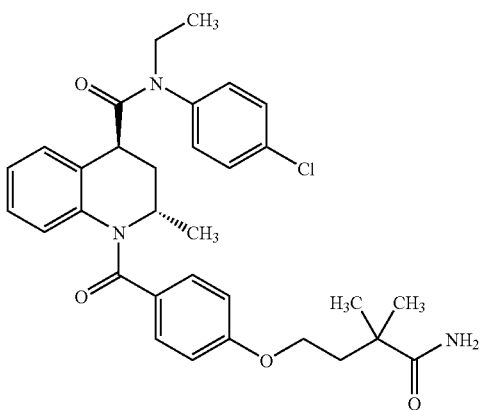
75

TABLE 1-continued
Examples of formula I compounds
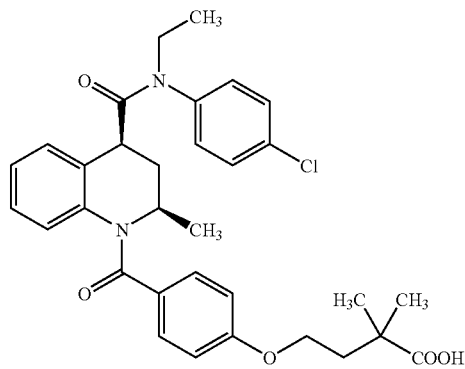
76
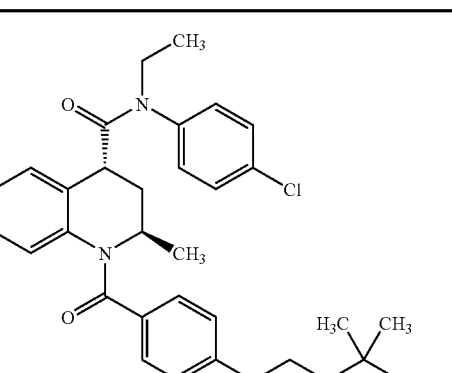
79
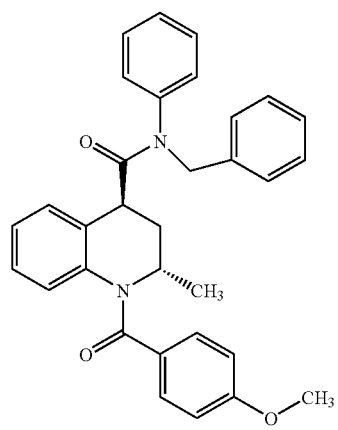
77
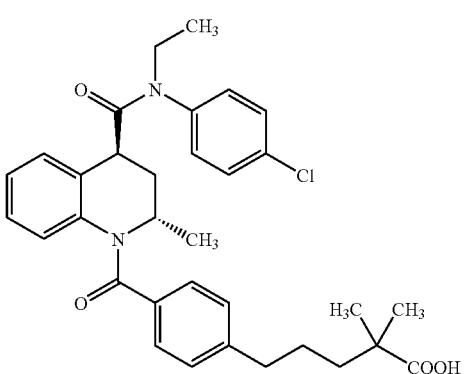
80
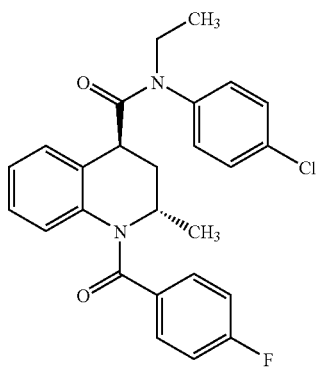
78
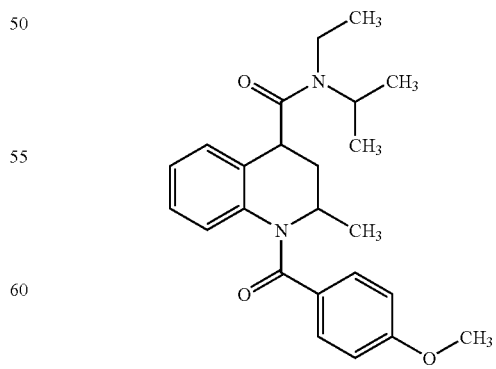
81

TABLE 1-continued
Examples of formula I compounds
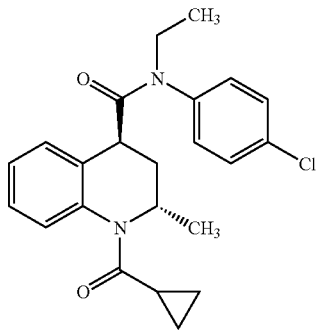
82
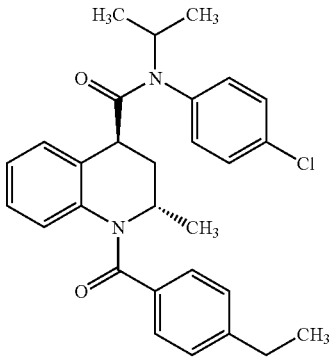
85
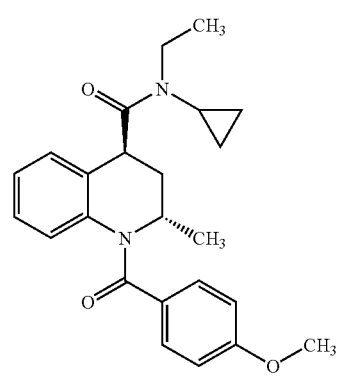
83
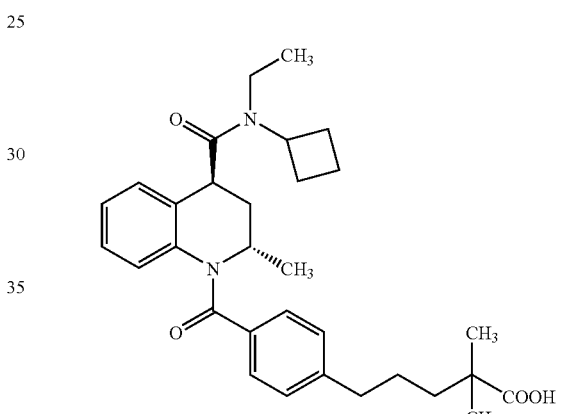
86
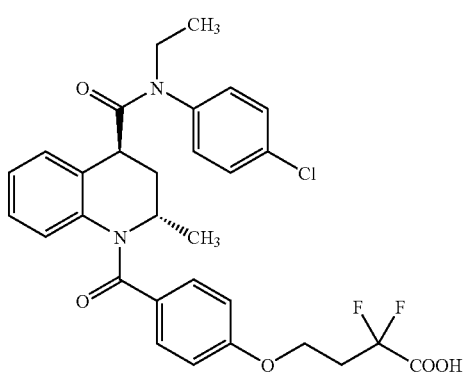
84
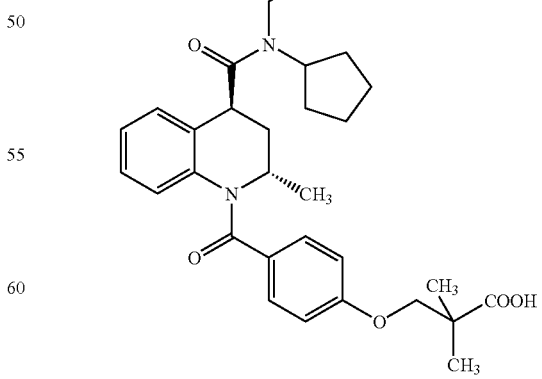
87

TABLE 1-continued
Examples of formula I compounds
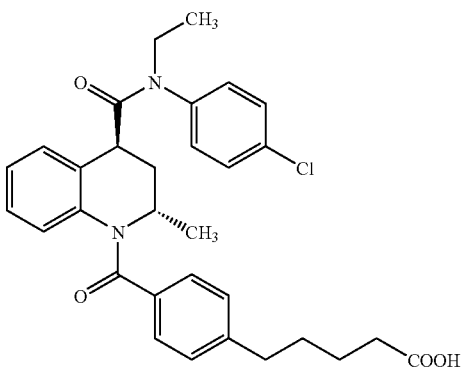
88
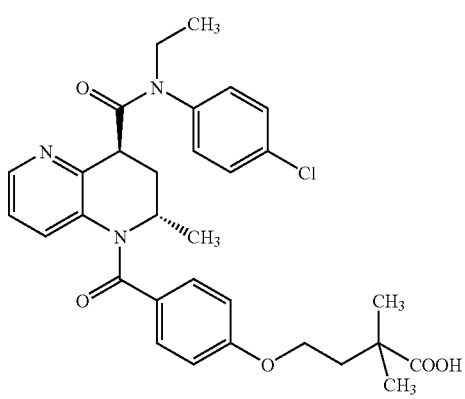
89
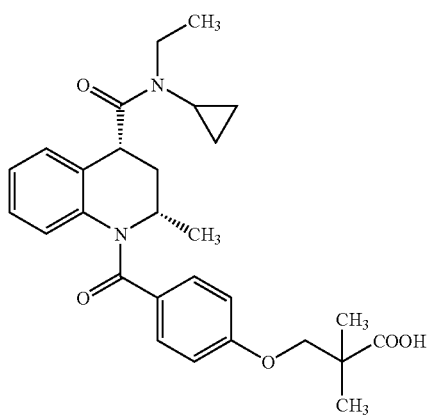
90
TABLE 1-continued
Examples of formula I compounds
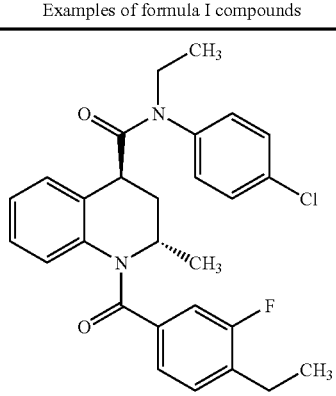
91
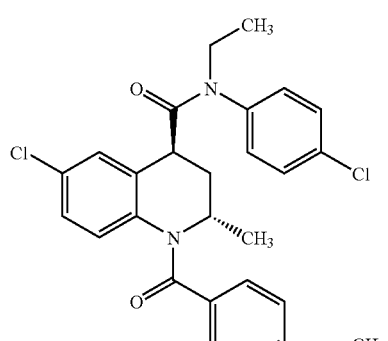
92
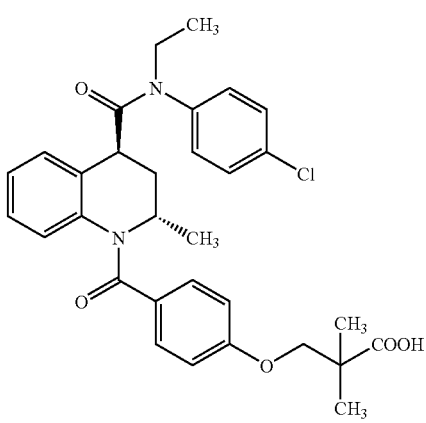
93

TABLE 1-continued
Examples of formula I compounds
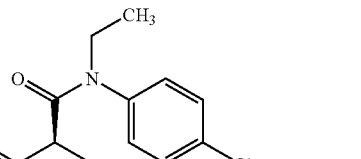
94
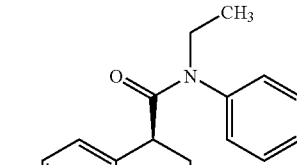
95
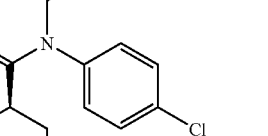
96
TABLE 1-continued
Examples of formula I compounds
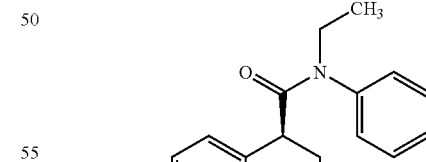
97
98
99

TABLE 1-continued
Examples of formula I compounds
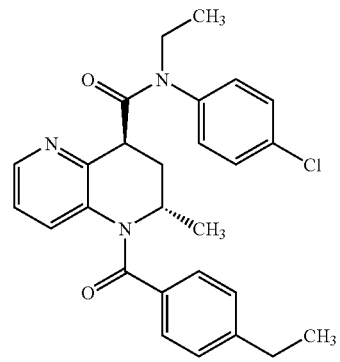
100
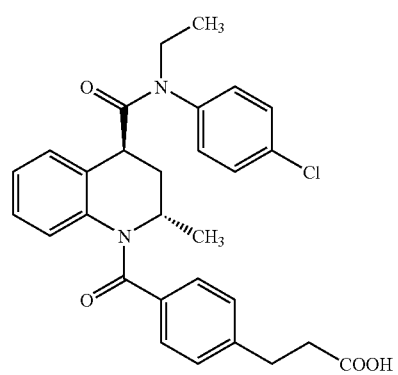
101
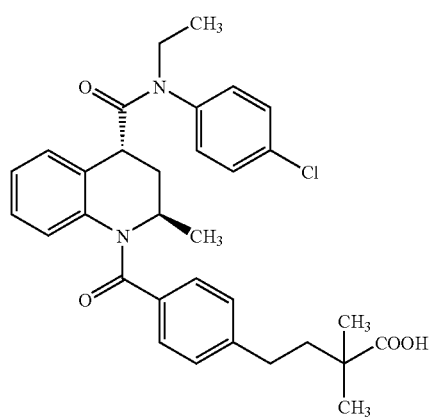
102
TABLE 1-continued
Examples of formula I compounds
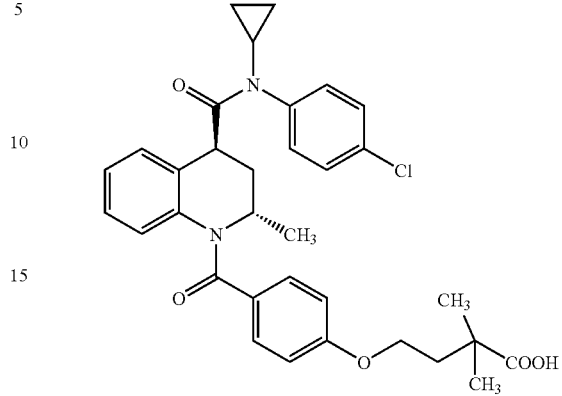
103
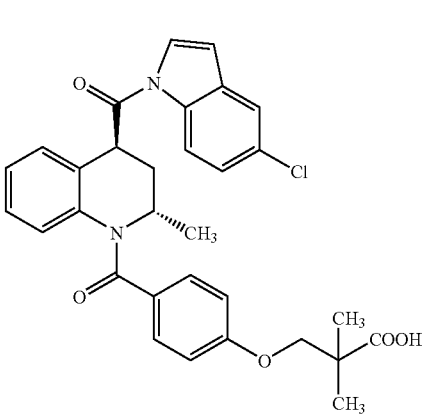
104
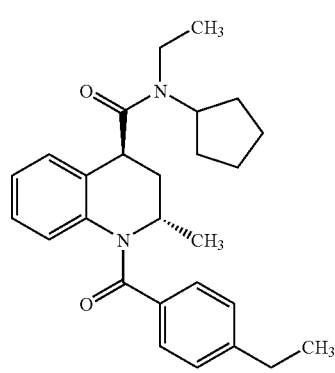
105

TABLE 1-continued
Examples of formula I compounds
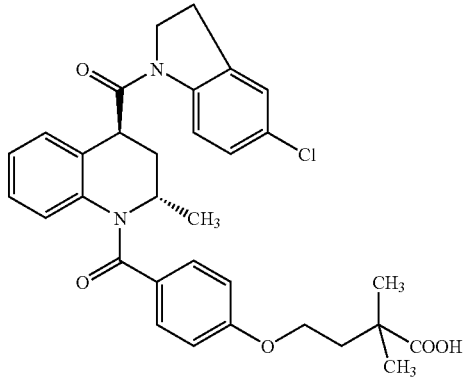
106
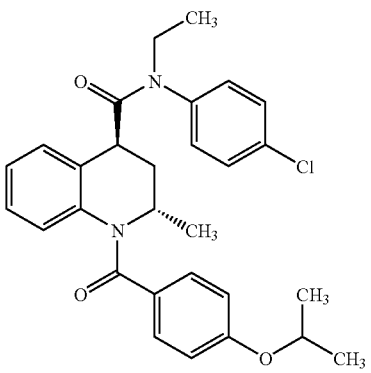
109
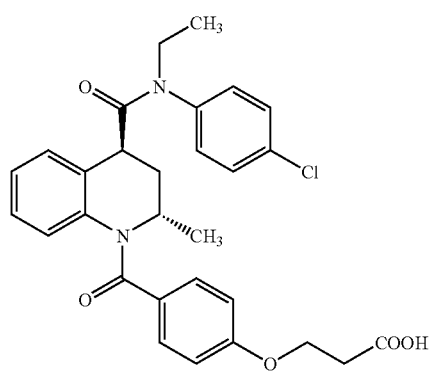
107
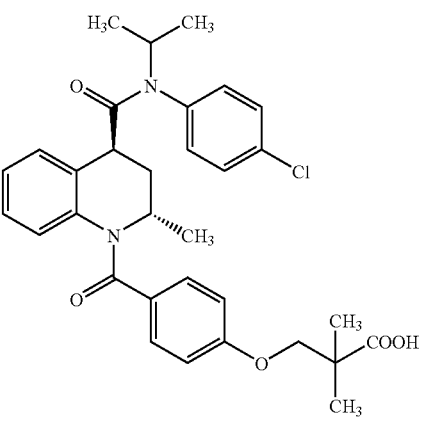
110
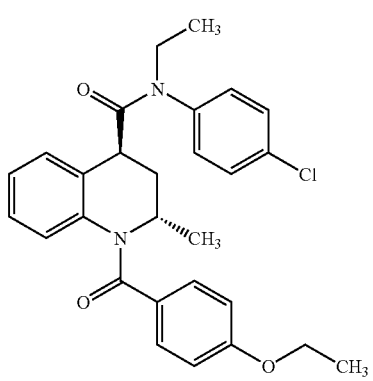
108
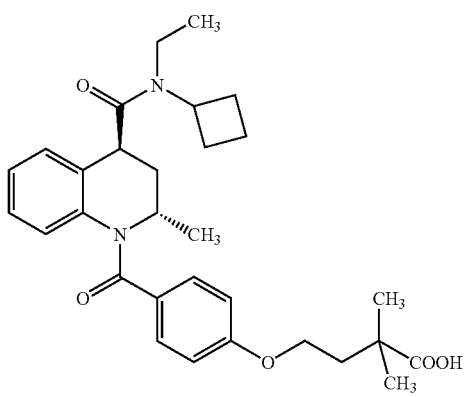
111

TABLE 1-continued
Examples of formula I compounds
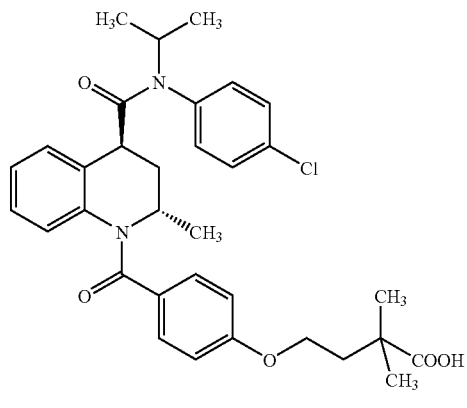
112
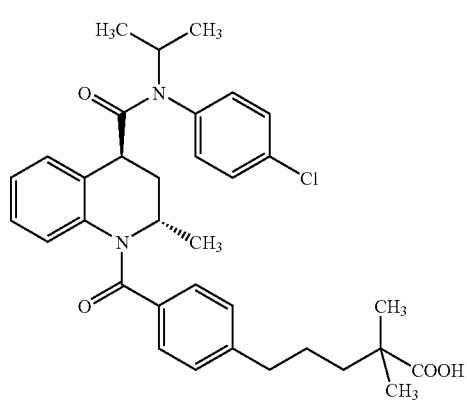
113
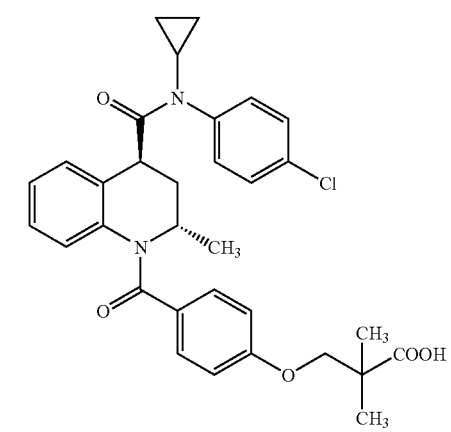
114
TABLE 1-continued
Examples of formula I compounds
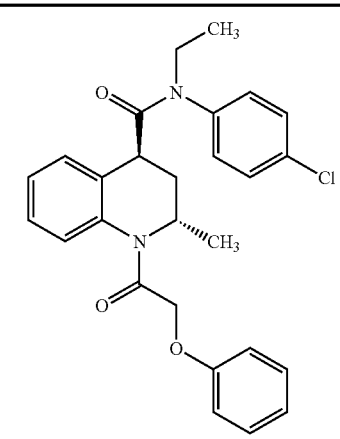
115
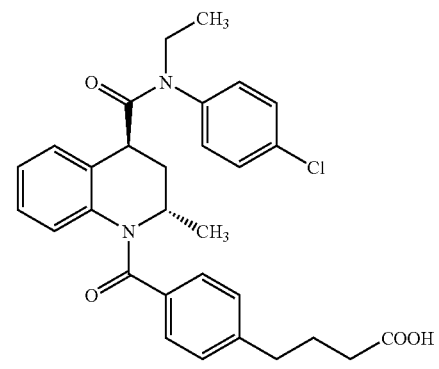
116
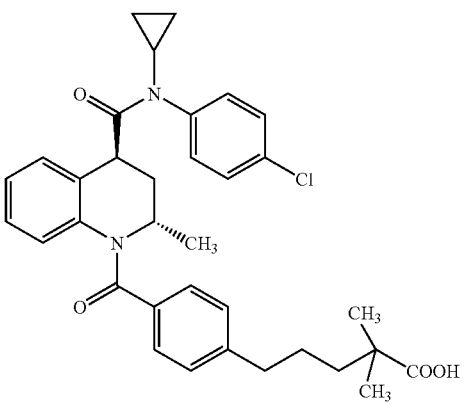
117

TABLE 1-continued
Examples of formula I compounds
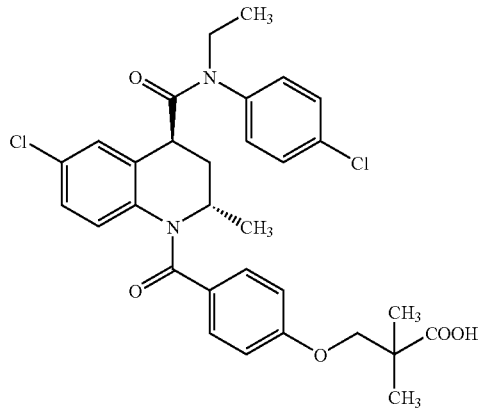
118
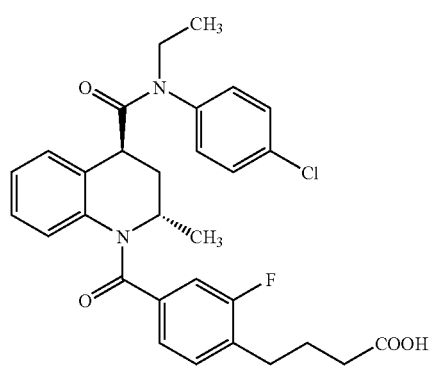
119
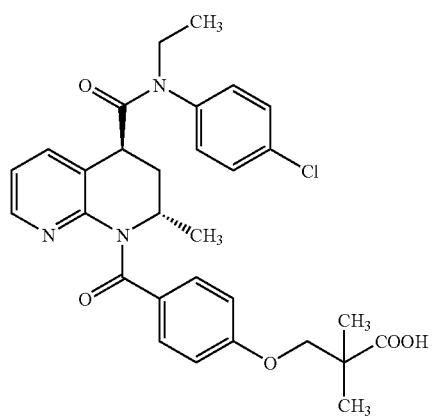
120
TABLE 1-continued
Examples of formula I compounds
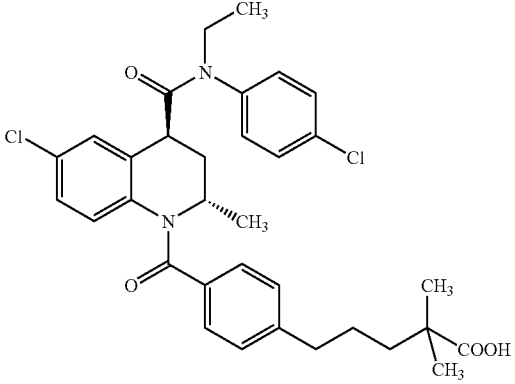
121
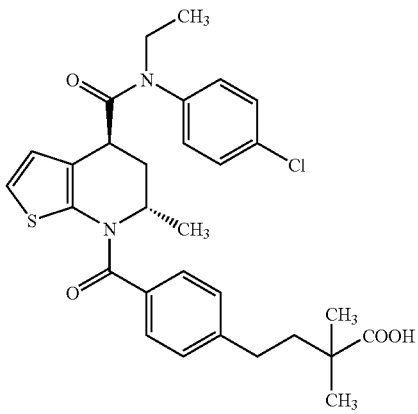
122
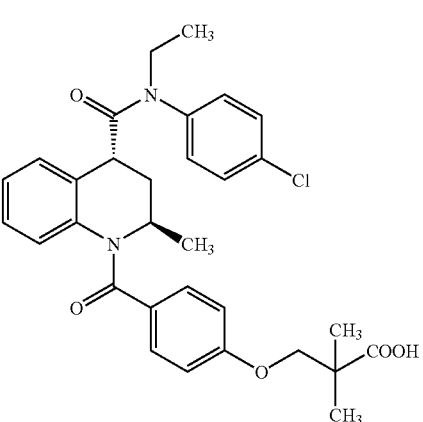
123

TABLE 1-continued
Examples of formula I compounds
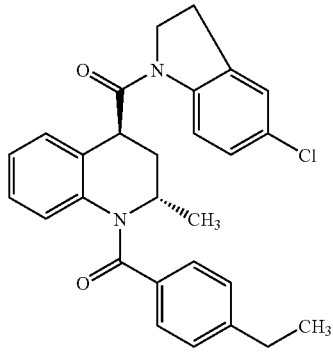
124
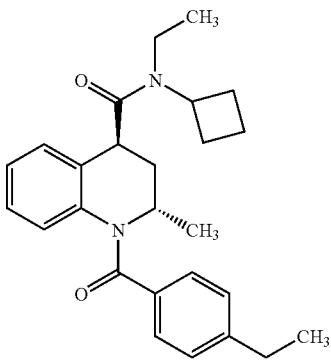
127
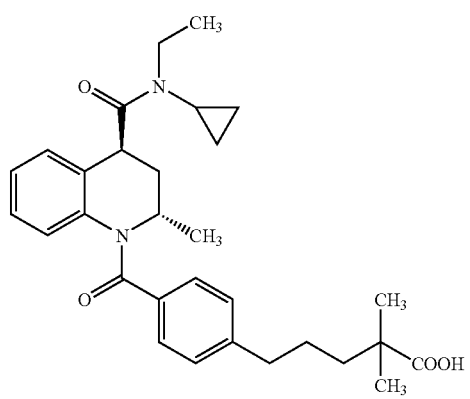
125
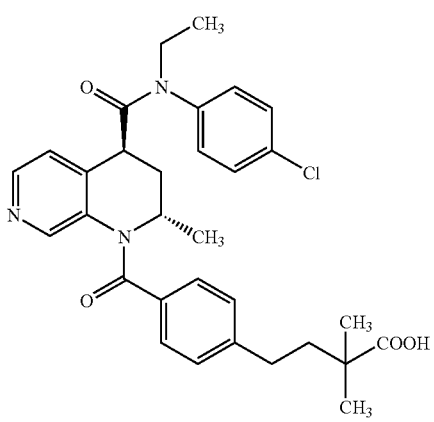
128
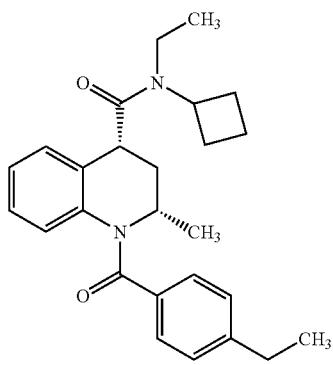
126
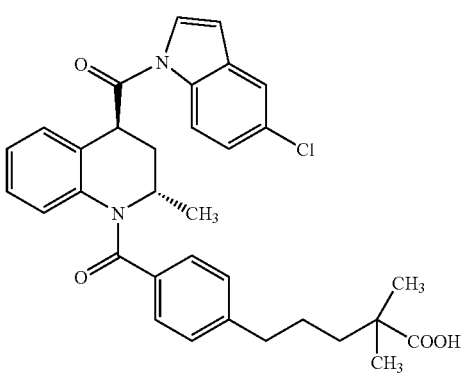
129

TABLE 1-continued
Examples of formula I compounds
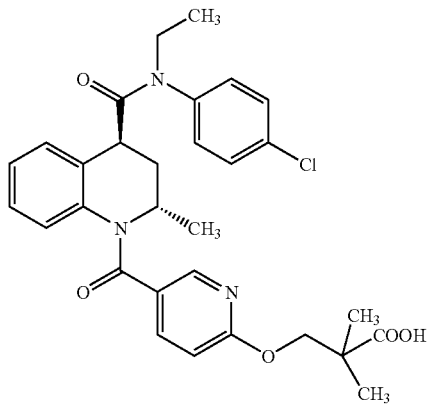
130
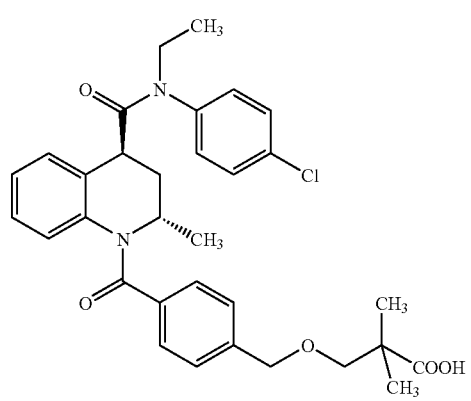
131
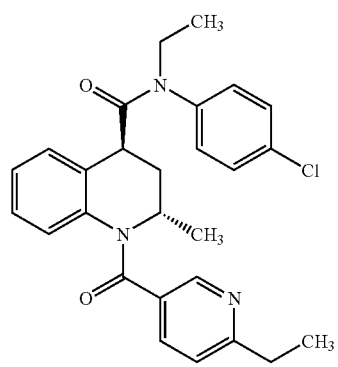
132
TABLE 1-continued
Examples of formula I compounds
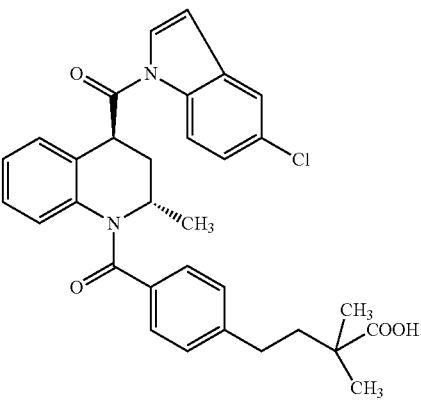
133
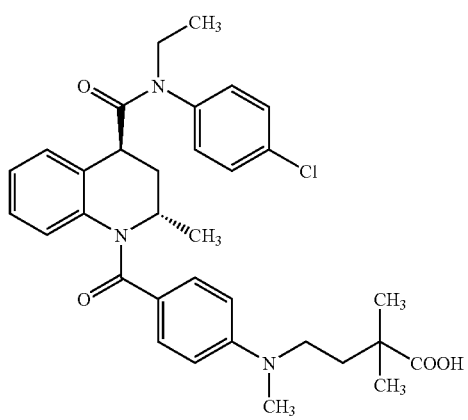
134
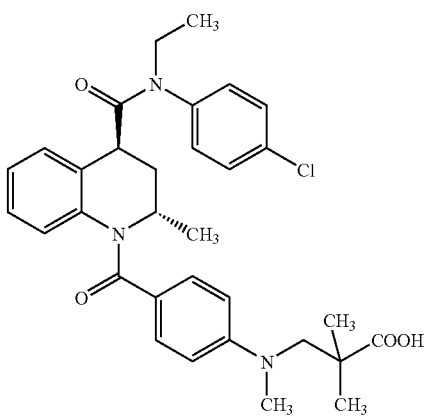
135

TABLE 1-continued
Examples of formula I compounds
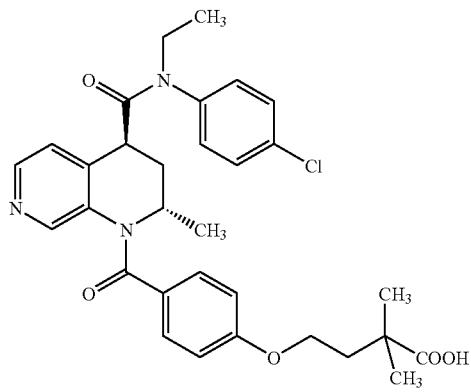
136
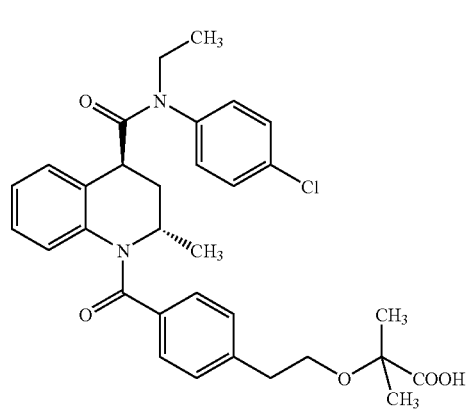
137
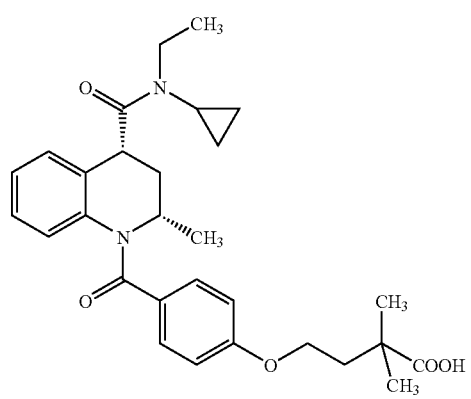
138
TABLE 1-continued
Examples of formula I compounds
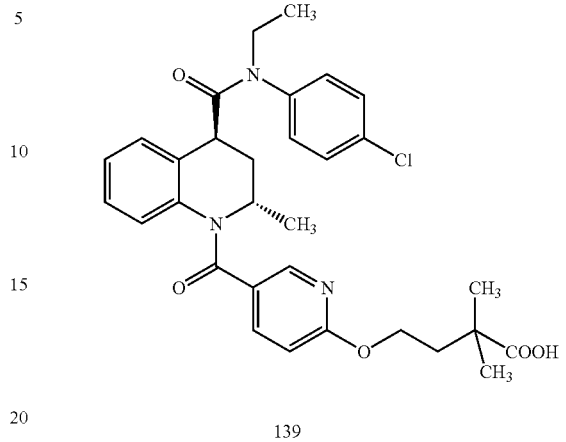
139
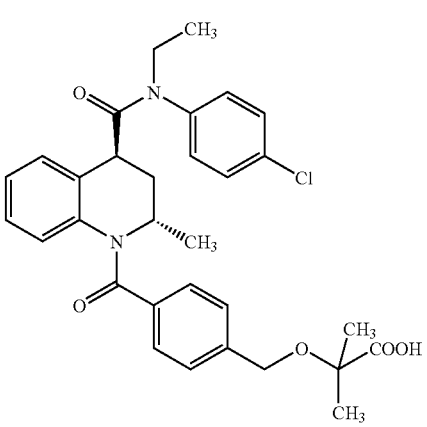
140
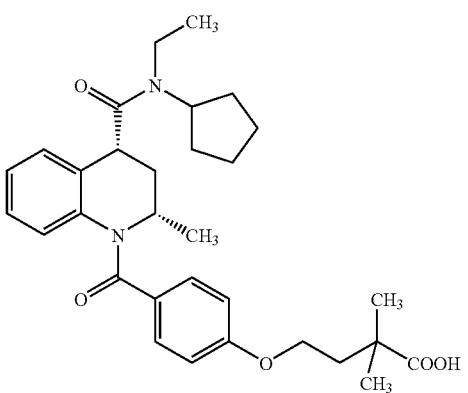
141

TABLE 1-continued
Examples of formula I compounds
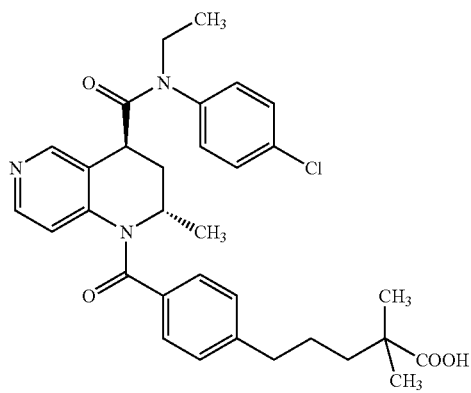
142
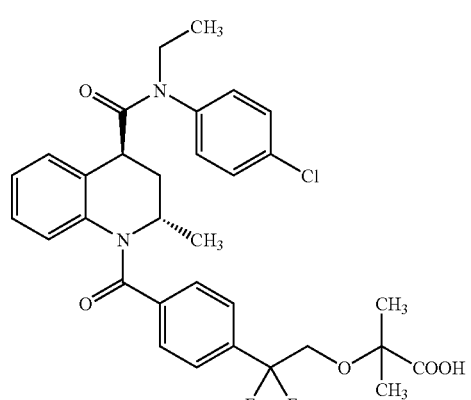
143
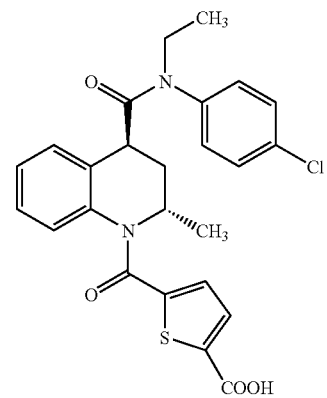
144
TABLE 1-continued
Examples of formula I compounds
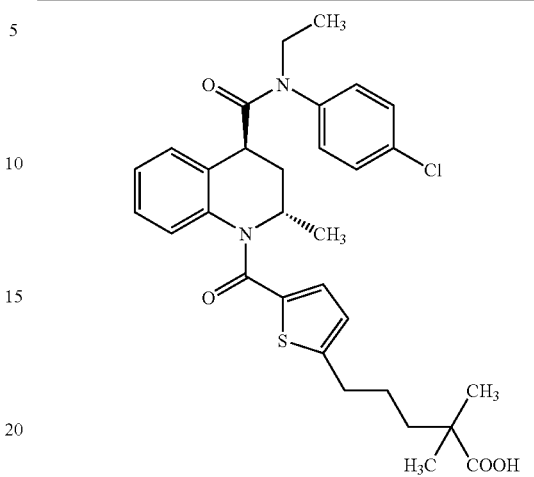
145
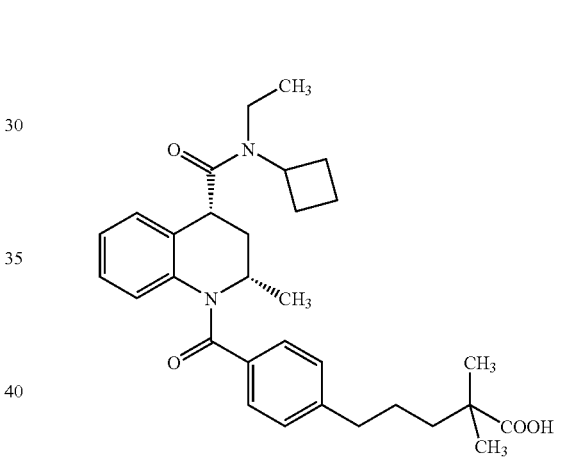
146
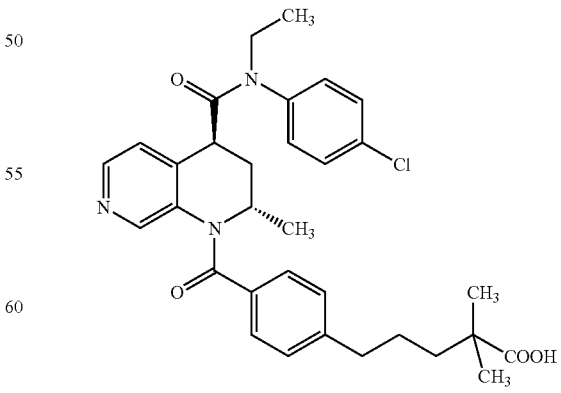
147

TABLE 1-continued
Examples of formula I compounds
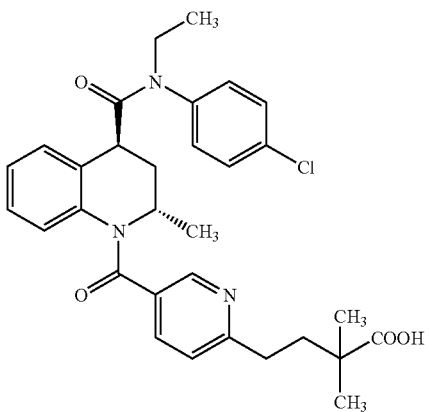
148
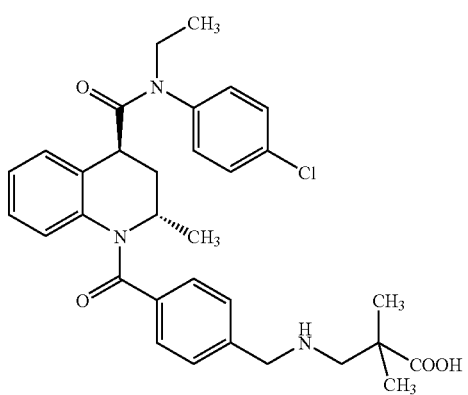
149
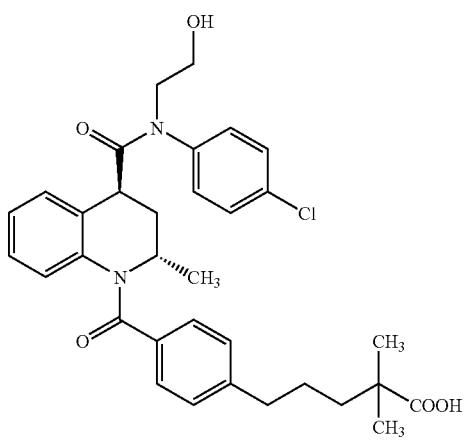
150
TABLE 1-continued
Examples of formula I compounds
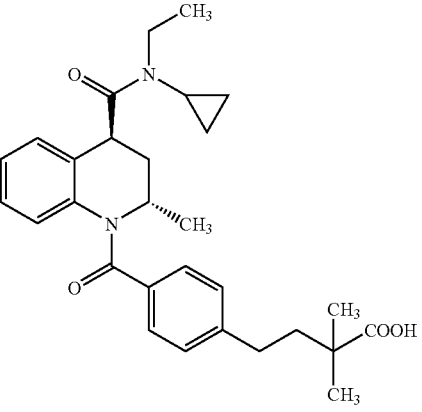
151
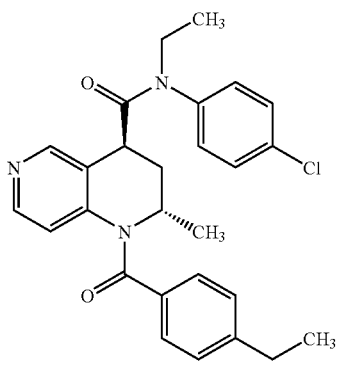
152
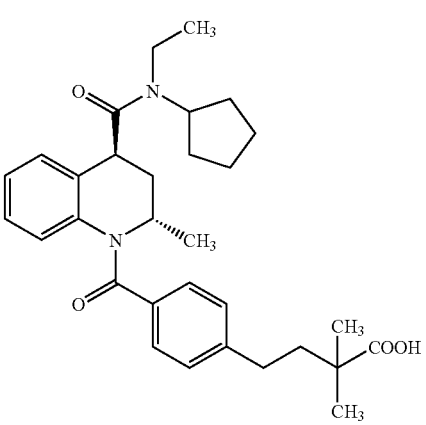
153

TABLE 1-continued
Examples of formula I compounds
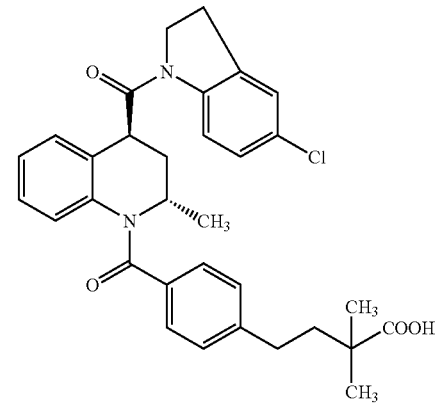
154
155
156
157
158
159

TABLE 1-continued
Examples of formula I compounds
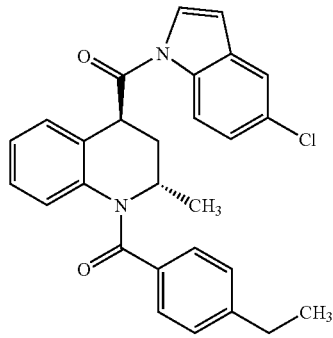
160
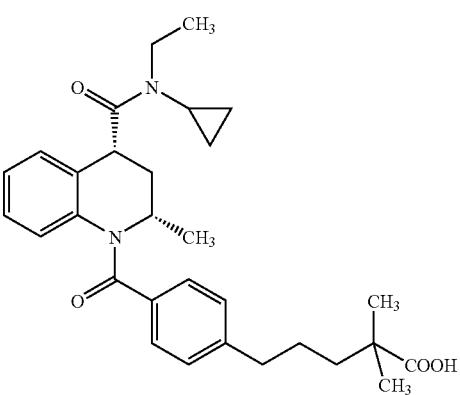
161
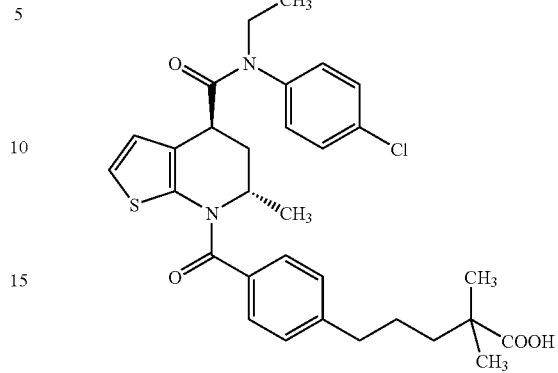
163
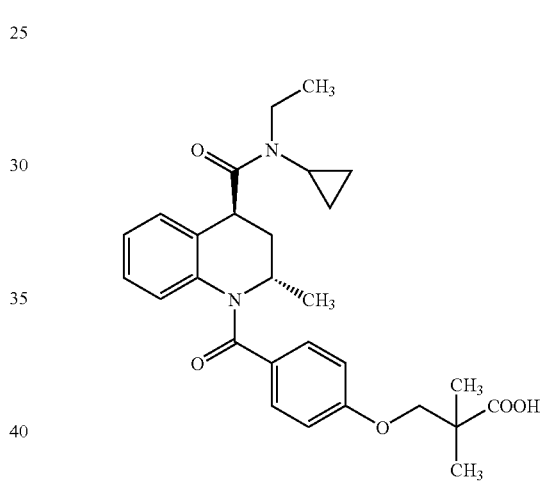
164
162
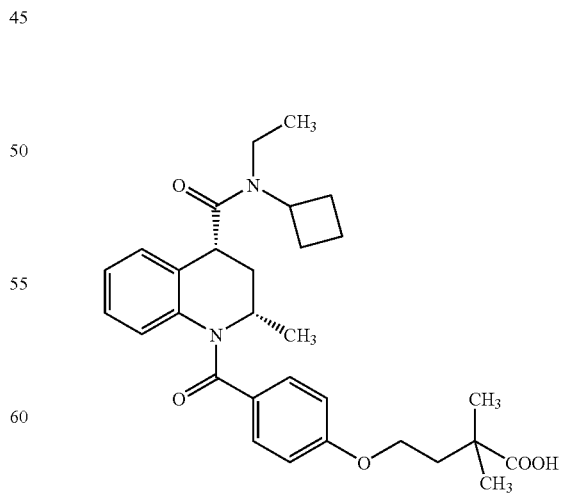
165

TABLE 1-continued
Examples of formula I compounds
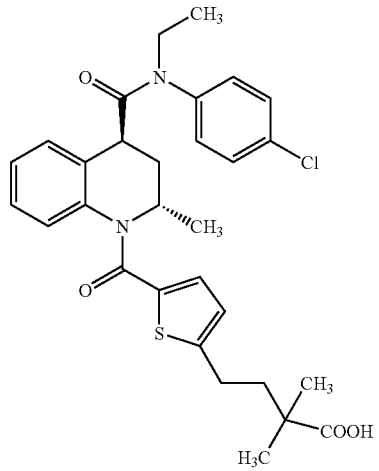
166
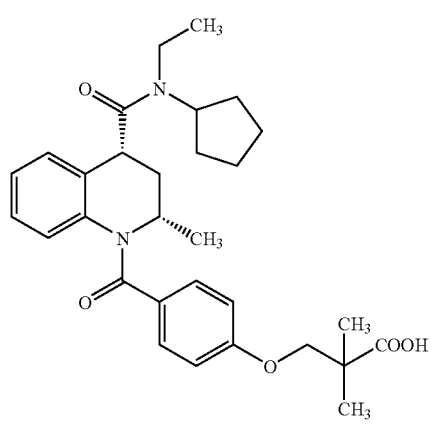
167
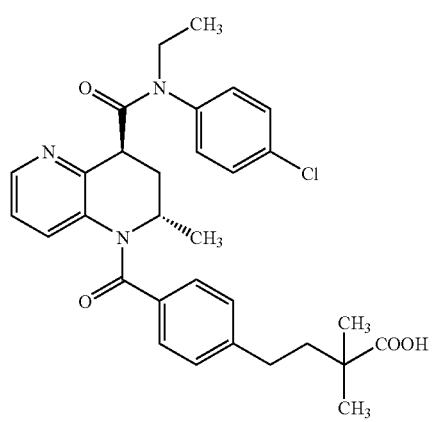
168
TABLE 1-continued
Examples of formula I compounds
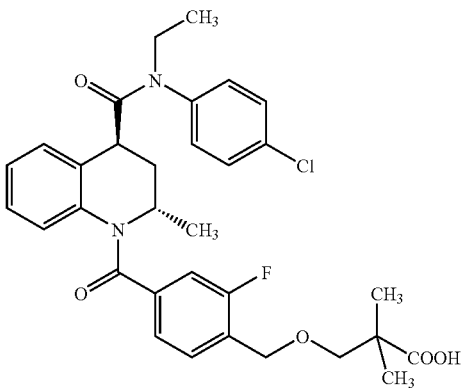
169
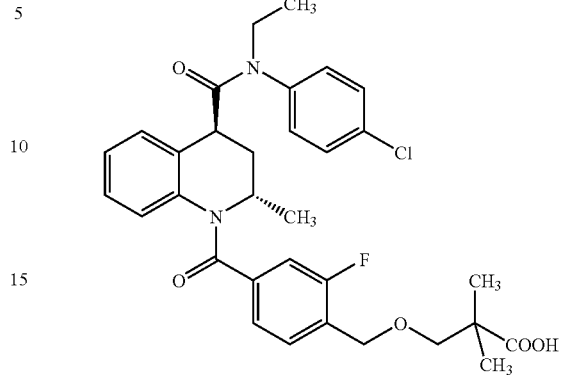
170
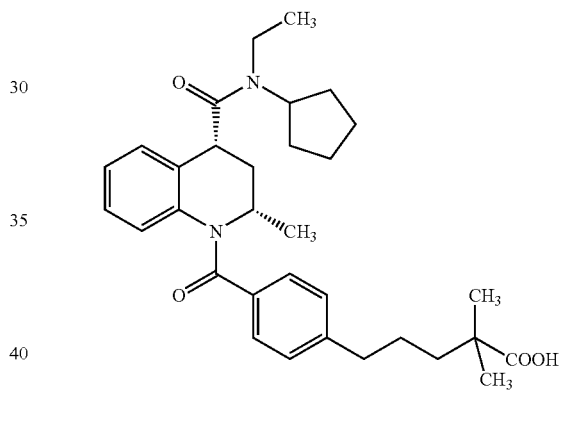
171

TABLE 1-continued
Examples of formula I compounds
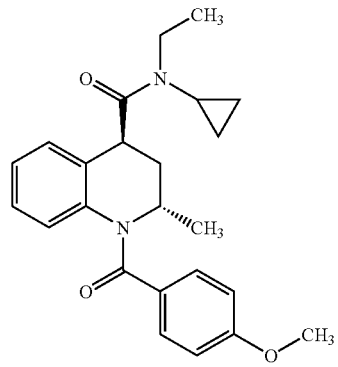
172
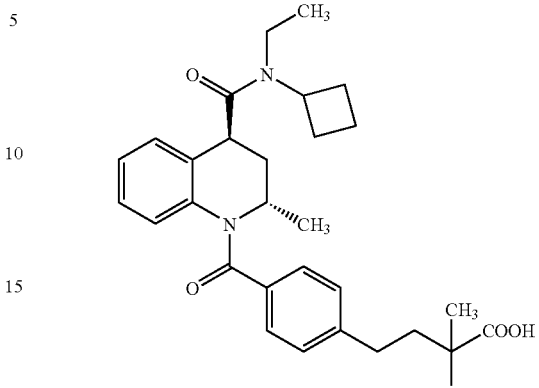
175
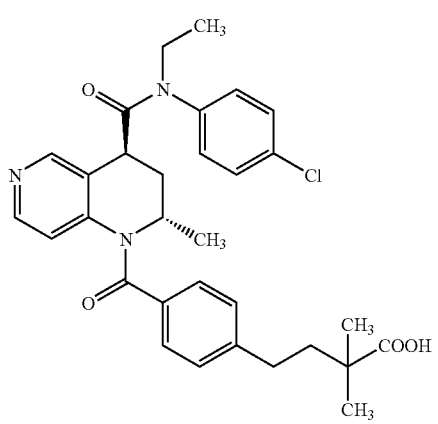
173
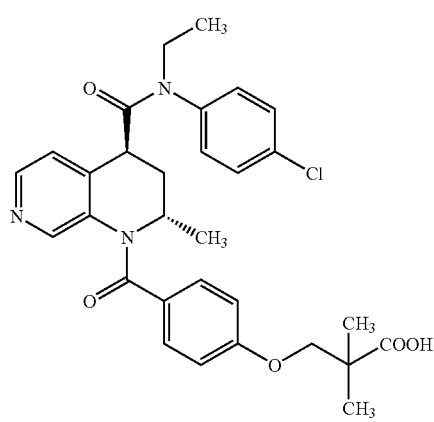
176
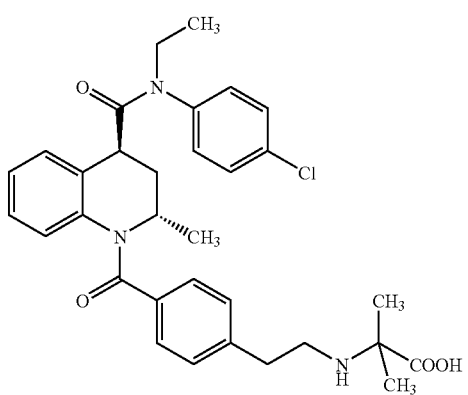
174
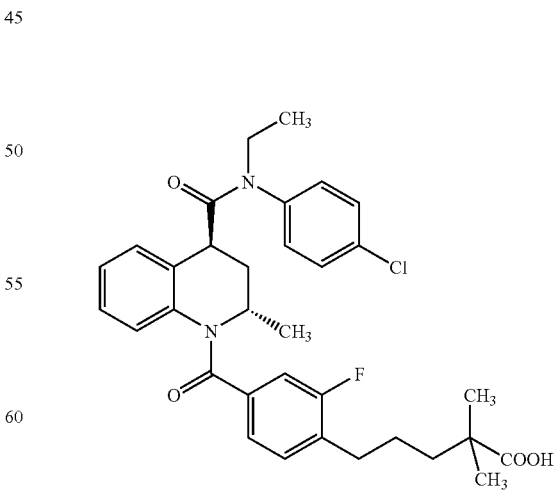
177

TABLE 1-continued
Examples of formula I compounds
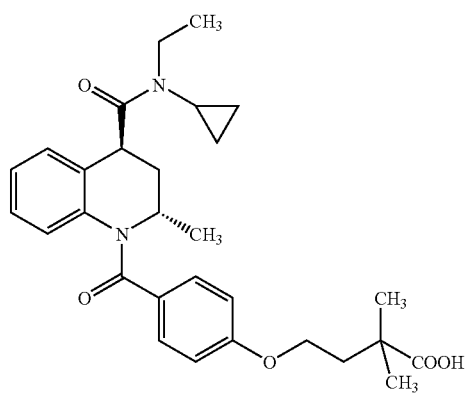
178
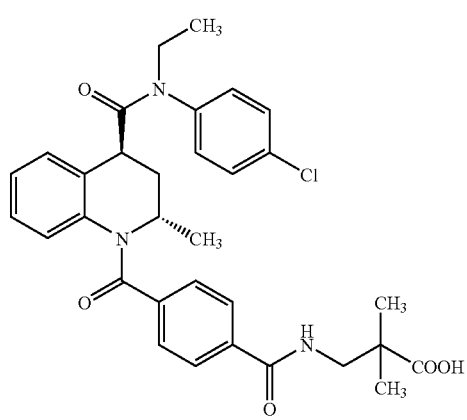
179
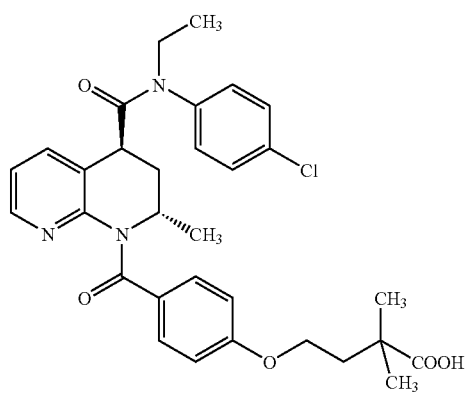
180
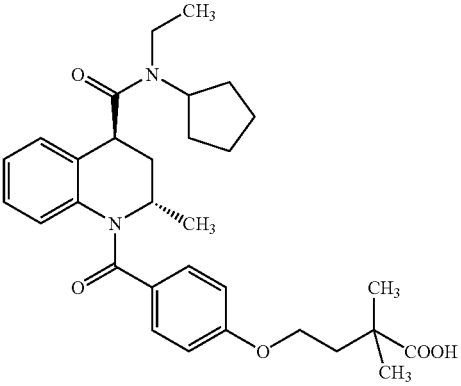
181
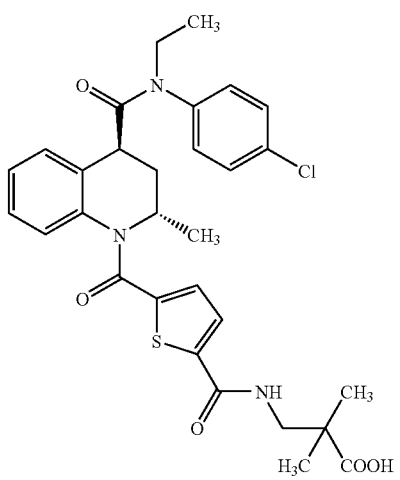
182
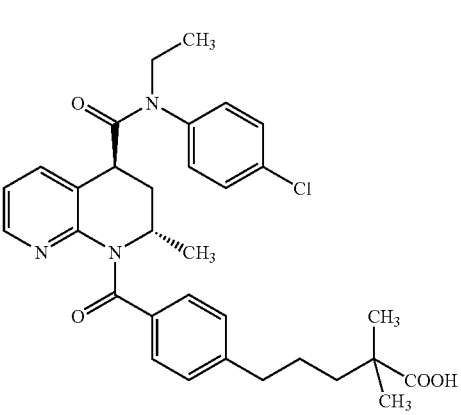
183

TABLE 1-continued
Examples of formula I compounds
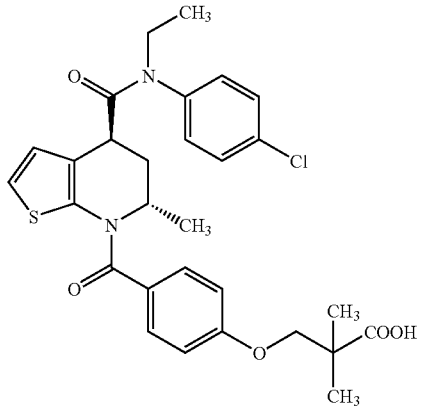
184
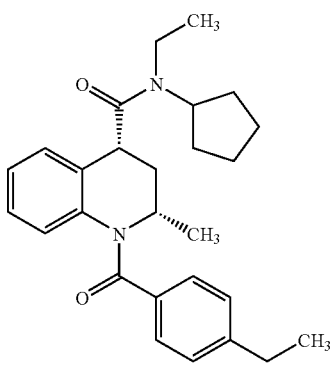
187
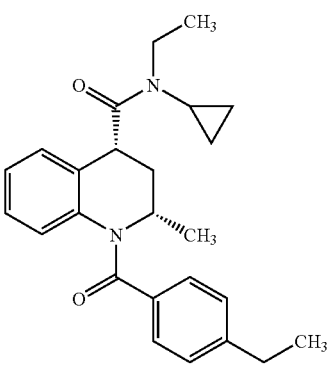
185
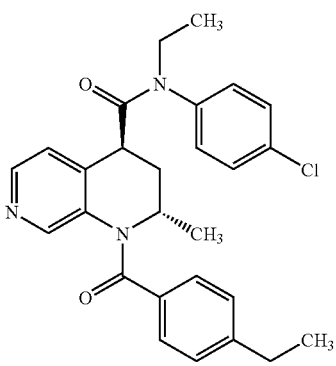
188
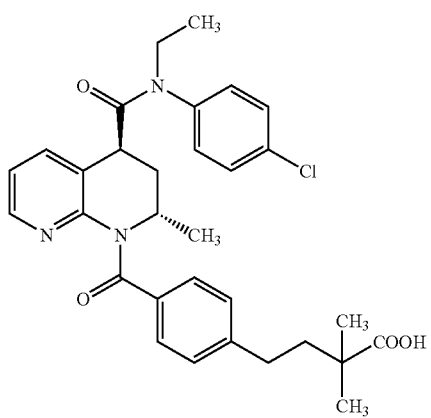
186
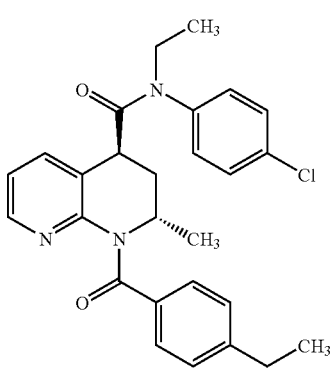
189

TABLE 1-continued
Examples of formula I compounds
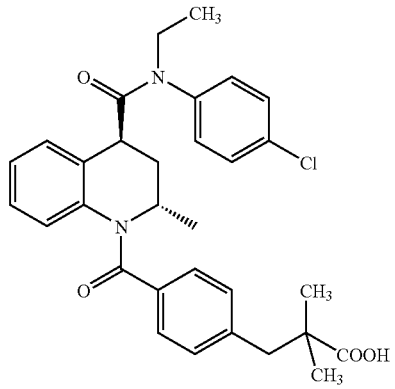
190
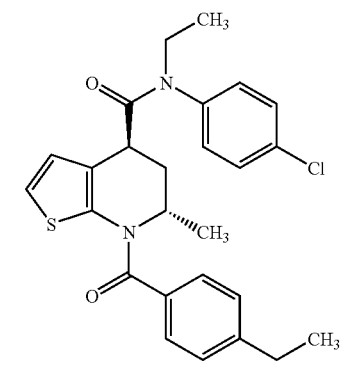
191
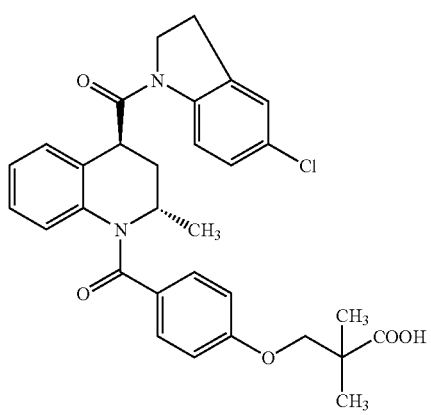
192
TABLE 1-continued
Examples of formula I compounds
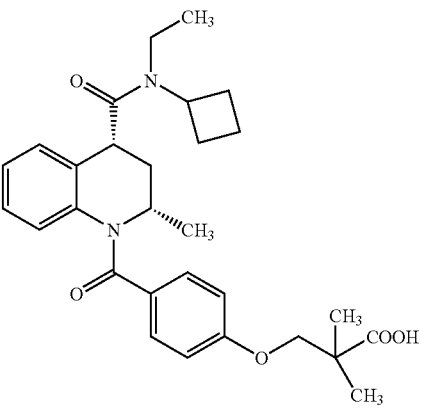
193
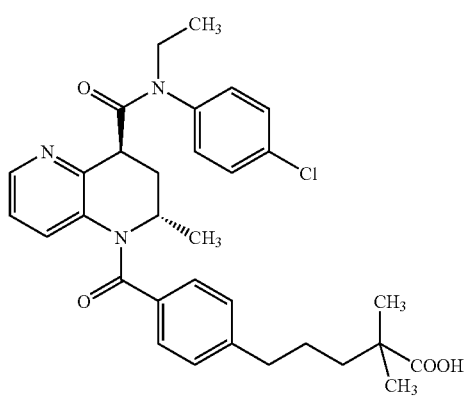
194
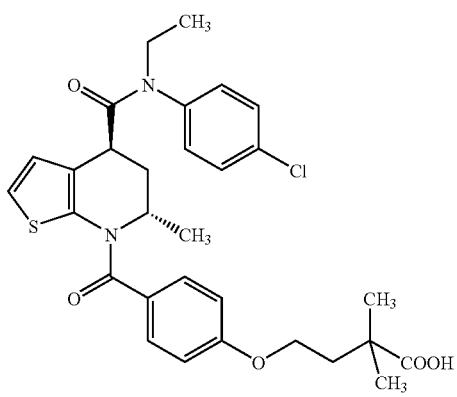
195

TABLE 1-continued
Examples of formula I compounds
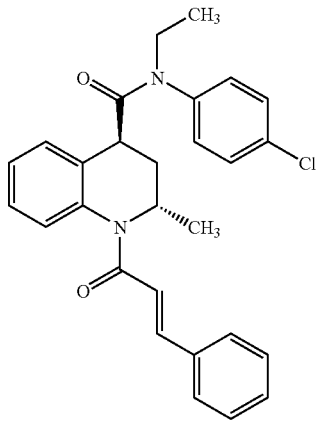
196
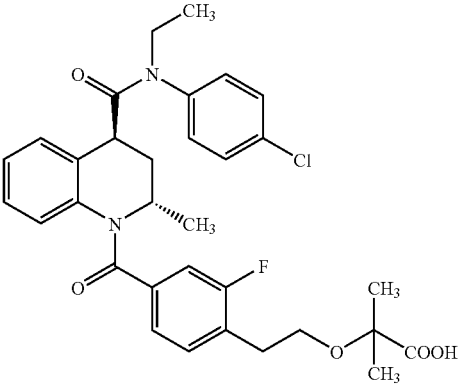
199
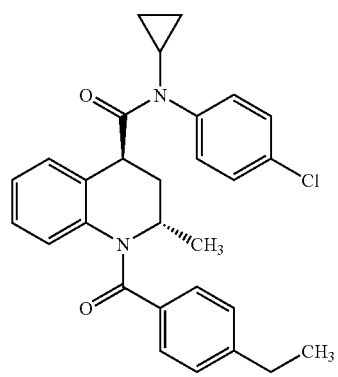
197
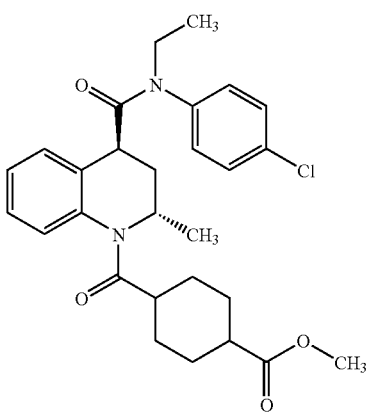
200
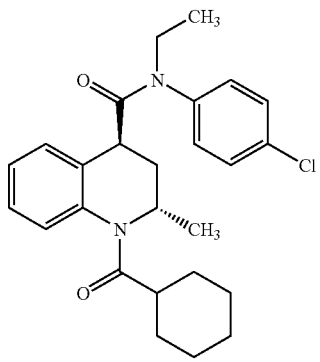
198
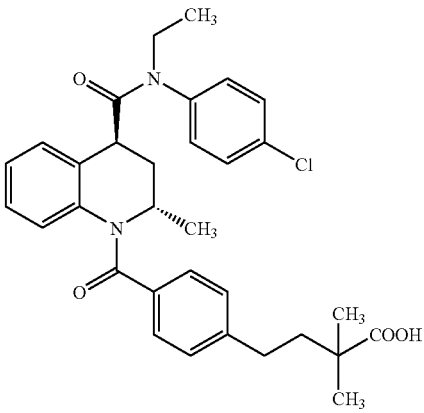
201

TABLE 1-continued

Examples of formula I compounds

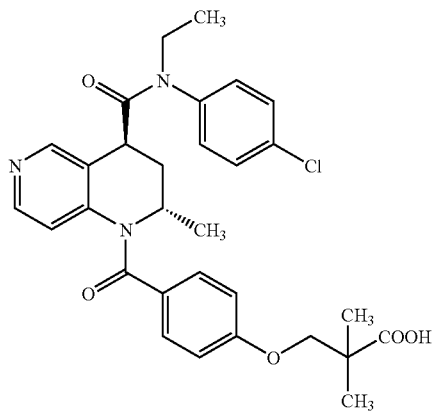

202

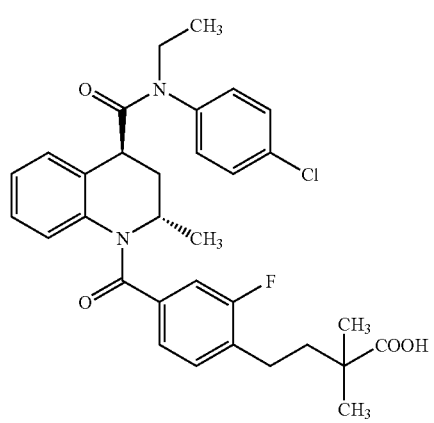

203

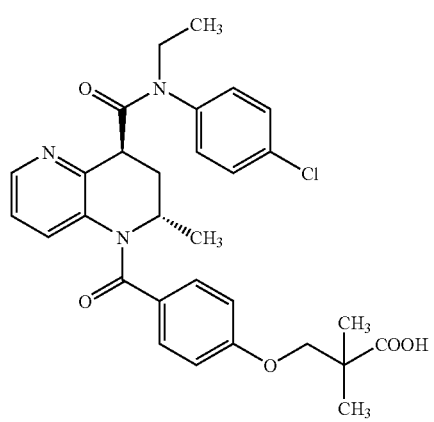

204

TABLE 1-continued

Examples of formula I compounds

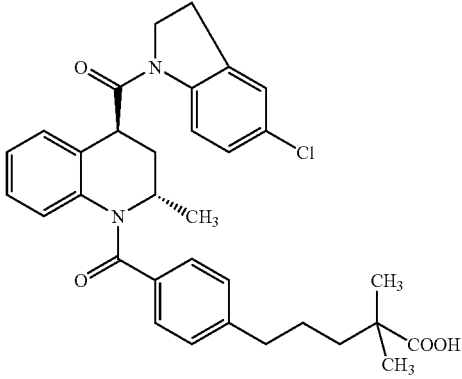

205

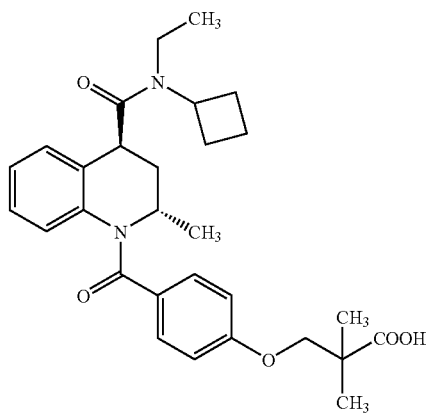

206

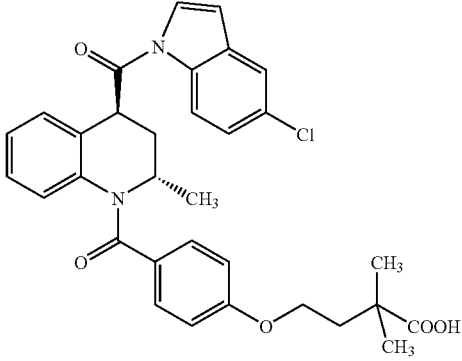

207

4. Uses, Formulation and Administration

As discussed above, the present invention provides compounds that are useful as inhibitors of CRTH2, and thus compounds of the invention are useful for treating (therapeutically or prophylactically) disorders with an inflammatory component and allergic conditions. Compounds of the invention can also be used to treat inflammatory disorders and allergic conditions mediated by Th2 cells, eosinophils, and basophils.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, a method for the treatment of an inflammatory disease or a disease with an inflammatory component is provided comprising administering an effective amount of a compound, or a pharmaceutical composition thereof to a subject in need thereof. Compounds and compositions of the invention are inhibitors of CRTH2, and thus, without wishing to be bound by any particular theory, the compounds and compositions are particularly useful for treating or lessening the severity of a disease, condition, or disorder where activation of one or more of CRTH2, PGD2 (including DP activity), Th2 cells, eosinophils, and/or basophils is implicated in the disease, condition, or disorder. When activation of one or more of CRTH2, PGD2 (including DP activity), Th2 cells, eosinophils, and/or basophils is implicated in a particular disease, condition, or disorder, the disease, condition, or disorder may also be referred to as a "CRTH2-mediated disease" or disease symptom. Accordingly, in another aspect, the present invention provides a method for treating or lessening the severity of a disease, condition, or disorder where activation of one or more of CRTH2, PGD2 (including DP activity), Th2 cells, eosinophils, and/or basophils is implicated in the disease state.

In certain embodiments of the present invention an "effective amount" of the compound or pharmaceutically acceptable composition is that amount effective for treating an inflammatory disease or disease with an inflammatory component. In other embodiments, an "effective amount" of a compound is an amount which inhibits binding of PGD2 to its receptor CRTH2 and thereby inhibits one or more processes mediated by the binding in a subject, for example, the release of proinflammatory mediators. An "effective amount" of a compound can achieve a desired therapeutic and/or prophylactic effect, such as an amount which results in the prevention of or a decrease in the symptoms associated with an inflammatory disease or a disease mediated by one or more of CRTH2, PGD2 (including DP activity), Th2 cells, eosinophils, and basophils.

In one embodiment, the inflammatory disease is an allergic condition. Examples of allergic conditions for which the disclosed compounds, pharmaceutical compositions and methods are believed to be particularly effective include atopic dermatitis, allergic rhinitis, rheumatoid arthritis, chronic obstructive pulmonary disorder (COPD), COPD exacerbations, or allergic asthma. Other allergic conditions include systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are believed to be particularly effective include osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CRTH2.

Diseases characterized by repurfusion have an inflammatory component that is believed to be mediated, at least in part by, by CRTH2. Examples include stroke, cardiac ischemia, and the like. The disclosed compounds and compositions also can be used to treat these disorders.

Other diseases and conditions with an inflammatory component believed to be mediated by CRTH2 include mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases and sarcoidosis. Yet other diseases or conditions with inflammatory components which are amendable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

In a preferred embodiment, the invention provides a method of treating asthma comprising administering an effective amount of a compound of general formula I (and subsets thereof as described herein) to a subject in need thereof.

The compounds and compositions, according to the method of the present invention, may be administered using any amount and any route of administration effective for treating an inflammatory disease or allergic condition. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

For example, compounds of the invention can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNδ-1b)) and the like.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting CRTH2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CRTH2 activity in a biological sample is useful for a variety of purposes that are known to one of skill in the art. Examples of such purposes include, but are not limited to, blood transfusion, organ-transplantation, biological specimen storage, and biological assays.

Experimental Procedures

General. All reactions involving air-sensitive reagents were performed under a nitrogen atmosphere. Reagents were used as received from commercial suppliers unless otherwise noted. $^1$H NMR data were recorded using the Bruker UltraShield 300 MHz/54 mm instrument equipped with Bruker B-ACS60 Auto Sampler or the Varian 300 MHz instrument. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. ISCO combi-flash chromatography instrument. LC/MS spectra were obtained using a MicroMass Platform LC (Phenomenx C18 column, 5 micron, 50×4.6 mm) equipped with a Gilson 215 Liquid Handler. Standard LC/MS conditions are as follows:

| | |
|---|---|
| % A (Water) | 95.0 |
| % B (Acetonitrile) | 5.0 |
| % Ammonium acetate | 0.1 |
| Flow (ml/min) | 2.500 |
| Stop Time (mins) | 3.8 |
| Min Pressure (bar) | 0 |
| Max Pressure (bar) | 400 |

-continued

| | |
|---|---|
| Oven Temperature Left(° C.) | 10.0 |
| Oven Temperature Right(° C.) | 10.0 |

HP1100 LC Pump Gradient Timetable
The gradient Timetable contains 4 entries which are:

| Time | A % | B % | C % | D % | Flow | Pressure |
|---|---|---|---|---|---|---|
| 0.00 | 95.0 | 5.0 | 0.0 | 0.0 | 2.500 | 400 |
| 2.00 | 0.0 | 100.0 | 0.0 | 0.0 | 2.500 | 400 |
| 3.00 | 0.0 | 100.0 | 0.0 | 0.0 | 2.500 | 400 |
| 3.05 | 95.0 | 5.0 | 0.0 | 0.0 | 2.000 | 400 |

LC-MS data were acquired using the "Ammonium acetate-standard" method unless otherwise noted.

Synthesis of (±)-cis-2-methyl-1,2,3,4-tetrahydroquinoline-4-carboxylic acid methyl ester

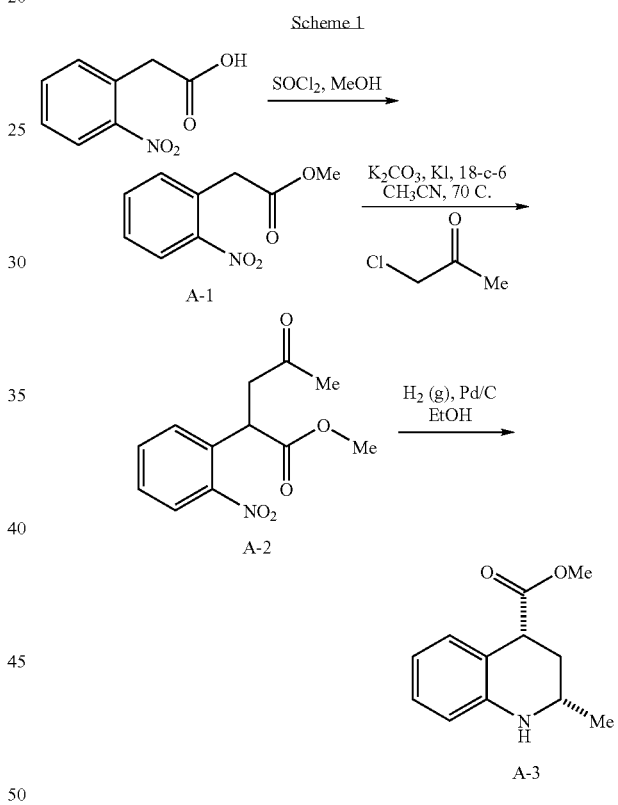

A round bottom flask with magnetic stirrer was charged with (2-nitro-phenyl)-acetic acid (10.0 g, 55.0 mmol) and methanol (70 mL) under an argon atmosphere. To the resulting yellow solution at room temperature was added thionyl chloride (12.1 mL, 166 mmol) dropwise via addition funnel (Note: Reaction is very exothermic). The resulting reaction mixture was stirred at room temperature for 12-18 hours and concentrated in vacuo to afford 13.3 g of crude (2-nitro-phenyl)-acetic acid methyl ester as an orange oil. This material was used directly in subsequent reactions.

A three-neck round bottom flask with magnetic stirrer was charged with crude (2-nitro-phenyl)-acetic acid methyl ester (7.23 g, 37.0 mmol), potassium carbonate (46.1 g, 33.3 mmol), 18-crown-6 (0.650 g), and potassium iodide (0.650 g) under an argon atmosphere. To the flask was added acetonitrile (80 mL) and the mixture heated at 70° C. for one hour. To the reaction was added chloroacetone (3.50 mL, 44.0 mmol) and the reaction stirred at 70° C. under argon for 18-20 hours. The reaction was cooled to room temperature and filtered through a pad of celite. The resulting filtrate was concentrated in vacuo to afford 9.64 g of crude material. Purification via flash chromatography (0-40% ethyl acetate/hexanes eluent) yielded 4.74 g of 2-(2-nitro-phenyl)-4-oxo-pentanoic acid methyl ester (51%).

A round bottom flask with magnetic stirrer was charged with 2-(2-nitro-phenyl)-4-oxo-pentanoic acid methyl ester (4.74 g, 19.1 mmol) and anhydrous ethanol (50 mL). To the reaction was added 10% palladium on carbon (0.948 g, 20% by weight) and the reaction stirred at room temperature under a hydrogen gas atmosphere (balloon) for 18-20 hours. The reaction was filtered through a pad of celite and the celite pad washed with warm ethanol. The combined filtrates were concentrated in vacuo to afford an off-white colored solid. This material was purified via Isco flash system (0-20% ethyl acetate/hexanes) to yield 2.64 g of cis-2-methyl-1,2,3,4-tetrahydro-quinoline-4-carboxylic acid methyl ester as a white solid (68%). $^1$H-NMR (CDCl$_3$) δ: 1.23 (3H, d), 1.95 (1H, dd), 2.10-2.18 (1H, m), 3.34-3.46 (1H, m), 3.74 (3H, s), 3.94 (1H, dd), 6.51 (1H, dd), 6.60-6.67 (1H, m), 6.94-7.03 (2H, m). MS m/z: 206 (M+1).

General Procedure A

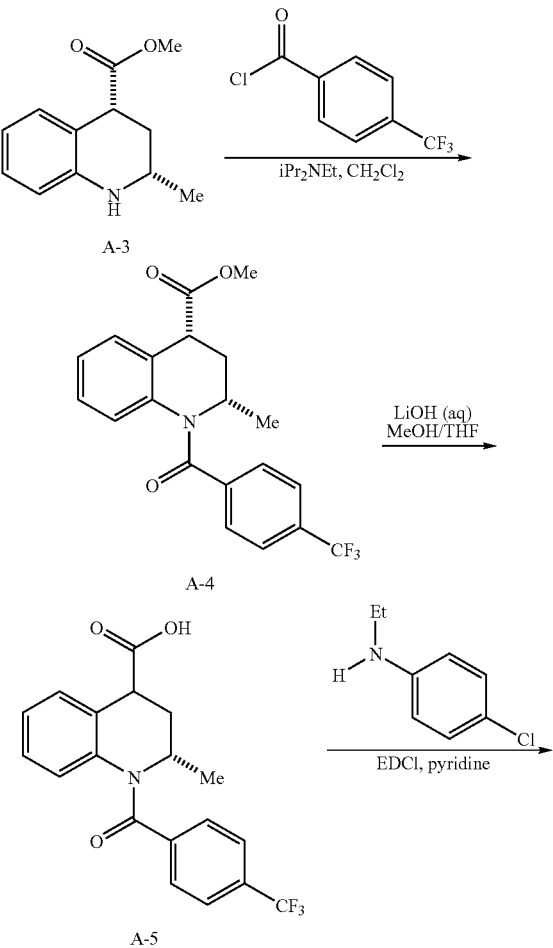

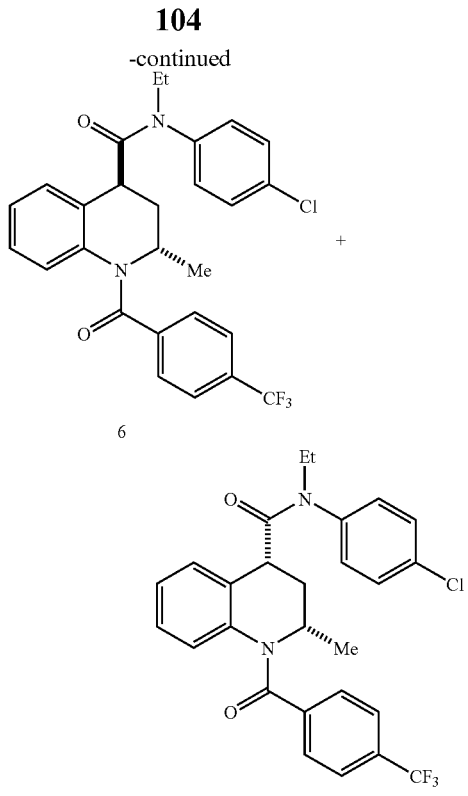

(±)-trans-2-Methyl-1-(4-trifluoromethyl-benzoyl)-1,2,3,4-tetrahydro-quinoline-4-carboxylic acid (4-chloro-phenyl)-ethyl-amide (6)

A round bottom flask with magnetic stirrer was charged with cis-2-methyl-1,2,3,4-tetrahydro-quinoline-4-carboxylic acid methyl ester (556 mg, 2.71 mmol) in methylene chloride (8.00 mL) under an argon atmosphere. Into the reaction was added 4-trifluoromethyl-benzoyl chloride (0.61 mL, 4.07 mmol) and N,N-diisopropylethylamine (1.20 mL, 6.89 mmol). The reaction was stirred at room temperature for 18-20 hours. The reaction was transferred to a separatory funnel containing a saturated sodium bicarbonate solution (15 mL), then diluted with methylene chloride (15 mL) and shaken vigorously. The resulting organic layer was separated, washed with brine (1×20 mL), dried over magnesium sulfate, and filtered. The filtrate was concentrated in vacuo to afford an orange residue (1.359 g). The residue was purified via flash chromatography (20% ethyl acetate/hexanes eluent) to yield cis-2-methyl-1-(4-trifluoromethyl-benzoyl)-1,2,3,4-tetrahydro-quinoline-4-carboxylic acid methyl ester as a tan-colored solid (990 mg, 97%).

A round bottom flask with magnetic stirrer was charged with cis-2-methyl-1-(4-trifluoromethyl-benzoyl)-1,2,3,4-tetrahydro-quinoline-4-carboxylic acid methyl ester (980 mg, 2.60 mmol) in tetrahydrofuran (10.0 mL). To the reaction was added a solution of lithium hydroxide (179 mg, 7.47 mmol) in water (10 mL), followed by methanol (10 mL). The reaction was stirred at room temperature for 18-20 hours under an argon atmosphere. The reaction was transferred to a separatory funnel and the pH adjusted to 2 via addition of 1N hydrochloric acid. The mixture was extracted with ethyl acetate (3×35 mL) and the combined extractions were washed with brine (1×50 mL), dried over magnesium sulfate, and filtered. The filtrate was concentrated in vacuo to yield 2-methyl-1-(4-trifluoromethyl-benzoyl)-1,2,3,4-tetrahydro-quinoline-4-carboxylic acid (mixture of cis and trans isomers) as an off-white solid (912 mg, 97%). The mixture was used without purification in subsequent reactions.

A round bottom flask with magnetic stirrer was charged with 2-methyl-1-(4-trifluoromethyl-benzoyl)-1,2,3,4-tetrahydro-quinoline-4-carboxylic acid (886 mg, 2.44 mmol) in anhydrous pyridine (25.0 mL). To the reaction was added N-ethyl-p-chloroaniline (0.410 mL, 2.95 mmol), followed by EDCI (833 mg, 4.34 mmol). The reaction was stirred at room temperature under an argon atmosphere for 18-20 hours. The reaction was poured into a 1:1 mixture of water/brine (50 mL) and extracted with ethyl acetate (3×35 mL). The combined extractions were washed with brine (1×50 mL), dried over magnesium sulfate, and filtered. The filtrate was concentrated in vacuo to afford a brown residue. The residue was purified via silica gel chromatography (hexanes/ethyl acetate) to yield (±)-trans-2-methyl-1-(4-trifluoromethyl-benzoyl)-1,2,3,4-tetrahydro-quinoline-4-carboxylic acid (4-chloro-phenyl)-ethyl-amide (39%). $^1$H-NMR (CDCl$_3$) δ: 1.02 (d, 3H), 1.12 (t, 3H), 1.64-1.74 (m, 1H), 2.49-2.58 (m, 1H), 3.59-3.72 (m, 1H), 3.77-3.90 (m, 2H), 5.03-5.14 (m, 1H), 6.35-6.41 (m, 1H), 6.74-6.84 (m, 2H), 6.89-6.95 (m, 1H), 7.17-7.25 (m, 2H), 7.44-7.52 (m, 2H), 7.63-7.69 (m, 2H). MS m/z: 501 (M+1).

General Procedure B

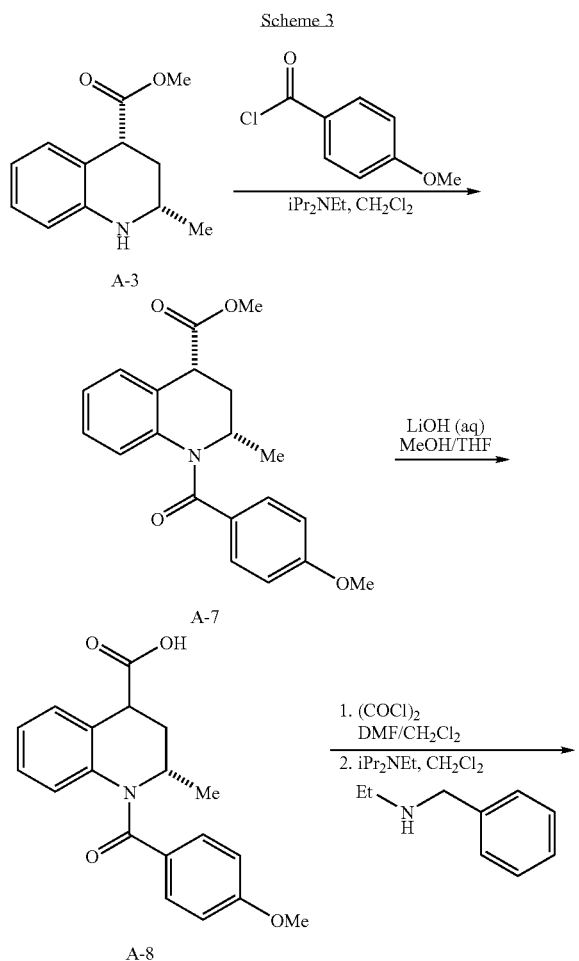

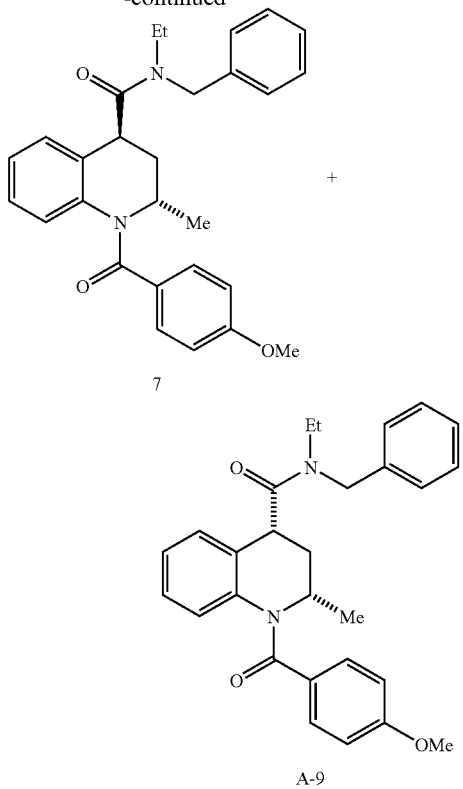

(±)-trans-1-(4-Methoxy-benzoyl)-2-methyl-1,2,3,4-tetrahydro-quinoline-4-carboxylic acid benzyl-ethyl-amide (7)

A round bottom flask with magnetic stirrer was charged with cis-2-methyl-1,2,3,4-tetrahydro-quinoline-4-carboxylic acid methyl ester (5.42 g, 26 mmol) in dichloromethane (100 mL) under an argon atmosphere at room temperature. To the reaction was added N,N-diisopropylethylamine (11.8 mL, 68 mmol), followed by p-anisoyl chloride (6.31 g, 37 mmol). The reaction was stirred at room temperature for 18-20 hours and poured into saturated sodium bicarbonate (1000 mL), diluted with dichloromethane (50 mL), and shaken vigorously. The resulting organic layer was separated, washed with brine (1×100 mL), dried over magnesium sulfate, and filtered. The filtrate was concentrated in vacuo to afford an oily residue. Diethyl ether (50 mL) was added to the residue and the resulting white solid was collected via suction filtration to afford cis-1-(4-methoxy-benzoyl)-2-methyl-1,2,3,4-tetrahydro-quinoline-4-carboxylic acid methyl ester (6.94 g, 78%).

A round bottom flask with magnetic stirrer was charged with cis-1-(4-methoxy-benzoyl)-2-methyl-1,2,3,4-tetrahydro-quinoline-4-carboxylic acid methyl ester (3.00 g, 8.8 mmol) in anhydrous tetrahydrofuran (70 mL). To the reaction was added a solution of lithium hydroxide (423 mg, 18 mmol) in water (24 mL), followed by methanol (24 mL). The reaction was stirred at room temperature for 18-20 hours under an argon atmosphere. The reaction was transferred to a separatory funnel and the pH adjusted to 2 via addition of 1N hydrochloric acid. The mixture was extracted with ethyl acetate (3×35 mL) and the combined extractions were washed with brine (1×50 mL), dried over magnesium sulfate, and filtered. The filtrate was concentrated in vacuo and diethyl ether (50 mL) added to the resulting residue. The precipitated solid was collected via suction filtration to afford 1-(4-methoxy-benzoyl)-2-methyl-1,2,3,4-tetrahydro-quinoline-4-carboxylic acid as a mixture of cis and trans-isomers (2.71 g, 95%). $^1$H-NMR (d$_6$-DMSO) δ: 1.22 (d, 3H), 1.63 (ddd, 1H), 2.94 (ddd, 1H), 3.76 (s, 3H), 3.89 (dd, 1H), 4.83-4.91 (m, 1H), 6.51 (d, 1H), 6.72-6.76 (m, 2H), 6.95 (ddd, 1H), 7.11 (ddd, 1H), 7.26-7.35 (m, 3H). MS m/z=326 (M+1).

1-(4-Methoxy-benzoyl)-2-methyl-1,2,3,4-tetrahydroquinoline-4-carboxylic acid (2.00 g, 6.15 mmol) was suspended in methylene chloride (50 mL). One drop of dimethylformamide was added, followed by oxalyl chloride (1.56 g, 1.07 mL, 12.3 mmol). The suspension became homogeneous on stirring. After 2 hours, the yellow solution was concentrated under reduced pressure and azeotroped with toluene. To a solution of the resulting acid chloride (120 mg, 349 mmol) in methylene chloride (1 mL) was added diisopropylethylamine (451 uL, 0.349 mmol), followed by ethyl-benzylamine (71 mg, 77 uL, 0.523 mmol). The mixture was shaken overnight at room temperature. Upon completion, the reaction was diluted with ethyl acetate, washed with saturated sodium bicarbonate (aqueous) and brine, dried over sodium sulfate, filtered and concentrated to afford the crude amide. Purification by silica gel chromatography (elution with a hexane/ethyl acetate gradient) afforded pure (±)-trans-1-(4-methoxy-benzoyl)-2-methyl-1,2,3,4-tetrahydro-quinoline-4-carboxylic acid benzyl-ethyl-amide (53 mg, 34%). $^1$H-NMR (CDCl$_3$) δ: 0.98 (d, 3H), 1.13 (t, 3H), 1.74 (ddd, 1H), 2.52 (ddd, 1H), 3.62-3.92 (m, 8H), 5.03-5.13 (m, 1H), 6.44 (d, 1H), 6.72-6.84 (m, 4H), 6.86-6.92 (m, 1H), 7.19-7.23 (m, 2H), 7.43-7.54 (m, 4H). MS m/z: 443 (M+1).

(±)-trans-1-(4-Methoxy-benzoyl)-2-methyl-1,2,3,4-tetrahydro-quinoline-4-carboxylic acid ethyl-(4-trifluoromethyl-phenyl)-amide (1)

(±)-trans-1-(4-Methoxy-benzoyl)-2-methyl-1,2,3,4-tetrahydro-quinoline-4-carboxylic acid ethyl-(4-trifluoromethyl-phenyl)-amide was made following general procedure B, substituting ethyl-(4-trifluoromethyl-phenyl)-amine for ethyl-benzyl-amine. The crude 1-(4-methoxy-benzoyl)-2-methyl-1,2,3,4-tetrahydro-quinoline-4-carboxylic acid ethyl-(4-trifluoromethyl-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-trifluoromethyl-phenyl)-amide. $^1$H-NMR (CDCl$_3$) δ: 0.99 (d, 3H), 1.15 (t, 3H), 1.71-1.79 (m, 1H), 2.53-2.62 (m, 1H), 3.69-4.00 (m, 6H), 5.06-5.12 (m, 1H), 6.47 (d, 1H), 6.74-6.91 (m, 5H), 7.41 (d, 2H), 7.51 (d, 2H), 7.77 (d, 2H). MS m/z: 497 (M$^+$).

(±)-trans-1-[2-(4-Methoxy-phenyl)-acetyl]-2-methyl-1,2,3,4-tetrahydro-quinoline-4-carboxylic acid (4-chloro-phenyl)-ethyl-amide (2)

(±)-trans-1-[2-(4-Methoxy-phenyl)-acetyl]-2-methyl-1,2,3,4-tetrahydro-quinoline-4-carboxylic acid (4-chloro-phenyl)-ethyl-amide was made following general procedure A, substituting 4-methoxyphenylacetyl chloride for 4-trifluoromethyl-benzoyl chloride. The crude 1-[2-(4-methoxy-phenyl)-acetyl]-2-methyl-1,2,3,4-tetrahydro-quinoline-4-carboxylic acid (4-chloro-phenyl)-ethyl-amide was isolated as a mixture of cis and trans isomers. Purification by flash chromatography (dichloromethane/methanol gradient: 99/1 to 98/2) yielded (±)-trans-1-[2-(4-methoxy-phenyl)-acetyl]-2-methyl-1,2,3,4-tetrahydro-quinoline-4-carboxylic acid (4-chloro-phenyl)-ethyl-amide (24%). $^1$H-NMR (CDCl$_3$) δ: 0.96 (d, 3H), 1.13 (t, 3H), 1.40-1.50 (m, 1H), 2.45-2.56 (m, 1H), 3.60-3.70 (m, 1H), 3.75 (q, 2H), 3.80 (s, 2H), 3.82 (s, 3H), 4.98-5.10 (m, 1H), 6.70 (d, 1H), 6.90 (d, 2H), 7.00-7.23 (m, 5H), 7.30 (m, 2H), 7.45 (d, 2H). MS m/z: 477/479 (M+1).

(±)-trans-2-Methyl-1-(pyrimidine-5-carbonyl)-1,2,3,4-tetrahydro-quinoline-4-carboxylic acid (4-chlorophenyl)-ethyl-amide (3)

(±)-trans-2-Methyl-1-(pyrimidine-5-carbonyl)-1,2,3,4-tetrahydro-quinoline-4-carboxylic acid (4-chloro-phenyl)-ethyl-amide was made following general procedure A, substituting pyrimidine-5-carbonyl chloride for 4-trifluoromethyl-benzoyl chloride. Pyrimidine-5-carbonyl chloride was prepared by reaction of pyrimidine-5-carboxylic acid with oxalyl chloride and dimethylformamide in methylene chloride. The crude 2-methyl-1-(pyrimidine-5-carbonyl)-1,2,3,4-tetrahydro-quinoline-4-carboxylic acid (4-chloro-phenyl)ethyl-amide was isolated as a mixture of cis and trans isomers. Purification by silica gel chromatography (2% methanol/methylene chloride) yielded (±)-trans-2-methyl-1-(pyrimidine-5-carbonyl)-1,2,3,4-tetrahydro-quinoline-4-carboxylic acid (4-chloro-phenyl)-ethyl-amide (44%). $^1$H-NMR (CDCl$_3$) δ: 1.02-1.18 (m, 6H), 1.65-1.75 (m, 1H), 2.50-2.60 (m, 1H), 3.60-3.70 (m, 1H), 3.80 (q, 2H), 4.98-5.10 (m, 1H), 6.40 (d, 1H), 6.70 (d, 1H), 6.90-7.00 (m, 2H), 7.20 (d, 2H), 7.50 (d, 2H), 8.85 (s, 2H), 9.15 (s, 1H). MS m/z: 435/437 (M+1).

(±)-trans-4-{Ethyl-[1-(4-methoxy-benzoyl)-2-methyl-1,2,3,4-tetrahydro-quinoline-4-carbonyl]-amino}-benzoic acid methyl ester (4)

(±)-trans-4-{Ethyl-[1-(4-methoxy-benzoyl)-2-methyl-1,2,3,4-tetrahydro-quinoline-4-carbonyl]-amino}-benzoic acid methyl ester was made following general procedure B, substituting 4-ethylamino-benzoic acid methyl ester for ethyl-benzyl-amine. The crude 4-{ethyl-[1-(4-methoxy-benzoyl)-2-methyl-1,2,3,4-tetrahydro-quinoline-4-carbonyl]-amino}-benzoic acid methyl ester was isolated as a mixture of cis and trans isomers. Purification via HPLC yielded (±)-trans-4-{ethyl-[1-(4-methoxy-benzoyl)-2-methyl-1,2,3,4-tetrahydro-quinoline-4-carbonyl]-amino}-benzoic acid methyl ester. $^1$H-NMR (CDCl$_3$) δ: 0.97 (d, 3H), 1.19 (t, 3H), 1.72-1.81 (m, 1H), 2.52-2.61 (m, 1H), 3.71-3.78 (m, 4H), 3.89-3.93 (m, 2H), 3.97 (s, 3H), 5.06-5.12 (m, 1H), 6.60 (d, 1H), 6.75-6.90 (m, 5H), 7.36 (d, 2H), 7.51 (d, 2H), 7.87 (d, 2H). MS m/z: 487 (M$^+$), 459.

(±)-trans-1-(4-Methoxy-benzoyl)-2-methyl-1,2,3,4-tetrahydro-quinoline-4-carboxylic acid (4-chlorobenzyl)-ethyl-amide (5)

(±)-trans-1-(4-Methoxy-benzoyl)-2-methyl-1,2,3,4-tetrahydro-quinoline-4-carboxylic acid (4-chloro-benzyl)-ethyl-amide was made following general procedure B, substituting N-ethyl-4-chlorobenzylamine for ethyl-benzyl-amine. $^1$H-NMR (CDCl$_3$, mixture of rotamers) δ: 1.07-1.28 (m, 6H), 1.83 (ddd, 0.4H), 2.03 (ddd, 0.6H), 2.42-2.64 (m, 1H), 3.39-3.52 (m, 2H), 3.75 (s, 3H), 4.07-4.28 (m, 1H), 4.50-4.72 (m, 2H), 4.99-5.20 (m, 1H), 6.49-7.53 (m, 12H). MS m/z: 381 (M+1).

(±)-trans-1-(4-Methoxy-benzoyl)-2-methyl-1,2,3,4-tetrahydro-quinoline-4-carboxylic acid benzylamide (8)

(±)-trans-1-(4-Methoxy-benzoyl)-2-methyl-1,2,3,4-tetrahydro-quinoline-4-carboxylic acid benzylamide was made following general procedure B, substituting benzylamine for ethyl-benzyl-amine. The crude product was isolated as a mixture of cis and trans isomers. Purification by HPLC yielded (±)-trans-1-(4-methoxy-benzoyl)-2-methyl-1,2,3,4-tetrahydro-quinoline-4-carboxylic acid benzylamide. $^1$H-NMR (CDCl$_3$) δ: 1.20 (d, 3H), 1.81 (ddd, 1H), 2.75-2.86 (m, 1H), 3.70-3.78 (m, 4H), 4.34-4.40 (m, 2H), 4.79-4.88 (m, 1H), 5.85-5.94 (m, 1H), 6.61-6.67 (m, 2H), 6.75 (d, 1H), 6.97-7.16 (m, 5H), 7.18-7.24 (m, 5H). MS m/z=415 (M+1).

(±)-trans-4-(4-{4-[(4-Chloro-phenyl)-ethyl-carbamoyl]-2-methyl-3,4-dihydro-2H-quinoline-1-carbonyl}-phenoxy)-butyric acid ethyl ester (9) and (±)-cis-4-(4-{4-[(4-chloro-phenyl)-ethyl-carbamoyl]-2-methyl-3,4-dihydro-2H-quinoline-1-carbonyl}-phenoxy)-butyric acid ethyl ester (10)

(±)-trans-1-(4-Hydroxy-benzoyl)-2-methyl-1,2,3,4-tetrahydro-quinoline-4-carboxylic acid (4-chloro-phenyl)-ethyl-amide (585 mg, 1.30 mmol) was dissolved in dimethylformamide (20 mL). Potassium carbonate (1.5 g) was added, followed by ethyl-4-bromobutyrate (2.53 g, 1.9 mL, 13 mmol). The reaction was warmed to 90° C. and stirred under nitrogen overnight. Upon completion, the reaction was cooled to room temperature. The solvent layer was decanted and concentrated. The residue was dissolved in ethyl acetate. The residual solids in the reaction flask were washed with ethyl acetate and the washings combined with the filtrate ethyl acetate solution. The combined ethyl acetate layers were washed with water (3×) and brine, dried over sodium sulfate, filtered, and concentrated to afford the crude product. The crude material was a mixture of cis and trans isomers due to racemization under the alkylation conditions. The mixture was purified by silica gel chromatography (ethyl acetate/hexanes gradient) to afford pure (±)-trans-4-(4-{4-[(4-chloro-phenyl)-ethyl-carbamoyl]-2-methyl-3,4-dihydro-2H-quinoline-1-carbonyl}-phenoxy)-butyric acid ethyl ester as a foam (88%) and pure (±)-cis-4-(4-{4-[(4-Chloro-phenyl)-ethyl-carbamoyl]-2-methyl-3,4-dihydro-2H-quinoline-1-carbonyl}-phenoxy)-butyric acid ethyl ester. Data for the trans isomer: $^1$H-NMR (CDCl$_3$) δ: 0.97 (d, 3H), 1.13 (t, 3H), 1.24 (t, 3H), 1.73 (ddd, 1H), 2.01-2.14 (m, 2H), 2.41-2.59 (m, 3H), 3.61-4.00 (m, 5H), 4.06-4.18 (m, 2H), 5.01-5.14 (m, 1H), 6.44 (d, 1H), 6.68-6.84 (m, 4H), 6.89 (dd, 1H), 7.16-7.27 (m, 2H), 7.42-7.51 (m, 4H). MS m/z: 563 (M+1).

(±)-trans-1-(4-Methoxy-benzoyl)-2-methyl-1,2,3,4-tetrahydro-quinoline-4-carboxylic acid (4-chloro-3-trifluoromethyl-phenyl)-ethyl-amide (11)

(±)-trans-1-(4-Methoxy-benzoyl)-2-methyl-1,2,3,4-tetrahydro-quinoline-4-carboxylic acid (4-chloro-3-trifluoromethyl-phenyl)-ethyl-amide was made following general procedure B, substituting ethyl-(4-chloro-3-trifluoromethyl-phenyl)-amine for ethyl-benzyl-amine. The crude 1-(4-methoxy-benzoyl)-2-methyl-1,2,3,4-tetrahydro-quinoline-4-carboxylic acid (4-chloro-3-trifluoromethyl-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (4-chloro-3-trifluoromethyl-phenyl)-ethyl-amide. $^1$H-NMR (CDCl$_3$) δ: 1.02 (d, 3H), 1.13 (t, 3H), 1.64-1.72 (m, 1H), 2.58-2.67 (m, 1H), 3.59-3.69 (m, 1H), 3.76 (s, 3H), 3.85-3.97 (m, 2H), 5.02-5.12 (m, 1H), 6.49 (d, 1H), 6.60-6.62 (m, 1H), 6.75 (d, 2H), 6.80-6.89 (m, 2H), 7.39 (dd, 1H), 7.46-7.51 (m, 3H), 7.64 (d, 1H). MS m/z: 531 (M+1), 533 (M+2).

(±)-trans-1-(4-Methoxy-benzoyl)-2-methyl-1,2,3,4-tetrahydro-quinoline-4-carboxylic acid ethyl-m-tolyl-amide (12)

(±)-trans-1-(4-Methoxy-benzoyl)-2-methyl-1,2,3,4-tetrahydro-quinoline-4-carboxylic acid ethyl-m-tolyl-amide was made following general procedure B, substituting ethyl-m-tolyl-amine for ethyl-benzyl-amine. The crude 1-(4-methoxy-benzoyl)-2-methyl-1,2,3,4-tetrahydro-quinoline-4-carboxylic acid ethyl-m-tolyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-m-tolyl-amide. $^1$H-NMR (CDCl$_3$) δ: 0.96 (d, 3H), 1.15 (t, 3H), 1.74-1.82 (m, 1H), 2.53 (s, 3H), 2.50-2.59 (m, 1H), 3.68-3.77 (m, 4H), 3.85-3.91 (m, 2H), 5.07-5.13 (m, 1H), 6.44 (d, 1H), 6.78-6.93 (m, 5H), 7.08 (bs, 2H), 7.22 (d, 2H), 7.51-7.54 (m, 2H). MS m/z: 444 (M+1).

(±)-trans-4-(4-{4-[(4-Chloro-phenyl)-ethyl-carbamoyl]-2-methyl-3,4-dihydro-2H-quinoline-1-carbonyl}-phenoxy)-2,2-dimethyl-acetic acid (13) and (±)-cis-4-(4-{4-[(4-Chloro-phenyl)-ethyl-carbamoyl]-2-methyl-3,4-dihydro-2H-quinoline-1-carbonyl}-phenoxy)-2,2-dimethyl-acetic acid (39)

(±)-trans-4-(4-{4-[(4-Chloro-phenyl)-ethyl-carbamoyl]-2-methyl-3,4-dihydro-2H-quinoline-1-carbonyl}-phenoxy)-2,2-dimethyl-acetic acid was made following the procedures for the synthesis of (±)-trans-4-(4-{4-[(4-chloro-phenyl)-ethyl-carbamoyl]-2-methyl-3,4-dihydro-2H-quinoline-1-carbonyl}-phenoxy)-butyric acid from (±)-trans-1-(4-hydroxy-benzoyl)-2-methyl-1,2,3,4-tetrahydro-quinoline-4-carboxylic acid (4-chloro-phenyl)-ethyl-amide. Ethyl-2-bromoisobutyrate was substituted for ethyl-4-bromobutyrate. $^1$H-NMR (CDCl$_3$) δ: 0.97 (d, 3H), 1.12 (t, 3H), 1.54 (s, 3H), 1.56 (s, 3H), 1.67-1.75 (m, 1H), 2.47-2.58 (m, 1H), 3.57-3.73 (m, 1H), 3.76-3.90 (m, 2H), 5.06-5.11 (m, 1H), 6.42 (d, 1H), 6.73-6.92 (m, 5H), 7.19-7.28 (m, 2H), 7.46 (d, 4H). Cis: $^1$H-NMR (CDCl$_3$) δ: 1.15 (d, 3H), 1.24 (t, 3H), 1.53 (s, 3H), 1.55 (s, 3H), 1.63-1.76 (m, 1H), 2.47-2.58 (m, 1H), 3.29-3.34 (m, 1H), 3.74-3.87 (m, 1H), 3.97-4.14 (m, 1H), 6.38 (d, 1H), 6.56-6.61 (m, 2H), 6.85-6.96 (t, 1H), 7.07-7.21 (m, 5H), 7.32 (d, 3H). MS m/z: 536 (M+1).

(±)-cis and (±)-trans-1-(4-Methoxy-benzoyl)-2,4-dimethyl-1,2,3,4-tetrahydro-quinoline-4-carboxylic acid (4-chloro-phenyl)-ethyl-amide (14)

A round bottom flask was charged with 1-(4-methoxy-benzoyl)-2-methyl-1,2,3,4-tetrahydro-quinoline-4-carboxylic acid (4-chloro-phenyl)-ethyl-amide in anhydrous THF (10.0 ml) under an argon atmosphere. Into the reaction was added lithium hexamethyldisilazide (2.10 mL of a 1M THF solution) via syringe. The reaction was stirred at room temperature for 30 minutes. Next, methyl iodide (0.44 mL, 7.1 mmol) was added and the reaction stirred at room temperature for an additional 18 hours. The reaction mixture was diluted with water (10 mL), transferred to a separatory funnel, and extracted with ethyl acetate (3×30 mL). The combined organic layers were washed with brine (1×70 mL), dried over magnesium sulfate, and filtered. The filtrate was concentrated in vacuo to afford a mixture of (±)-cis and (±)-trans-1-(4-methoxy-benzoyl)-2,4-dimethyl-1,2,3,4-tetrahydro-quinoline-4-carboxylic acid (4-chloro-phenyl)-ethyl-amide as a yellow solid (309 mg) containing 1-(4-methoxy-benzoyl)-2- methyl-1,2,3,4-tetrahydro-quinoline-4-carboxylic acid (4-chloro-phenyl)-ethyl-amide. MS m/z: 477 (M+1).

(±)-trans-1-(4-Methoxy-benzoyl)-2-methyl-1,2,3,4-tetrahydro-quinoline-4-carboxylic acid ethyl-(4-isopropyl-phenyl)-amide (15)

(±)-trans-1-(4-Methoxy-benzoyl)-2-methyl-1,2,3,4-tetrahydro-quinoline-4-carboxylic acid ethyl-(4-isopropyl-phenyl)-amide was made following general procedure B, substituting ethyl-(4-isopropyl-phenyl)-amine for ethyl-benzyl-amine. The crude 1-(4-methoxy-benzoyl)-2-methyl-1,2,3,4-tetrahydro-quinoline-4-carboxylic acid ethyl-(4-isopropyl-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-isopropyl-phenyl)-amide. $^1$H-NMR (CDCl$_3$) δ: 0.96 (d, 3H), 1.15 (t, 3H), 1.28 (d, 6H), 1.72-1.81 (m, 1H), 2.50-2.59 (m, 1H), 2.92-3.01 (m, 1H), 3.64-3.73 (m, 1H), 3.75 (s, 3H), 3.81-3.93 (m, 2H), 5.04-5.14 (m, 1H), 6.43 (d, 1H), 6.69-6.91 (m, 5H), 7.17 (d, 2H), 7.32 (d, 2H), 7.52 (d, 2H). MS m/z: 471 (M$^+$), 472 (M+1).

(±)-cis-4-(4-{4-[(4-Chloro-phenyl)-ethyl-carbamoyl]-2-methyl-3,4-dihydro-2H-quinoline-1-carbonyl}-phenoxy)-butyric acid (16) and (±)-trans-4-(4-{4-[(4-chloro-phenyl)-ethyl-carbamoyl]-2-methyl-3,4-dihydro-2H-quinoline-1-carbonyl}-phenoxy)-butyric acid (19)

(±)-trans-4-(4-{4-[(4-Chloro-phenyl)-ethyl-carbamoyl]-2-methyl-3,4-dihydro-2H-quinoline-1-carbonyl}-phenoxy)-butyric acid ethyl ester (520 mg, 0.923 mmol) was dissolved in tetrahydrofuran (15 mL). A solution of lithium hydroxide (77 mg, 1.8 mmol) in water (5 mL) was added. Ethanol was added until the reaction was homogeneous. The resulting solution was allowed to stir at room temperature overnight. The solution was concentrated to remove ethanol and tetrahydrofuran. The resulting aqueous mixture was acidified with concentrated hydrochloric acid until pH=1-2. The heterogeneous mixture was immediately extracted with ethyl acetate (2×75 mL). The extracts were combined, washed with brine, dried over sodium sulfate, filtered, and concentrated. The residue was a mixture of cis and trans isomers. A portion of the crude residue was purified by HPLC to afford pure (±)-trans-4-(4-{4-[(4-chloro-phenyl)-ethyl-carbamoyl]-2-methyl-3,4-dihydro-2H-quinoline-1-carbonyl}-phenoxy)-butyric acid and pure (±)-cis-4-(4-{4-[(4-chloro-phenyl)-ethyl-carbamoyl]-2-methyl-3,4-dihydro-2H-quinoline-1-carbonyl}-phenoxy)-butyric acid. The remainder of the mixture was used without further purification in subsequent reactions. Data for the trans isomer: $^1$H-NMR (CD$_3$OD) δ: 0.97 (d, 3H), 1.12 (t, 3H), 4.73 (ddd, 1H), 2.00-2.13 (m, 2H), 2.47-2.58 (m, 3H), 3.61-3.99 (m, 5H), 5.02-5.12 (m, 1H), 6.44 (d, 1H), 6.68-6.74 (m, 2H), 6.75-6.83 (m, 2H), 6.85-6.92 (m, 1H), 7.17-7.25 (m, 3H), 7.42-7.51 (m, 4H). MS m/z: 535 (M+1).

(±)-trans-1-(4-Methoxy-benzoyl)-2-methyl-1,2,3,4-tetrahydro-quinoline-4-carboxylic acid ethyl-(4-nitro-phenyl)-amide (17)

(±)-trans-1-(4-Methoxy-benzoyl)-2-methyl-1,2,3,4-tetrahydro-quinoline-4-carboxylic acid ethyl-(4-nitro-phenyl)-amide was made following general procedure B, substituting ethyl-(4-nitro-phenyl)-amine for ethyl-benzyl-amine. The crude 1-(4-methoxy-benzoyl)-2-methyl-1,2,3,4-tetrahydro-quinoline-4-carboxylic acid ethyl-(4-nitro-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-nitro-phenyl)-amide. $^1$H-NMR (CDCl$_3$) δ: 0.96 (d, 3H), 1.15 (t, 3H), 1.75-1.83 (m, 1H), 2.48-2.57 (m, 1H), 3.65-3.77 (m, 4H), 3.83-3.90 (m, 2H), 5.05-5.15 (m, 1H), 6.43 (d, 1H), 6.74-6.81 (m, 3H), 6.88-6.91 (m, 2H), 7.15 (d, 2H), 7.26-7.29 (m, 2H), 7.52-7.55 (m, 2H). MS m/z: 474 (M+1).

(±)-trans-2-Methyl-1-(3-methyl-isoxazole-5-carbonyl)-1,2,3,4-tetrahydro-quinoline-4-carboxylic acid (4-chloro-phenyl)-ethyl-amide (18)

To a 0.5 M methanolic solution of sodium methoxide (48 mL, 24 mmol) was added a solution of nitroethane (1.7 mL, 24 mmol) in dimethylacetamide (18 mL) under a nitrogen atmosphere. After the mixture was cooled down to 5° C., acetyl chloride (1.7 mL, 24 mmol) and ethyl propionate (2.4 mL, 24 mmol) were added and the reaction mixture was stirred at room temperature for 20 hours. The reaction mixture was concentrated in vacuo and partitioned between water and ethyl acetate. The organic layer was separated and washed with brine, dried over magnesium sulfate, and concentrated in vacuo to yield an orange oil (3.7 g). The crude material was purified by flash chromatography (10% ethyl acetate/hexanes) to provide 3-methyl-isoxazole-5-carboxylic acid ethyl ester as white crystals (900 mg, 24%).

A round bottom flask with magnetic stirrer was charged with 3-methyl-isoxazole-5-carboxylic acid ethyl ester (900 mg, 5.8 mmol) in tetrahydrofuran (2.0 mL). To the reaction was added a solution of sodium hydroxide (465 mg, 11.6 mmol) in water (2 mL), followed by methanol (4 mL). The reaction was stirred at room temperature for 18-20 hours under an argon atmosphere. The reaction was transferred to a separatory funnel and the pH adjusted to 2 via addition of 1N hydrochloric acid. The mixture was extracted with ethyl acetate (3×35 mL) and the combined extractions were washed with brine (1×50 mL), dried over magnesium sulfate, and filtered. The filtrate was concentrated in vacuo to yield 3-methyl-isoxazole-5-carboxylic acid as a white solid (660 mg, 90%). The solid was used without purification in the next reaction.

(±)-trans-2-Methyl-1-(3-methyl-isoxazole-5-carbonyl)-1,2,3,4-tetrahydro-quinoline-4-carboxylic acid (4-chloro-phenyl)-ethyl-amide was made following general procedure A, substituting 3-methyl-isoxazole-5-carbonyl chloride for 4-trifluoromethyl-benzoyl chloride. 3-Methyl-isoxazole-5-carbonyl chloride was prepared by reaction of the preformed 3-methyl-isoxazole-5-carboxylic acid with oxalyl chloride and dimethylformamide in methylene chloride. In addition, only 1.2 equivalents of lithium hydroxide were used in the ester hydrolysis step. The crude 2-methyl-1-(3-methyl-isoxazole-5-carbonyl)-1,2,3,4-tetrahydro-quinoline-4-carboxylic acid (4-chloro-phenyl)-ethyl-amide was isolated as a mixture of cis and trans isomers. Purification by silica gel chromatography (dichloromethane/methanol gradient: 99.5/0.5->99/1) yielded (±)-trans-methyl-1-(3-methyl-isoxazole-5-carbonyl)-1,2,3,4-tetrahydro-quinoline-4-carboxylic acid (4-chloro-phenyl)-ethyl-amide (24%). $^1$H-NMR (CDCl$_3$) δ: 1.02 (t, 3H), 1.13 (d, 3H), 1.40-1.50 (m, 1H), 2.25 (s, 3H), 2.70-2.80 (m, 1H), 3.40-3.52 (m, 1H), 3.80 (q, 2H), 4.95-5.10 (m, 1H), 6.35 (d, 1H), 6.42 (s, 1H), 6.70 (d, 1H), 6.90 (t, 1H), 7.00 (t, 1H), 7.10 (d, 2H), 7.40 (d, 2H). MS m/z: 438/440 (M+1).

(±)-trans-1-(4-Methoxy-benzoyl)-2-methyl-1,2,3,4-tetrahydro-quinoline-4-carboxylic acid ethyl-(4-imidazol-1-yl-phenyl)-amide (20)

(±)-trans-1-(4-Methoxy-benzoyl)-2-methyl-1,2,3,4-tetrahydro-quinoline-4-carboxylic acid ethyl-(4-imidazol-1-yl-phenyl)-amide was made following general procedure B, substituting ethyl-(4-imidazol-1-yl-phenyl)-amine for ethyl-benzyl-amine. The crude 1-(4-methoxy-benzoyl)-2-methyl-1,2,3,4-tetrahydro-quinoline-4-carboxylic acid ethyl-(4-imidazol-1-yl-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-imidazol-1-yl-phenyl)-amide. $^1$H-NMR (CDCl$_3$) δ: 0.98 (d, 3H), 1.15 (t, 3H), 1.73-1.84 (m, 1H), 2.48-2.64 (m, 1H), 3.75 (bs, 4H), 3.84-3.98 (m, 2H), 5.00-5.15 (m, 1H), 6.45 (d, 1H), 6.73-6.89 (m, 5H), 7.24 (bs, 1H), 7.32-7.40 (m, 3H), 7.51 (bs, 4H), 7.91 (bs, 1H). MS m/z: 495 (M$^+$).

(±)-trans-1-(4-Methoxy-benzoyl)-2-methyl-1,2,3,4-tetrahydro-quinoline-4-carboxylic acid (4-chloro-phenyl)-amide (21)

(±)-trans-1-(4-Methoxy-benzoyl)-2-methyl-1,2,3,4-tetrahydro-quinoline-4-carboxylic acid (4-chloro-phenyl)-amide was prepared following general procedure B, substituting 4-chloroaniline for ethyl-benzyl-amine. $^1$H-NMR (CDCl$_3$) δ: 1.18 (d, 3H), 1.74-1.85 (m, 1H), 2.87 (ddd, 1H), 3.73 (s, 3H), 3.82 (dd, 1H), 4.83-4.95 (m, 1H), 6.61-6.67 (m, 2H), 6.76 (d, 1H), 6.99-7.13 (m, 2H), 7.14-7.21 (m, 2H), 7.25-7.31 (m, 3H), 7.36-7.43 (m, 2H), 7.87 (s, 1H). MS m/z: 435 (M+1).

(±)-trans-1-(4-Methoxy-benzoyl)-2-methyl-1,2,3,4-tetrahydro-quinoline-4-carboxylic acid (4-chloro-3-methyl-phenyl)-ethyl-amide (22)

(±)-trans-1-(4-Methoxy-benzoyl)-2-methyl-1,2,3,4-tetrahydro-quinoline-4-carboxylic acid (4-chloro-3-methyl-phenyl)-ethyl-amide was made following general procedure B, substituting ethyl-(4-chloro-3-methyl-phenyl)-amine for ethyl-benzyl-amine. The crude 1-(4-methoxy-benzoyl)-2-methyl-1,2,3,4-tetrahydro-quinoline-4-carboxylic acid (4-chloro-3-methyl-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (4-chloro-3-methyl-phenyl)-ethyl-amide. $^1$H-NMR (CDCl$_3$) δ: 0.99 (d, 3H), 1.14 (t, 3H), 1.72-1.80 (m, 1H), 2.44 (s, 3H), 2.50-2.59 (m, 1H), 3.62-3.73 (m, 1H), 3.77 (s, 3H), 3.79-3.92 (m, 2H), 5.07-5.13 (m, 1H), 6.45 (d, 1H), 6.74-6.83 (m, 4H), 6.88-6.93 (m, 1H), 7.04-7.06 (m, 1H), 7.13 (bs, 1H), 7.45 (d, 1H), 7.52 (d, 2H). MS m/z: 477 (M$^+$).

(±)-cis-1-(6-Methoxy-pyridine-3-carbonyl)-2-methyl-1,2,3,4-tetrahydro-quinoline-4-carboxylic acid (4-chloro-phenyl)-ethyl-amide (23)

Same procedure as for the preparation of (±)-trans-1-(6-methoxy-pyridine-3-carbonyl)-2-methyl-1,2,3,4-tetrahydro-quinoline-4-carboxylic acid (4-chloro-phenyl)-ethyl-amide. Purification via HPLC afforded (±)-cis-1-(6-methoxy-pyridine-3-carbonyl)-2-methyl-1,2,3,4-tetrahydro-quinoline-4-carboxylic acid (4-chloro-phenyl)-ethyl-amide (4%). $^1$H-NMR (CDCl$_3$) δ: 1.10 (d, 3H), 1.25 (t, 3H), 1.70-1.80 (m, 1H), 2.45-2.55 (m, 1H), 3.30-3.40 (dd, 1H), 3.75-3.85 (m, 1H), 3.90 (s, 3H), 4.05-4.15 (m, 1H), 4.55-4.65 (m, 1H), 6.40 (d, 1H), 6.50 (d, 1H), 6.80 (d, 1H), 7.00 (t, 1H), 7.10-7.20 (m, 4H), 7.35 (d, 2H), 7.70 (s, 1H). MS m/z: 464/466 (M+1).

(±)-trans-1-(3-Methoxy-benzoyl)-2-methyl-1,2,3,4-tetrahydro-quinoline-4-carboxylic acid (4-chloro-phenyl)-ethyl-amide (24)

(±)-trans-1-(3-Methoxy-benzoyl)-2-methyl-1,2,3,4-tetrahydro-quinoline-4-carboxylic acid (4-chloro-phenyl)-ethyl-amide was made following general procedure A, substituting 3-methoxy-benzoyl chloride for 4-trifluoromethyl-benzoyl chloride. The crude 1-(3-methoxy-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-trans-1-(3-methoxy-benzoyl)-2-methyl-1,2,3,4-tetrahydro-quinoline-4-carboxylic acid (4-chloro-phenyl)-ethyl-amide (24%). $^1$H-NMR (CDCl$_3$) δ: 0.96 (d, 3H), 1.13 (t, 3H), 1.71-1.80 (m, 1H), 2.45-2.56 (m, 1H), 3.58-3.65 (m, 1H), 3.67 (s, 3H), 3.77-3.93 (m, 2H), 4.98-5.10 (m, 1H), 6.44-6.52 (d, 1H), 6.70-6.74 (d, 1H), 6.76-6.91 (m, 3H), 7.06-7.15 (m, 4H), 7.21 (s, 1H), 7.41-7.49 (d, 2H). MS m/z: 463 (M+1).

(±)-trans-1-(4-Methoxy-benzoyl)-2-methyl-1,2,3,4-tetrahydro-quinoline-4-carboxylic acid (3,4-dichloro-phenyl)-ethyl-amide (25)

(±)-trans-1-(4-Methoxy-benzoyl)-2-methyl-1,2,3,4-tetrahydro-quinoline-4-carboxylic acid (3,4-dichloro-phenyl)-ethyl-amide was made following general procedure B, substituting ethyl-(3,4-dichloro-phenyl)-amine for ethyl-benzyl-amine. The crude 1-(4-methoxy-benzoyl)-2-methyl-1,2,3,4-tetrahydro-quinoline-4-carboxylic acid (3,4-dichloro-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (3,4-dichloro-phenyl)-ethyl-amide. $^1$H-NMR (CDCl$_3$) δ: 1.01 (d, 3H), 1.13 (t, 3H), 1.70-1.79 (m, 1H), 2.51-2.61 (m, 1H), 3.59-3.70 (m, 1H), 3.76 (s, 3H), 3.79-3.92 (m, 2H), 5.06-5.13 (m, 1H), 6.47 (d, 1H), 6.74-6.92 (m, 5H), 7.13 (dd, 1H), 7.37 (d, 1H), 7.49 (d, 2H), 7.56 (d, 1H). MS m/z: 497 (M+1), 499 (M+3).

(±)-trans-1-(4-Methoxy-benzoyl)-2-methyl-1,2,3,4-tetrahydro-quinoline-4-carboxylic acid diethylamide (26)

(±)-trans-1-(4-Methoxy-benzoyl)-2-methyl-1,2,3,4-tetrahydro-quinoline-4-carboxylic acid diethylamide was made following general procedure B substituting diethylamine for ethyl-benzyl-amine. $^1$H-NMR (CDCl$_3$) δ: 1.10-1.29 (m, 9H), 1.97 (ddd, 1H), 2.51 (ddd, 1H), 3.38-3.53 (m, 4H), 4.15 (dd, 1H), 5.06-5.17 (m, 1H), 6.49 (d, 1H), 6.70-6.75 (m, 2H), 6.82 (ddd, 1H), 6.90-7.03 (m, 2H), 7.45-7.50 (m, 2H). MS m/z: 381 (M+1).

(±)-trans-1-(2-Methoxy-benzoyl)-2-methyl-1,2,3,4-tetrahydro-quinoline-4-carboxylic acid (4-chloro-phenyl)-ethyl-amide (27)

(±)-trans-1-(2-Methoxy-benzoyl)-2-methyl-1,2,3,4-tetrahydro-quinoline-4-carboxylic acid (4-chloro-phenyl)-ethyl-amide was made following general procedure A, substituting 2-methoxy-benzoyl chloride for 4-trifluoromethyl-benzoyl chloride. The crude 1-(2-methoxy-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-trans-1-(2-methoxy-benzoyl)-2-methyl-1,2,3,4-tetrahydro-quinoline-4-carboxylic acid (4-chloro-phenyl)-ethyl-amide (12%). MS m/z: 463 (M+1).

(±)-cis-1-[4-(3-Carbamoyl-propoxy)-benzoyl]-2-methyl-1,2,3,4-tetrahydro-quinoline-4-carboxylic acid (4-chloro-phenyl)-ethyl-amide (28) and (±)-trans-1-[4-(3-carbamoyl-propoxy)-benzoyl]-2-methyl-1,2,3,4-tetrahydro-quinoline-4-carboxylic acid (4-chloro-phenyl)-ethyl-amide (31)

A mixture of (±)-cis and trans-4-(4-{4-[(4-chloro-phenyl)-ethyl-carbamoyl]-2-methyl-3,4-dihydro-2H-quinoline-1-carbonyl}-phenoxy)-butyric acid (293 mg, 0.548 mmol) was dissolved in dimethylformamide (5 mL). Hydroxybenzotriazole (111 mg, 0.82 mmol) and diisopropylethylamine (283 mg, 382 uL, 2.19 mmol) were added. To the resulting reaction was added O-(-7-azabenzotriazol-1-yl)-N,N,N',N'-tetramethyluronium hexafluorophosphate (313 mg, 0.82 mmol). The reaction was allowed to stir at room temperature for 5 minutes and ammonium chloride (60 mg, 1.07 mmol) was added. The reaction was stirred at room temperature overnight. Upon completion, the mixture was concentrated in vacuo. The resulting residue was dissolved in ethyl acetate and washed twice with water. The extracts were washed with saturated aqueous sodium bicarbonate and brine, dried over sodium sulfate, filtered, and concentrated. The crude residue was a mixture of cis and trans isomers. Purification via silica gel chromatography (methylene chloride/methanol gradient) afforded, pure (±)-trans-1-[4-(3-carbamoyl-propoxy)-benzoyl]-2-methyl-1,2,3,4-tetrahydro-quinoline-4-carboxylic acid (4-chloro-phenyl)-ethyl-amide (86%) as well as pure (±)-cis-1-[4-(3-carbamoyl-propoxy)-benzoyl]-2-methyl-1,2,3,4-tetrahydro-quinoline-4-carboxylic acid (4-chloro-phenyl)-ethyl-amide. Data for the trans isomer: $^1$H-NMR (CDCl$_3$) δ: 0.97 (d, 3H), 1.11 (t, 3H), 1.72 (ddd, 1H), 2.03-2.13 (m, 2H), 2.34-2.41 (m, 2H), 2.52 (ddd, 1H), 3.59-3.73 (m, 1H), 3.77-3.89 (m, 2H), 3.91-3.97 (m, 2H), 5.00-5.10 (m, 1H), 5.47 (br s, 1H), 5.72 (br s, 1H), 6.44 (d, 1H), 6.68-6.82 (m, 4H), 6.88 (dd, 1H), 7.16-7.22 (m, 2H), 7.43-7.50 (m, 4H). MS m/z: 534 (M+1).

(±)-trans-(3-Diethylamino-pyrazol-1-yl)-[1-(4-methoxy-benzoyl)-2-methyl-1,2,3,4-tetrahydro-quinolin-4-yl]-methanone (29)

(±)-trans-(3-Diethylamino-pyrazol-1-yl)-[1-(4-methoxy-benzoyl)-2-methyl-1,2,3,4-tetrahydro-quinolin-4-yl]-methanone was prepared following general procedure B, substituting N,N-diethyl-1H-pyrazol-3-amine for ethyl-benzyl-amine. Purification by HPLC yielded pure (±)-trans-(3-diethylamino-pyrazol-1-yl)-[1-(4-methoxy-benzoyl)-2-methyl-1,2,3,4-tetrahydro-quinolin-4-yl]-methanone.
$^1$H-NMR (CDCl$_3$) δ: 1.15-1.31 (m, 9H), 2.06 (ddd, 1H), 2.75-2.86 (m, 1H), 3.33-3.43 (m, 4H), 3.74 (s, 3H), 5.00-5.13 (m, 2H), 5.96 (d, 1H), 6.50-6.56 (m, 1H), 6.67-6.73 (m, 2H), 6.87 (ddd, 1H), 6.97 (ddd, 1H), 7.28 (dd, 1H), 7.37-7.44 (m, 2H), 8.05 (d, 1H). MS m/z=447 (M+1).

(±)-trans-1-(6-Methoxy-pyridine-3-carbonyl)-2-methyl-1,2,3,4-tetrahydro-quinoline-4-carboxylic acid (4-chloro-phenyl)-ethyl-amide (30)

A round bottom flask with magnetic stirrer was charged with cis-2-methyl-1,2,3,4-tetrahydro-quinoline-4-carboxylic acid methyl ester (400 mg, 1.95 mmol) in methylene chloride (4.00 mL) under a nitrogen atmosphere. Into the reaction was added 6-chloronicotinoyl chloride (480 mg, 2.73 mmol) and N,N-diisopropylethylamine (0.95 mL, 5.46 mmol) via syringe. The reaction was stirred at room temperature for 18-20 hours. The reaction was transferred to a separatory funnel containing a saturated sodium bicarbonate solution (15 mL), then diluted with methylene chloride (15 mL) and shaken vigorously. The resulting organic layer was separated, washed with brine (1×20 mL), dried over magnesium sulfate, and filtered. The filtrate was concentrated in vacuo to afford an orange residue (800 mg). The residue was purified via flash chromatography (1% methanol/methylene chloride) to yield cis-1-(6-chloro-pyridine-3-carbonyl)-2-methyl-1,2,3,4-tetrahydro-quinoline-4-carboxylic acid methyl ester as a yellow solid (630 mg, 94%).

To a solution of cis-1-(6-chloro-pyridine-3-carbonyl)-2-methyl-1,2,3,4-tetrahydro-quinoline-4-carboxylic acid methyl ester (620 mg, 1.8 mmol) in ethylene glycol dimethyl ether (6.00 mL) was added at 0° C. a 5M solution of sodium methoxide in methanol (3.3 mL, 16.2 mmol). The reaction mixture was stirred at room temperature for 20 hours. The reaction mixture was acidified to pH 1 by addition of aqueous 1N hydrochloric acid and extracted with ethyl acetate. The organic layer was washed with brine, dried over magnesium sulfate, and filtered. The filtrate was concentrated in vacuo to yield 1-(6-methoxy-pyridine-3-carbonyl)-2-methyl-1,2,3,4-tetrahydro-quinoline-4-carboxylic acid (190 mg, 32%).

A round bottom flask with magnetic stirrer was charged with 1-(6-methoxy-pyridine-3-carbonyl)-2-methyl-1,2,3,4-tetrahydro-quinoline-4-carboxylic acid (190 mg, 0.58 mmol) in anhydrous pyridine (1.5 mL). To the reaction was added N-ethyl-p-chloroaniline (185 mg, 1.19 mmol), followed by EDCI (156 mg, 0.82 mmol). The reaction was stirred at room temperature under an argon atmosphere for 18-20 hours. The reaction was poured into water and extracted with ethyl acetate. The organic layer was washed with brine, dried over magnesium sulfate, and filtered. The filtrate was concentrated in vacuo to afford a yellow oil (350 mg). The crude material was purified via silica gel chromatography (1% methanol/methylene chloride) followed by HPLC to yield (±)-trans-1-(6-methoxy-pyridine-3-carbonyl)-2-methyl-1,2,3,4-tetrahydro-quinoline-4-carboxylic acid (4-chloro-phenyl)-ethyl-amide (14%). $^1$H-NMR (CDCl$_3$) δ: 1.05 (d, 3H), 1.13 (t, 3H), 1.65-1.75 (m, 1H), 2.50-2.60 (m, 1H), 3.60-3.70 (m, 1H), 3.80 (q, 2H), 3.95 (s, 3H), 5.02-5.10 (m, 1H), 6.50 (d, 1H), 6.60 (d, 1H), 6.75 (d, 1H), 6.85-7.00 (m, 2H), 7.20 (m, 2H), 7.50 (d, 2H), 7.75 (d, 1H), 8.40 (s, 1H). MS m/z: 464/466 (M+1).

(±)-trans-1-(4-Hydroxy-benzoyl)-2-methyl-1,2,3,4-tetrahydro-quinoline-4-carboxylic acid (4-chloro-phenyl)-ethyl-amide (32)

(±)-trans-1-(4-Methoxy-benzoyl)-2-methyl-1,2,3,4-tetrahydro-quinoline-4-carboxylic acid (4-chloro-phenyl)-ethyl-amide (1.067 g, 2.30 mmol) was dissolved in methylene chloride (20 mL). The solution was cooled to 0° C. Boron tribromide (1.15 g, 0.436 mL, 4.61 mmol) was added via syringe. The reaction was warmed to room temperature and stirred. Two additional aliquots of boron tribromide (0.220 uL each) were added at one hour and two hours. The reaction was stirred for one hour after the second additional aliquot of boron tribromide was added. Upon completion, the reaction was slowly dripped into an aqueous sodium hydroxide solution (50 mL of 6M). The resulting emulsion was extracted with ethyl acetate (2×100 mL). The extracts were combined, washed with water and brine, dried over sodium sulfate, filtered and concentrated. The crude residue was purified by silica gel chromatography (ethyl acetate/hexanes gradient) to afford pure (±)-trans-1-(4-hydroxy-benzoyl)-1,2,3,4-tetrahydro-quinoline-4-carboxylic acid (4-chloro-phenyl)-ethyl-amide (91%). $^1$H-NMR (CDCl$_3$) δ: 0.97 (d, 3H), 1.13 (t, 3H), 1.74 (ddd, 1H), 2.51 (ddd, 1H), 3.64-3.90 (m, 3H), 5.02-5.13 (m, 1H), 6.43 (d, 1H), 6.55-6.61 (m, 2H), 6.77-6.84 (m, 2H), 6.85-6.93 (m, 1H), 7.17-7.22 (m, 2H), 7.33-7.39 (m, 2H), 7.43-7.49 (m, 2H). MS m/z: 477 (M+1).

(±)-1-(4-Methoxy-benzoyl)-1,2,3,4-tetrahydro-quinoline-4-carboxylic acid (4-chloro-phenyl)-ethyl-amide (33)

Step 1. (±)-1,2,3,4-Tetrahydro-quinoline-4-carboxylic acid

Quinoline-4-carboxylic acid (580 mg, 3.35 mmol) was dissolved in an aqueous potassium hydroxide solution (1 M, 10 mL). Nickel/aluminum amalgam (3 g) was added in portions over 1.5 hours. The heterogeneous mixture was stirred at room temperature for 48 hours. Upon completion, the reaction was filtered through Celite® and washed with ethyl acetate. The pH of the aqueous layer was adjusted with concentrated hydrochloric acid to 4-5. Solid sodium chloride was added until the aqueous layer was saturated. The ethyl acetate layer was separated. The aqueous phase was extracted with ethyl acetate. The extracts were combined, washed with minimal brine, dried over sodium sulfate, filtered, and concentrated. 1,2,3,4-Tetrahydro-quinoline-4-carboxylic acid was used without further purification (389 mg, 66%). $^1$H-NMR (CDCl$_3$) δ: 1.95-2.08 (m, 1H), 2.22-2.37 (m, 1H), 3.23-3.34 (m, 1H), 3.39-3.49 (m, 1H), 3.79 (dd, 1H), 6.56 (d, 1H), 6.69 (dd, 1H), 7.07 (dd, 1H), 7.17 (d, 1H). MS m/z: 178 (M+1).

Step 2. (±)-1-(4-Methoxy-benzoyl)-1,2,3,4-tetrahydro-quinoline-4-carboxylic acid 1,2,3,4-Tetrahydro-quinoline-4-carboxylic acid (305 mg, 1.89 mmol) was dissolved in anhydrous tetrahydrofuran (10 mL). Anisoyl chloride (644 mg, 3.78 mmol) was added followed by diisopropylethylamine (733 mg, 1.01 mL, 15.67 mmol). The reaction was stirred at room temperature for 7 days. The mixture was concentrated and partitioned between chloroform and sodium hydroxide (1 M, aqueous). The chloroform extract was set aside. The aqueous phase was acidified with concentrated hydrochloric acid (pH=3-4). The aqueous phase was then extracted with ethyl acetate (three times). The combined extracts were washed with brine, dried over sodium sulfate, filtered, and concentrated. The crude product was used without further purification. MS m/z: 312 (M+1).

Step 3. (±)-1-(4-Methoxy-benzoyl)-1,2,3,4-tetrahydro-quinoline-4-carboxylic acid (4-chloro-phenyl)-ethyl-amide 1-(4-Methoxy-benzoyl)-1,2,3,4-tetrahydro-quinoline-4-carboxylic acid (approx. 1.47 mmol) was suspended in methylene chloride (10 mL) to which one drop of dimethylformamide was added. Oxalyl chloride (375 mg, 275 uL, 2.95 mmol) was added. Vigorous bubbling ensued, followed by dissolution of the starting material. After stirring for 4 hours at room temperature, the yellow solution was concentrated and azeotroped with toluene to remove excess oxalyl chloride. The resulting acid chloride solution was dissolved in methylene chloride (10 mL). Diisopropylethylamine (569 mg, 768 uL, 4.41 mmol) was added, followed by 4-chloro-N-ethylaniline (457 mg, 2.93 mmol). The mixture was stirred at room temperature overnight. The reaction was poured into ethyl acetate and washed with water and brine. The combined organics were dried over sodium sulfate, filtered and concentrated. The crude residue was purified by silica gel chromatography (ethyl acetate/hexanes gradient) to afford (±)-1-(4-methoxy-benzoyl)-1,2,3,4-tetrahydro-quinoline-4-carboxylic acid (4-chloro-phenyl)-ethyl-amide (193 mg) as a foam. $^1$H-NMR (CDCl$_3$) δ: 1.17 (t, 3H), 2.06-2.26 (m, 2H), 3.57-3.70 (m, 2H), 3.73-3.87 (m, 5H), 4.02 (dd, 1H), 6.52 (d, 1H), 6.66-6.74 (m, 2H), 6.84 (ddd, 1H), 6.93-7.06 (m, 2H), 7.17-7.24 (m, 2H), 7.37-7.43 (m, 2H). MS m/z: 449 (M+1).

(±)-trans-1-(4-Methoxy-benzoyl)-2-methyl-1,2,3,4-tetrahydro-quinoline-4-carboxylic acid ethyl-(4-ethyl-phenyl)-amide (34)

(±)-trans-1-(4-Methoxy-benzoyl)-2-methyl-1,2,3,4-tetrahydro-quinoline-4-carboxylic acid ethyl-(4-ethyl-phenyl)-amide was prepared following general procedure B, substituting ethyl-(4-ethyl-phenyl)-amine for ethyl-benzyl-amine. $^1$H-NMR (CDCl$_3$) δ: 0.95 (d, 3H), 1.13 (t, 3H), 1.26 (t, 3H), 1.76 (ddd, 1H), 2.52 (ddd, 1H), 2.69 (q, 2H), 3.63-3.77 (m, 4H), 3.80-3.92 (m, 2H), 5.02-5.13 (m, 1H), 6.42 (d, 1H), 6.70-6.91 (m, 5H), 7.13-7.19 (m, 2H), 7.25-7.32 (m, 2H), 7.47-7.55 (m, 2H). MS m/z: 457 (M+1).

(±)-trans-1-(4-Methoxy-benzoyl)-2-methyl-1,2,3,4-tetrahydro-quinoline-4-carboxylic acid ethyl-(5-methyl-isoxazol-3-yl)-amide (35)

(±)-trans-1-(4-Methoxy-benzoyl)-2-methyl-1,2,3,4-tetrahydro-quinoline-4-carboxylic acid ethyl-(5-methyl-isoxazol-3-yl)-amide was prepared following general procedure B, substituting N-ethyl-5-methyl-isoxazol-3-amine for ethyl-benzyl-amine. The crude product was isolated as a mixture of cis and trans isomers. Purification by HPLC yielded (±)-trans-1-(4-methoxy-benzoyl)-2-methyl-1,2,3,4-tetrahydro-quinoline-4-carboxylic acid ethyl-(5-methyl-isoxazol-3-yl)-amide. $^1$H-NMR (CDCl$_3$) δ: 1.04-1.30 (m, 6H), 1.84-1.98 (m, 1H), 2.45 (br s, 3H), 2.54-2.65 (m, 1H), 3.64-3.85 (m, 5H), 4.30 (dd, 1H), 4.99-5.13 (m, 1H), 5.96 (br s, 1H), 6.49 (d, 1H), 6.70-6.77 (m, 2H), 6.83 (br dd, 1H), 6.87-7.03 (m, 2H), 7.42-7.50 (m, 2H). MS m/z=434 (M+1).

(±)-trans-1-(4-Methoxy-benzoyl)-2-methyl-1,2,3,4-tetrahydro-quinoline-4-carboxylic acid methyl-phenyl-amide (36)

(±)-trans-1-(4-Methoxy-benzoyl)-2-methyl-1,2,3,4-tetrahydro-quinoline-4-carboxylic acid methyl-phenyl-amide was made following general procedure B, substituting N-methyl-aniline for ethyl-benzyl-amine. The crude 1-(4-methoxy-benzoyl)-2-methyl-1,2,3,4-tetrahydro-quinoline-4-carboxylic acid methyl-phenyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid methyl-phenyl-amide. $^1$H-NMR (CDCl$_3$) δ: 0.96 (d, 3H), 1.75-1.83 (m, 1H), 2.51-2.60 (m, 1H), 3.34 (s, 3H), 3.77 (s, 3H), 3.92-3.98 (m, 1H), 5.07-5.12 (m, 1H), 6.44 (d, 1H), 6.75-6.92 (m, 5H), 7.29-7.39 (m, 2H), 7.38-7.54 (m, 5H). MS m/z: 415 (M$^+$).

(±)-trans-1-(4-Methoxy-benzoyl)-2-methyl-1,2,3,4-tetrahydro-quinoline-4-carboxylic acid (3-chloro-4-methyl-phenyl)-ethyl-amide (37)

(±)-trans-1-(4-Methoxy-benzoyl)-2-methyl-1,2,3,4-tetrahydro-quinoline-4-carboxylic acid (3-chloro-4-methylphenyl)-ethyl-amide was made following general procedure B, substituting ethyl-(3-chloro-4-methyl-phenyl)-amine for ethyl-benzyl-amine. The crude 1-(4-methoxy-benzoyl)-2-methyl-1,2,3,4-tetrahydro-quinoline-4-carboxylic acid (3-chloro-4-methyl-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (3-chloro-4-methyl-phenyl)-ethyl-amide. $^1$H-NMR (CDCl$_3$) δ: 0.99 (d, 3H), 1.14 (t, 3H), 1.74-1.82 (m, 1H), 2.44 (s, 3H), 2.49-2.59 (m, 1H), 3.65-3.72 (m, 1H), 3.77 (s, 3H), 3.80-3.92 (m, 2H), 5.00-5.15 (m, 1H), 6.45 (d, 1H), 6.75-6.84 (m, 4H), 6.89-6.94 (m, 1H), 7.07 (dd, 1H), 7.26-7.36 (m, 2H), 7.53 (d, 2H). MS m/z: 477 (M$^+$).

(±)-trans-1-(4-Methoxy-benzoyl)-2-methyl-1,2,3,4-tetrahydro-quinoline-4-carboxylic acid amide (38)

(±)-trans-1-(4-Methoxy-benzoyl)-2-methyl-1,2,3,4-tetrahydro-quinoline-4-carboxylic acid amide was prepared following general procedure B, substituting ammonia in dioxane for ethyl-benzyl-amine. $^1$H-NMR (CD$_3$OD) δ: 1.20 (d, 3H), 1.81 (ddd, 1H), 2.78 (ddd, 1H), 3.77 (s, 3H), 3.87 (dd, 1H), 4.90-4.98 (m, 1H), 6.55 (d, 1H), 6.74-6.83 (m, 2H), 6.94 (ddd, 1H), 7.09 (ddd, 1H), 7.33 (d, 1H), 7.36-7.41 (m, 2H). MS m/z=325 (M+1).

(±)-trans-1-(4-Dimethylamino-benzoyl)-2-methyl-1,2,3,4-tetrahydro-quinoline-4-carboxylic acid (4-chloro-phenyl)-ethyl-amide (40)

(±)-trans-1-(4-Dimethylamino-benzoyl)-2-methyl-1,2,3,4-tetrahydro-quinoline-4-carboxylic acid (4-chloro-phenyl)-ethyl-amide was made following general procedure A, substituting 4-dimethylamino-benzoyl chloride for 4-trifluoromethyl-benzoyl chloride. The crude 1-(4-dimethylamino-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-trans-1-(4-dimethylamino-benzoyl)-2-methyl-1,2,3,4-tetrahydro-quinoline-4-carboxylic acid (4-chloro-phenyl)-ethyl-amide (54%). $^1$H-NMR (CDCl$_3$) δ: 0.96 (d, 3H), 1.13 (t, 3H), 1.71-1.80 (m, 1H), 2.45-2.56 (1H, m), 2.93 (s, 6H), 3.64-3.93 (m, 3H), 4.98-5.10 (m, 1H), 6.50-6.59 (m, 3H), 6.78-6.90 (m, 3H), 7.19-7.23 (m, 2H), 7.41-7.49 (m, 4H). MS m/z: 476 (M+1).

(±)-trans-1-(4-Methoxy-benzoyl)-2-methyl-1,2,3,4-tetrahydro-quinoline-4-carboxylic acid ethyl-(1H-indol-4-yl)-amide (41)

(±)-trans-1-(4-Methoxy-benzoyl)-2-methyl-1,2,3,4-tetrahydro-quinoline-4-carboxylic acid ethyl-(1H-indol-4-yl)-amide was prepared following general procedure B, substituting N-ethyl-1H-indol-4-amine for ethyl-benzyl-amine. $^1$H-NMR (CDCl$_3$) δ: 0.93 (d, 3H), 1.17 (t, 3H), 1.50-1.60 (m, 1H), 2.50-2.59 (m, 1H), 3.60-3.70 (m, 1H), 3.74 (s, 3H), 3.78-3.92 (m, 2H), 5.00-5.14 (m, 1H), 6.40-6.50 (m, 1H), 6.59-6.63 (m, 1H), 6.70-7.10 (m, 6H), 7.20-7.30 (m, 2H), 7.40-7.46 (m, 1H), 7.52-7.61 (m, 2H), 9.12 (br s, 1H). MS m/z: 468 (M+1), 469 (M+2)

(±)-trans-1-(Benzo[b]thiophene-2-carbonyl)-2-methyl-1,2,3,4-tetrahydro-quinoline-4-carboxylic acid (4-chloro-phenyl)-ethyl-amide (42)

(±)-trans-1-(Benzo[b]thiophene-2-carbonyl)-2-methyl-1,2,3,4-tetrahydro-quinoline-4-carboxylic acid (4-chloro-phenyl)-ethyl-amide was made following general procedure A, substituting benzo[b]thiophene-2-carbonyl chloride for 4-trifluoromethyl-benzoyl chlorided. Benzo[b]thiophene-2-carbonyl chloride was prepared by reaction of thianaphthene-2-carboxylic acid with oxalyl chloride and dimethylformamide in methylene chloride. The crude 1-(benzo[b]thiophene-2-carbonyl)-2-methyl-1,2,3,4-tetrahydro-quinoline-4-carboxylic acid (4-chloro-phenyl)-ethyl-amide was isolated as a mixture of cis and trans isomers. Purification by silica gel chromatography (1% methanol/methylene chloride) followed by purification via HPLC yielded (±)-trans-2-methyl-1-(pyrimidine-5-carbonyl)-1,2,3,4-tetrahydro-quinoline-4-carboxylic acid (4-chloro-phenyl)-ethyl-amide (34%). $^1$H-NMR (CDCl$_3$) δ: 1.02-1.18 (m, 6H), 1.65-1.75 (m, 1H), 2.55-2.65 (m, 1H), 3.60-3.70 (m, 1H), 3.80 (q, 2H), 5.05-5.15 (m, 1H), 6.70 (d, 1H), 6.80-7.00 (m, 3H), 7.20-7.40 (m, 4H), 7.45 (s, 1H), 7.50 (d, 2H), 7.70 (d, 1H), 7.80 (d, 1H). MS m/z: 489/491 (M+1).

(±)-trans-[1-(4-Methoxy-benzoyl)-2-methyl-1,2,3,4-tetrahydro-quinolin-4-yl]-(4-phenyl-piperazin-1-yl)-methanone (43)

(±)-trans-[1-(4-Methoxy-benzoyl)-2-methyl-1,2,3,4-tetrahydro-quinolin-4-yl]-(4-phenyl-piperazin-1-yl)-methanone was prepared following general procedure B, substituting 1-phenyl-piperazine for ethyl-benzyl-amine. $^1$H-NMR (CDCl$_3$) δ: 1.21 (d, 3H), 1.95 (ddd, 1H), 2.52 (ddd, 2H), 3.12-3.17 (m, 4H), 3.69-3.84 (m, 7H), 4.21 (dd, 1H), 5.00-5.11 (m, 1H), 6.56 (d, 1H), 6.69-6.73 (m, 2H), 6.82-7.03 (m, 5H), 7.05-7.17 (m, 1H), 7.22-7.28 (m, 2H), 7.45-7.50 (m, 2H). MS m/z: 470 (M+1).

(±)-trans-1-(4-Methoxy-benzoyl)-2-methyl-1,2,3,4-tetrahydro-quinolin-4-yl-morpholin-4-yl-methanone (44)

(±)-trans-1-(4-Methoxy-benzoyl)-2-methyl-1,2,3,4-tetrahydro-quinolin-4-yl-morpholin-4-yl-methanone was made following general procedure B, substituting morpholine for ethyl-benzyl-amine. $^1$H-NMR (CDCl$_3$) δ: 1.21 (d, 3H), 1.96 (ddd, 1H), 2.49 (ddd, 1H), 3.56-3.79 (m, 1H), 4.16 (t, 1H), 5.02-5.11 (m, 1H), 6.57 (d, 1H), 6.71-6.77 (m, 2H), 6.89 (ddd, 1H), 6.96-7.08 (m, 2H), 7.45-7.51 (m, 2H). MS m/z: 395 (M+1).

(±)-trans-4-(4-{4-[(4-Chloro-phenyl)-ethyl-carbamoyl]-2-methyl-3,4-dihydro-2H-quinoline-1-carbonyl}-phenoxy)-acetic acid (45)

(±)-trans-4-(4-{4-[(4-Chloro-phenyl)-ethyl-carbamoyl]-2-methyl-3,4-dihydro-2H-quinoline-1-carbonyl}-phenoxy)-acetic acid was made following the procedures for the synthesis of (±)-trans-4-(4-{4-[(4-chloro-phenyl)-ethyl-carbamoyl]-2-methyl-3,4-dihydro-2H-quinoline-1-carbonyl}-phenoxy)-butyric acid from (±)-trans-1-(4-hydroxy-benzoyl)-2-methyl-1,2,3,4-tetrahydro-quinoline-4-carboxylic acid (4-chloro-phenyl)-ethyl-amide. Methyl chloroacetate was substituted for ethyl-4-bromobutyrate. $^1$H-NMR (CDCl$_3$) δ: 0.96 (d, 3H), 1.05 (t, 3H), 1.63 (m, 1H), 2.40 (m, 1H), 3.46-3.64 (m, 1H), 3.74-3.81 (m, 2H), 4.28 (s, 2H), 4.98 (m, 1H), 6.44 (d, 1H), 6.69-6.89 (m, 5H), 7.18-7.28 (m, 2H), 7.40 (d, 2H), 7.46 (d, 2H). MS m/z: 507 (M+1).

(±)-cis-1-[4-(3-Carbamoyl-3-methyl-butoxy)-benzoyl]-2-methyl-1,2,3,4-tetrahydro-quinoline-4-carboxylic acid (4-chloro-phenyl)-ethyl-amide (46) and (±)-trans-1-[4-(3-carbamoyl-3-methyl-butoxy)-benzoyl]-2-methyl-1,2,3,4-tetrahydro-quinoline-4-carboxylic acid (4-chloro-phenyl)-ethyl-amide (75)

(±)-cis-1-[4-(3-Carbamoyl-3-methyl-butoxy)-benzoyl]-2-methyl-1,2,3,4-tetrahydro-quinoline-4-carboxylic acid (4-chloro-phenyl)-ethyl-amide and (±)-trans-1-[4-(3-carbamoyl-3-methyl-butoxy)-benzoyl]-2-methyl-1,2,3,4-tetrahydro-quinoline-4-carboxylic acid (4-chloro-phenyl)-ethyl-amide were made following the procedure detailing the synthesis of (±)-cis-1-[4-(3-carbamoyl-propoxy)-benzoyl]-2-methyl-1,2,3,4-tetrahydro-quinoline-4-carboxylic acid (4-chloro-phenyl)-ethyl-amide and (±)-trans-1-[4-(3-carbamoyl-propoxy)-benzoyl]-2-methyl-1,2,3,4-tetrahydro-quinoline-4-carboxylic acid (4-chloro-phenyl)-ethyl-amide. A mixture of (±)-cis and trans-4-(4-{4-[(4-chloro-phenyl)-ethyl-carbamoyl]-2-methyl-3,4-dihydro-2H-quinoline-1-carbonyl}-phenoxy)-2,2-dimethyl-butyric acid was substituted for a mixture of (±)-cis and trans-4-(4-{4-[(4-chloro-phenyl)-ethyl-carbamoyl]-2-methyl-3,4-dihydro-2H-quinoline-1-carbonyl}-phenoxy)-butyric acid. Data for the trans isomer: $^1$H-NMR (CDCl$_3$) δ: 0.97 (d, 3H), 1.11 (t, 3H), 1.24 (s, 6H), 1.71 (ddd, 1H), 1.96-2.01 (m, 2H), 2.48-2.59 (m, 1H), 3.59-3.73 (m, 1H), 3.74-3.90 (m, 2H), 3.93-4.01 (m, 2H), 5.00-5.12 (m, 1H), 5.39-5.85 (br m, 2H), 6.34 (d, 1H), 6.67-6.92 (m, 5H), 7.16-7.22 (m, 2H), 7.41-7.51 (m, 4H). MS m/z: 562 (M+1).

(±)-trans-1-(4-Methoxy-benzoyl)-2-methyl-1,2,3,4-tetrahydro-quinoline-4-carboxylic acid (4-carbamoyl-phenyl)-ethyl-amide (47)

(±)-trans-1-(4-Methoxy-benzoyl)-2-methyl-1,2,3,4-tetrahydro-quinoline-4-carboxylic acid (4-carbamoyl-phenyl)-ethyl-amide was made following general procedure B, substituting ethyl-(4-carbamoyl-phenyl)-amine for ethyl-benzyl-amine. The crude 1-(4-methoxy-benzoyl)-2-methyl-1,2,3,4-tetrahydro-quinoline-4-carboxylic acid (4-carbamoyl-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (4-carbamoyl-phenyl)-ethyl-amide. $^1$H-NMR (CDCl$_3$) δ: 0.97 (d, 3H), 1.14 (t, 3H), 1.71-1.79 (m, 1H), 2.49-2.59 (m, 1H), 3.66-3.76 (m, 4H), 3.82-3.96 (m, 2H), 5.03-5.08 (m, 1H), 6.04-6.12 (bs, 2H), 6.49 (d, 1H), 6.74-6.93 (m, 5H), 7.34 (d, 2H), 7.49 (d, 2H), 7.97 (d, 2H). MS m/z: 472 (M$^+$).

(±)-trans-1-(4-Methoxy-benzoyl)-2-methyl-1,2,3,4-tetrahydro-quinoline-4-carboxylic acid (3-chloro-phenyl)-ethyl-amide (48)

(±)-trans-1-(4-Methoxy-benzoyl)-2-methyl-1,2,3,4-tetrahydro-quinoline-4-carboxylic acid (3-chloro-phenyl)-ethyl-amide was made following general procedure B, substituting ethyl-(3-chloro-phenyl)-amine for ethyl-benzyl-amine. The crude 1-(4-methoxy-benzoyl)-2-methyl-1,2,3,4-tetrahydro-quinoline-4-carboxylic acid (3-chloro-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (3-chloro-phenyl)-ethyl-amide. $^1$H-NMR (CDCl$_3$) δ: 0.99 (d, 3H), 1.15 (t, 3H), 1.72-1.79 (m, 1H), 2.51-2.61 (m, 1H), 3.64-3.73 (m, 1H), 3.77 (s, 3H), 3.81-3.94 (m, 2H), 5.07-5.12 (m, 1H), 6.46 (d, 1H), 6.75-6.93 (m, 5H), 7.16-7.19 (m, 1H), 7.27-7.28 (m, 1H), 7.42-7.44 (m, 2H), 7.51 (d, 2H). MS m/z: 463 (M$^+$), 465 (M+2).

(±)-trans-2-Methyl-1-(4-trifluoromethoxy-benzoyl)-1,2,3,4-tetrahydro-quinoline-4-carboxylic acid (4-chloro-phenyl)-ethyl-amide (49)

(±)-trans-2-Methyl-1-(4-trifluoromethoxy-benzoyl)-1,2,3,4-tetrahydro-quinoline-4-carboxylic acid (4-chloro-phenyl)-ethyl-amide was made following general procedure A, substituting 4-trifluoromethoxy-benzoyl chloride for 4-trifluoromethyl-benzoyl chloride. The crude 2-methyl-1-(4-trifluoromethoxy-benzoyl)-1,2,3,4-tetrahydro-quinoline-4-carboxylic acid (4-chloro-phenyl)-ethyl-amide was isolated as a mixture of cis and trans isomers. Purification via silica gel column (hexanes/ethyl acetate) provided (±)-trans-2-methyl-1-(4-trifluoromethoxy-benzoyl)-1,2,3,4-tetrahydro-quinoline-4-carboxylic acid (4-chloro-phenyl)-ethyl-amide (56%). $^1$H-NMR (CDCl$_3$) δ: 1.01 (d, 3H), 1.12 (t, 3H), 1.66-1.77 (m, 1H), 2.46-2.58 (m, 1H), 3.60-3.74 (m, 1H), 3.77-3.90 (m, 2H), 5.02-5.15 (m, 1H), 6.37-6.42 (m, 1H), 6.78-6.85 (m, 2H), 6.90-6.97 (m, 1H), 7.05-7.10 (m, 2H), 7.18-7.26 (m, 2H), 7.44-7.50 (m, 2H), 7.58-7.63 (m, 2H). MS m/z: 517 (M+1).

(±)-trans-1-(4-Methoxy-benzoyl)-2-methyl-1,2,3,4-tetrahydro-quinoline-4-carboxylic acid ethyl-(4-methyl-3-trifluoromethyl-phenyl)-amide (50)

(±)-trans-1-(4-Methoxy-benzoyl)-2-methyl-1,2,3,4-tetrahydro-quinoline-4-carboxylic acid ethyl-(4-methyl-3-trifluoromethyl-phenyl)-amide was made following general procedure B, substituting ethyl-(4-methyl-3-trifluoromethyl-phenyl)-amine for ethyl-benzyl-amine. The crude 1-(4-methoxy-benzoyl)-2-methyl-1,2,3,4-tetrahydro-quinoline-4-carboxylic acid ethyl-(4-methyl-3-trifluoromethyl-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-methyl-3-trifluoromethyl-phenyl)-amide. $^1$H-NMR (CDCl$_3$) δ: 0.99 (d, 3H), 1.15 (t, 3H), 1.68-1.76 (m, 1H), 2.56-2.64 (m, 4H), 3.62-3.71 (m, 1H), 3.78 (s, 3H), 3.81-3.96 (m, 2H), 5.05-5.15 (m, 1H), 6.46 (d, 1H), 6.69-6.91 (m, 6H), 7.32-7.52 (m, 4H). MS m/z: 511 (M$^+$), 512 (M+1).

(±)-trans-1-(4-Methoxy-benzoyl)-2-methyl-1,2,3,4-tetrahydro-quinoline-4-carboxylic acid ethyl-phenyl-amide (51)

(±)-trans-1-(4-Methoxy-benzoyl)-2-methyl-1,2,3,4-tetrahydro-quinoline-4-carboxylic acid ethyl-phenyl-amide was made following general procedure B, substituting N-ethylaniline for ethyl-benzyl-amine. The crude 1-(4-methoxy-benzoyl)-2-methyl-1,2,3,4-tetrahydro-quinoline-4-carboxylic acid ethyl-phenyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-phenyl-amide. $^1$H-NMR (CDCl$_3$) δ: 0.96 (d, 3H), 1.17 (t, 3H), 1.75-1.83 (m, 1H), 2.48-2.57 (m, 1H), 3.68-3.74 (m, 1H), 3.77 (s, 3H), 3.84-3.90 (m, 2H), 5.07-5.13 (m, 1H), 6.43 (d, 1H), 6.74-6.82 (m, 3H), 6.86-6.94 (m, 2H), 7.16 (d, 2H), 7.28 (d, 2H), 7.52-7.55 (m, 2H). MS m/z: 430 (M+1).

(±)-cis-1-(4-Fluoro-benzoyl)-2-methyl-1,2,3,4-tetrahydro-quinoline-4-carboxylic acid (4-chloro-phenyl)-ethyl-amide (52)

(±)-cis-1-(4-fluoro-benzoyl)-2-methyl-1,2,3,4-tetrahydro-quinoline-4-carboxylic acid (4-chloro-phenyl)-ethyl-amide was made following general procedure A, substituting 4-fluoro-benzoyl chloride for 4-trifluoromethyl-benzoyl chloride. The crude 1-(4-fluoro-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-cis-1-(4-fluoro-benzoyl)-2-methyl-1,2,3,4-tetrahydro-quinoline-4-carboxylic acid (4-chloro-phenyl)-ethyl-amide (13%). $^1$H-NMR (CDCl$_3$) δ: 1.15 (d, 3H), 1.24 (t, 3H), 1.65-1.77 (sextuplet, 1H), 2.48-2.56 (m, 1H), 3.28-3.34 (dd, 1H), 3.73-3.85 (sextuplet, 1H), 3.95-4.07 (sextuplet, 1H), 4.57-4.69 (m, 1H), 6.35-6.43 (d, 1H), 6.66-6.71 (m, 2H), 6.76-6.82 (t, 2H), 6.85-6.95 (t, 1H), 7.10-7.24 (m, 4H), 7.27-7.37 (d, 2H). MS m/z: 451 (M+1).

rel-(2S,4S)-1-(4-Ethyl-benzoyl)-2-methyl-1,2,3,4-tetrahydro-quinoline-4-carboxylic acid (4-chloro-phenyl)-ethyl-amide (53)

(±)-trans-1-(4-Ethyl-benzoyl)-2-methyl-1,2,3,4-tetrahydro-quinoline-4-carboxylic acid (4-chloro-phenyl)-ethyl-amide was prepared following general procedure A, substituting 4-ethyl-benzoyl chloride for 4-trifluoromethyl-benzoyl chloride. The crude 1-(4-ethyl-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC provided (±)-trans-1-(4-ethyl-benzoyl)-2-methyl-1,2,3,4-tetrahydro-quinoline-4-carboxylic acid (4-chloro-phenyl)-ethyl-amide.

rel-(2S,4S)-1-(4-Ethyl-benzoyl)-2-methyl-1,2,3,4-tetrahydro-quinoline-4-carboxylic acid (4-chloro-phenyl)-ethyl-amide was isolated from (±)-trans-1-(4-ethyl-benzoyl)-2-methyl-1,2,3,4-tetrahydro-quinoline-4-carboxylic acid (4-chloro-phenyl)-ethyl-amide by preparative chiral HPLC. Analytical data for the enantiomer was identical to the racemate. $^1$H-NMR (CDCl$_3$) δ: 0.98 (d, 3H), 1.13 (t, 3H), 1.17 (t, 3H), 1.67-1.77 (m, 1H), 2.59 (q, 2H), 2.49-2.61 (m, 1H), 3.61-3.75 (m, 1H), 3.78-3.93 (m, 2H), 5.04-5.14 (m, 1H), 6.44-6.50 (m, 1H), 6.73-6.83 (m, 1H), 6.85-6.92 (m, 1H), 7.04-7.10 (m, 2H), 7.17-7.21 (m, 2H), 7.41-7.48 (m, 4H). MS m/z: 461 (M+1).

(±)-cis-1-[2-(4-Methoxy-phenyl)-acetyl]-2-methyl-1,2,3,4-tetrahydro-quinoline-4-carboxylic acid (4-chloro-phenyl)-ethyl-amide (54)

Same procedure as for the preparation of (±)-trans-1-[2-(4-methoxy-phenyl)-acetyl]-2-methyl-1,2,3,4-tetrahydro-quinoline-4-carboxylic acid (4-chloro-phenyl)-ethyl-amide. Further purification by HPLC afforded (±)-cis-1-[2-(4-methoxy-phenyl)-acetyl]-2-methyl-1,2,3,4-tetrahydro-quinoline-4-carboxylic acid (4-chloro-phenyl)-ethyl-amide (13%). $^1$H-NMR (CDCl$_3$) δ: 1.05 (d, 3H), 1.20 (t, 3H), 1.60 (m, 1H), 2.25-2.35 (d, 1H), 3.05-3.15 (m, 1H), 3.40 (s, 2H), 3.65-3.75 (m, 1H), 3.80 (s, 3H), 4.00-4.10 (m, 1H), 4.55-4.65 (m, 1H), 6.80 (m, 4H), 7.10 (d, 2H), 7.30 (m, 4H), 7.35 (d, 2H). MS m/z: 477/479 (M+1).

(±)-trans-4-(4-{4-[(4-Chloro-phenyl)-ethyl-carbamoyl]-2-methyl-3,4-dihydro-2H-quinoline-1-carbonyl}-phenoxy)-2,2-dimethyl-butyric acid (55) and (±)-cis-4-(4-{4-[(4-Chloro-phenyl)-ethyl-carbamoyl]-2-methyl-3,4-dihydro-2H-quinoline-1-carbonyl}-phenoxy)-2,2-dimethyl-butyric acid (76)

(±)-trans-4-(4-{4-[(4-Chloro-phenyl)-ethyl-carbamoyl]-2-methyl-3,4-dihydro-2H-quinoline-1-carbonyl}-phenoxy)-2,2-dimethyl-butyric acid was made following the procedures for making (±)-trans-4-(4-{4-[(4-chloro-phenyl)-ethyl-carbamoyl]-2-methyl-3,4-dihydro-2H-quinoline-1-carbonyl}-phenoxy)-butyric acid from (±)-trans-1-(4-hydroxy-benzoyl)-2-methyl-1,2,3,4-tetrahydro-quinoline-4-carboxylic acid (4-chloro-phenyl)-ethyl-amide. 5-Bromo-2,2-dimethyl-pentanoic acid ethyl ester was substituted for ethyl-4-bromobutyrate. The crude product was obtained as a mixture of cis and trans isomers. The trans isomer was obtained and characterized. $^1$H-NMR (CDCl$_3$) δ: 0.97 (d, 3H), 1.12 (t, 3H), 1.26 (s, 6H), 1.73 (ddd, 1H), 2.00-2.08 (m, 2H), 2.47-2.58 (m, 1H), 3.57-3.73 (m, 2H), 3.76-3.90 (m, 2H), 3.95-4.03 (m, 2H), 5.02-5.11 (m, 1H), 6.44 (d, 1H), 6.67-6.74 (m, 2H), 6.75-6.83 (m, 2H), 6.84-6.92 (dd, 1H), 7.17-7.23 (m, 2H), 7.41-7.51 (m, 4H). MS m/z: 563 (M+1).

(±)-trans-1-(4-Methoxy-benzoyl)-2-methyl-1,2,3,4-tetrahydro-quinoline-4-carboxylic acid (4-chloro-phenyl)-propyl-amide (56)

(±)-trans-1-(4-Methoxy-benzoyl)-2-methyl-1,2,3,4-tetrahydro-quinoline-4-carboxylic acid (4-chloro-phenyl)-propyl-amide was made following general procedure B, substituting N-propyl-4-chloroaniline for ethyl-benzyl-amine. $^1$H-NMR (CDCl$_3$) δ: 0.88 (t, 3H), 0.97 (d, 3H), 1.46-1.62 (m, 2H), 1.75 (ddd, 1H), 2.52 (ddd, 1H), 3.53-3.66 (m, 1H), 3.69-3.88 (m, 5H), 5.02-5.12 (m, 1H), 6.44 (m, 1H), 6.69-6.94 (m, 5H), 7.17-7.23 (m, 2H), 7.42-7.53 (m, 4H). MS m/z: 477 (M+1).

(±)-trans-1-(4-Methoxy-benzoyl)-2-methyl-1,2,3,4-tetrahydro-quinoline-4-carboxylic acid ethyl-(3-fluoro-4-methyl-phenyl)-amide (57)

(±)-trans-1-(4-Methoxy-benzoyl)-2-methyl-1,2,3,4-tetrahydro-quinoline-4-carboxylic acid ethyl-(3-fluoro-4-methyl-phenyl)-amide was made following general procedure B, substituting ethyl-(3-fluoro-4-methyl-phenyl)-amine for ethyl-benzyl-amine. The crude 1-(4-methoxy-benzoyl)-2-methyl-1,2,3,4-tetrahydro-quinoline-4-carboxylic acid ethyl-(3-fluoro-4-methyl-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(3-fluoro-4-methyl-phenyl)-amide. $^1$H-NMR (CDCl$_3$) δ: 0.99 (d, 3H), 1.15 (t, 3H), 1.76-1.84 (m, 1H), 2.34 (bs, 3H), 2.49-2.58 (m, 1H), 3.63-3.78 (m, 4H), 3.83-3.92 (m, 2H), 5.08-5.13 (m, 1H), 6.45 (d, 1H), 6.75-6.99 (m, 6H), 7.27-7.33 (m, 2H), 7.53 (d, 2H). MS m/z: 461 (M$^+$).

(±)-trans-1-(4-Methoxy-benzoyl)-2-methyl-1,2,3,4-tetrahydro-quinoline-4-carboxylic acid (4-chloro-phenyl)-methyl-amide (58)

(±)-trans-1-(4-Methoxy-benzoyl)-2-methyl-1,2,3,4-tetrahydro-quinoline-4-carboxylic acid (4-chloro-phenyl)-methyl-amide was made following general procedure B, substituting N-methyl-p-chloro-aniline for ethyl-benzyl-amine.

The crude 1-(4-methoxy-benzoyl)-2-methyl-1,2,3,4-tetrahydro-quinoline-4-carboxylic acid (4-chloro-phenyl)-methylamide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (4-chloro-phenyl)-methyl-amide. $^1$H-NMR (CDCl$_3$) δ: 1.00 (d, 3H), 1.73-1.81 (m, 1H), 2.51-2.60 (m, 1H), 3.31 (s, 3H), 3.78 (s, 3H), 3.90-3.95 (m, 1H), 5.07-5.15 (m, 1H), 6.47 (d, 1H), 6.75-6.93 (m, 5H), 7.24-7.27 (m, 2H), 7.46-7.54 (m, 4H). MS m/z: 449 (M$^+$).

(±)-trans-1-(4-Methoxy-benzoyl)-2-methyl-1,2,3,4-tetrahydro-quinoline-4-carboxylic acid (4-chlorophenyl)-ethyl-amide (59)

(±)-trans-1-(4-Methoxy-benzoyl)-2-methyl-1,2,3,4-tetrahydro-quinoline-4-carboxylic acid (4-chloro-phenyl)-ethyl-amide was prepared following general procedure A, substituting 4-methoxy-benzoyl chloride for 4-trifluoromethyl-benzoyl chloride. The crude 1-(4-methoxy-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC provided (±)-trans-1-(4-methoxy-benzoyl)-2-methyl-1,2,3,4-tetrahydro-quinoline-4-carboxylic acid (4-chloro-phenyl)-ethyl-amide. $^1$H-NMR (CDCl$_3$) δ: 0.98 (d, 3H), 1.12 (t, 3H), 1.67-1.79 (m, 1H), 2.45-2.59 (m, 1H), 3.60-3.73 (m, 1H), 3.76 (s, 3H), 3.77-3.91 (m, 2H), 5.01-5.15 (m, 1H), 6.41-6.47 (m, 1H), 6.71-6.84 (m, 4H), 6.85-6.93 (m, 1H), 7.18-7.25 (m, 2H), 7.43-7.54 (m, 4H). MS m/z: 463 (M+1).

rel-(2S,4S)-4-(4-{4-[(4-Chloro-phenyl)-ethyl-carbamoyl]-2-methyl-3,4-dihydro-2H-quinoline-1-carbonyl}-phenoxy)-butyric acid (60) and rel-(2R,4R)-4-(4-{4-[(4-chloro-phenyl)-ethyl-carbamoyl]-2-methyl-3,4-dihydro-2H-quinoline-1-carbonyl}-phenoxy)-butyric acid (66)

rel-(2S,4S)-4-(4-{4-[(4-Chloro-phenyl)-ethyl-carbamoyl]-2-methyl-3,4-dihydro-2H-quinoline-1-carbonyl}-phenoxy)-butyric acid and rel-(2R,4R)-4-(4-{4-[(4-chloro-phenyl)-ethyl-carbamoyl]-2-methyl-3,4-dihydro-2H-quinoline-1-carbonyl}-phenoxy)-butyric acid were isolated from (±)-trans-4-(4-{4-[(4-chloro-phenyl)-ethyl-carbamoyl]-2-methyl-3,4-dihydro-2H-quinoline-1-carbonyl}-phenoxy)-butyric acid by preparative chiral HPLC. Data for single enantiomer (identical to enantiomer to racemate), absolute stereochemistry unknown: $^1$H-NMR (CD$_3$OD) δ: 0.97 (d, 3H), 1.12 (t, 3H), 4.73 (ddd, 1H), 2.00-2.13 (m, 2H), 2.47-2.58 (m, 3H), 3.61-3.99 (m, 5H), 5.02-5.12 (m, 1H), 6.44 (d, 1H), 6.68-6.74 (m, 2H), 6.75-6.83 (m, 2H), 6.85-6.92 (m, 1H), 7.17-7.25 (m, 3H), 7.42-7.51 (m, 4H). MS m/z: 535 (M+1).

(±)-trans-1-(4-Methoxy-benzoyl)-2-methyl-1,2,3,4-tetrahydro-quinoline-4-carboxylic acid ethyl-o-tolylamide (61)

(±)-trans-1-(4-Methoxy-benzoyl)-2-methyl-1,2,3,4-tetrahydro-quinoline-4-carboxylic acid ethyl-o-tolyl-amide was made following general procedure B, substituting ethyl-o-tolyl-amine for ethyl-benzyl-amine. The crude 1-(4-methoxy-benzoyl)-2-methyl-1,2,3,4-tetrahydro-quinoline-4-carboxylic acid ethyl-o-tolyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-o-tolyl-amide. $^1$H-NMR (CDCl$_3$) δ: 0.96 (d, 3H), 1.14 (t, 3H), 1.75-1.78 (m, 1H), 2.31 (s, 3H), 2.47-2.56 (m, 1H), 3.74-3.77 (m, 4H), 4.19-4.28 (m, 2H), 5.10-5.05 (m, 1H), 6.45 (d, 1H), 6.68-6.92 (m, 5H), 7.26-7.40 (m, 4H), 7.49-7.55 (m, 2H). MS m/z: 444 (M+1).

(±)-trans-1-(3-Fluoro-4-methoxy-benzoyl)-2-methyl-1,2,3,4-tetrahydro-quinoline-4-carboxylic acid (4-chloro-phenyl)-ethyl-amide (62)

(±)-trans-1-(3-Fluoro-4-methoxy-benzoyl)-2-methyl-1,2,3,4-tetrahydro-quinoline-4-carboxylic acid (4-chloro-phenyl)-ethyl-amide was made following general procedure A, substituting 3-fluoro-4-methoxy-benzoyl chloride for 4-trifluoromethyl-benzoyl chloride. The crude 1-(3-fluoro-4-methoxy-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-trans-1-(3-fluoro-4-methoxy-benzoyl)-2-methyl-1,2,3,4-tetrahydro-quinoline-4-carboxylic acid (4-chloro-phenyl)-ethyl-amide (24%). $^1$H-NMR (CDCl$_3$) δ: 0.99 (d, 3H), 1.13 (t, 3H), 1.65-1.71 (m, 1H), 2.53-2.62 (m, 1H), 3.57-3.68 (m, 1H), 3.79-3.90 (m, 2H), 3.84 (s, 3H), 4.98-5.10 (m, 1H), 6.42-6.45 (d, 1H), 6.66-6.69 (d, 1H), 6.77-6.91 (m, 3H), 7.17-7.28 (m, 3H), 7.35 (d, 1H), 7.44-7.47 (d, 2H). MS m/z: 481 (M+1).

(±)-trans-2-Methyl-1-(pyridine-4-carbonyl)-1,2,3,4-tetrahydro-quinoline-4-carboxylic acid (4-chlorophenyl)-ethyl-amide (63)

A round bottom flask with magnetic stirrer was charged with cis-2-methyl-1,2,3,4-tetrahydro-quinoline-4-carboxylic acid methyl ester (300 mg, 1.46 mmol) in methylene chloride (3.00 mL) under a nitrogen atmosphere. Into the reaction was added isonicotinoyl chloride hydrochloride (338 mg, 1.90 mmol) and N,N-diisopropylethylamine (1.02 mL, 5.84 mmol) via syringe. The reaction was stirred at room temperature for 18-20 hours. The reaction was transferred to a separatory funnel containing a saturated sodium bicarbonate solution (15 mL), then diluted with ethyl acetate (15 mL) and shaken vigorously. The resulting organic layer was separated, washed with brine (1×20 mL), dried over magnesium sulfate, and filtered. The filtrate was concentrated in vacuo to afford a yellow residue (530 mg). The residue was purified via flash chromatography (2% methanol/methylene chloride) to yield cis-2-methyl-1-(pyridine-4-carbonyl)-1,2,3,4-tetrahydro-quinoline-4-carboxylic acid methyl ester as a white solid (420 mg, 93%).

To a solution of N-ethyl-4-chloroaniline (650 mg, 4.18 mmol) in anhydrous toluene at 10° C. was slowly added a 2M solution of trimethylaluminium in hexanes (2.1 mL, 4.18 mmol). The reaction mixture was stirred at room temperature until gas evolution stopped. A second round bottom flask was charged with cis-2-methyl-1-(pyridine-4-carbonyl)-1,2,3,4-tetrahydro-quinoline-4-carboxylic acid methyl ester (370 mg, 1.19 mmol) and the preformed aluminum amide was added. The resulting reaction mixture was refluxed for 20 hours. The reaction was concentrated, quenched with 1M aqueous hydrochloric acid at 0° C. (exothermic!), basified with 1M aqueous sodium hydroxide, and extracted with ethyl acetate. The resulting organic layer was separated, washed with brine, dried over magnesium sulfate, and filtered. The filtrate was concentrated in vacuo to afford an orange oil which was purified via flash chromatography (1% methanol/methylene chloride) followed by HPLC to provide (±)-trans-2-methyl-1-(pyridine-4-carbonyl)-1,2,3,4-tetrahydro-quinoline-4-carboxylic acid (4-chloro-phenyl)-ethyl-amide (11%).

¹H-NMR (CDCl₃) δ: 1.02-1.18 (m, 6H), 1.60-1.70 (m, 1H), 2.45-2.55 (m, 1H), 3.60-3.70 (m, 1H), 3.80 (q, 2H), 4.98-5.10 (m, 1H), 6.40 (d, 1H), 6.90 (m, 2H), 7.00 (t, 1H), 7.30 (m, 2H), 7.50 (d, 2H), 7.60 (d, 2H), 8.55 (d, 2H). MS m/z: 434/436 (M+1).

(±)-trans-1-(4-Methoxy-benzoyl)-2-methyl-1,2,3,4-tetrahydro-quinoline-4-carboxylic acid (4-cyano-phenyl)-ethyl-amide (64)

(±)-trans-1-(4-Methoxy-benzoyl)-2-methyl-1,2,3,4-tetrahydro-quinoline-4-carboxylic acid (4-cyano-phenyl)-ethyl-amide was made following general procedure B, substituting ethyl-(4-cyano-phenyl)-amine for ethyl-benzyl-amine. The crude 1-(4-methoxy-benzoyl)-2-methyl-1,2,3,4-tetrahydro-quinoline-4-carboxylic acid (4-cyano-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (4-cyano-phenyl)-ethyl-amide. ¹H-NMR (CDCl₃) δ: 1.00 (d, 3H), 1.14 (t, 3H), 1.72-1.82 (m, 1H), 2.54-2.62 (m, 1H), 3.66-3.77 (m, 4H), 3.81-3.97 (m, 2H), 5.03-5.13 (m, 1H), 6.48 (d, 1H), 6.74-6.92 (m, 5H), 7.39 (d, 2H), 7.49 (d, 2H), 7.80 (d, 2H). MS m/z: 454 (M⁺).

(±)-trans-1-(4-Methoxy-benzoyl)-2-methyl-1,2,3,4-tetrahydro-quinoline-4-carboxylic acid ethyl-(4-methoxy-phenyl)-amide (65)

(±)-trans-1-(4-Methoxy-benzoyl)-2-methyl-1,2,3,4-tetrahydro-quinoline-4-carboxylic acid ethyl-(4-methoxy-phenyl)-amide was made following general procedure B, substituting ethyl-(4-methoxy-phenyl)-amine for ethyl-benzyl-amine. The crude 1-(4-methoxy-benzoyl)-2-methyl-1,2,3,4-tetrahydro-quinoline-4-carboxylic acid ethyl-(4-methoxy-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-methoxy-phenyl)-amide. ¹H-NMR (CDCl₃) δ: 0.97 (d, 3H), 1.13 (t, 3H), 1.73-1.81 (m, 1H), 2.47-2.56 (m, 1H), 3.63-3.89 (m, 9H), 5.05-5.14 (m, 1H), 6.43 (d, 1H), 6.74-6.92 (m, 5H), 6.98 (d, 2H), 7.18 (d, 2H), 7.52 (d, 2H). MS m/z: 459 (M⁺).

(±)-trans-1-(4-Methoxy-benzoyl)-2-methyl-1,2,3,4-tetrahydro-quinoline-4-carboxylic acid (3,4-dimethyl-phenyl)-ethyl-amide (67)

(±)-trans-1-(4-Methoxy-benzoyl)-2-methyl-1,2,3,4-tetrahydro-quinoline-4-carboxylic acid (3,4-dimethyl-phenyl)-ethyl-amide was made following general procedure B, substituting ethyl-(3,4-dimethyl-phenyl)-amine for ethyl-benzyl-amine. The crude 1-(4-methoxy-benzoyl)-2-methyl-1,2,3,4-tetrahydro-quinoline-4-carboxylic acid (3,4-dimethyl-phenyl)-ethyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid (3,4-dimethyl-phenyl)-ethyl-amide. ¹H-NMR (CDCl₃) δ: 0.97 (d, 3H), 1.15 (t, 3H), 1.94-2.05 (m, 1H), 2.32 (s, 6H), 2.49-2.58 (m, 1H), 3.66-3.77 (m, 4H), 3.84-3.92 (m, 2H), 4.95-5.11 (m, 1H), 6.43 (d, 1H), 6.74-7.13 (m, 6H), 7.43-7.51 (m, 4H). MS m/z: 457 (M⁺).

(±)-trans-1-(4-Methoxy-benzoyl)-2-methyl-1,2,3,4-tetrahydro-quinoline-4-carboxylic acid (4-chloro-phenyl)-isobutyl-amide (69)

(±)-trans-1-(4-Methoxy-benzoyl)-2-methyl-1,2,3,4-tetrahydro-quinoline-4-carboxylic acid (4-chloro-phenyl)-isobutyl-amide was made following general procedure B, substituting (4-chloro-phenyl)-isobutyl-amine for ethyl-benzyl-amine. ¹H-NMR (CDCl₃) δ: 0.90 (d, 6H), 0.96 (d, 3H), 1.69-1.84 (m, 2H), 2.50 (ddd, 1H), 3.51 (dd, 1H), 3.66 (dd, 1H), 3.75 (s, 3H), 3.85 (dd, 1H), 5.02-5.14 (m, 1H), 6.43 (d, 1H), 6.70-6.93 (m, 5H), 7.21-7.26 (m, 2H), 7.42-7.53 (m, 4H). MS m/z=491 (M+1).

(±)-trans-1-(4-Methoxy-benzoyl)-2-methyl-1,2,3,4-tetrahydro-quinoline-4-carboxylic acid ethyl-p-tolyl-amide (70)

(±)-trans-1-(4-Methoxy-benzoyl)-2-methyl-1,2,3,4-tetrahydro-quinoline-4-carboxylic acid ethyl-p-tolyl-amide was made following general procedure B, substituting ethyl-p-tolyl-amine for ethyl-benzyl-amine. ¹H-NMR (CDCl₃) δ: 0.95 (d, 3H), 1.13 (t, 3H), 1.77 (ddd, 1H), 2.40 (s, 3H), 2.51 (ddd, 1H), 3.70 (dd, 1H), 3.75 (s, 3H), 3.81-3.91 (m, 2H), 5.03-5.15 (m, 1H), 6.41 (d, 1H), 6.72-6.83 (m, 3H), 6.83-6.93 (m, 2H), 7.11-7.18 (m, 2H), 7.24-7.31 (m, 2H), 7.49-7.56 (m, 2H). MS m/z=443 (M+1).

(±)-cis-1-(Benzo[b]thiophene-2-carbonyl)-2-methyl-1,2,3,4-tetrahydro-quinoline-4-carboxylic acid (4-chloro-phenyl)-ethyl-amide (71)

Same procedure as for the preparation of (±)-trans-1-(benzo[b]thiophene-2-carbonyl)-2-methyl-1,2,3,4-tetrahydro-quinoline-4-carboxylic acid (4-chloro-phenyl)-ethyl-amide. Purification via HPLC gave (±)-cis-1-(benzo[b]thiophene-2-carbonyl)-2-methyl-1,2,3,4-tetrahydro-quinoline-4-carboxylic acid (4-chloro-phenyl)-ethyl-amide (20%). ¹H-NMR (CDCl₃) δ: 1.18 (d, 3H), 1.25 (t, 3H), 1.70-1.80 (m, 1H), 2.55-2.65 (m, 1H), 3.35-3.45 (dd, 1H), 3.75-3.85 (m, 1H), 4.00-4.15 (m, 1H), 4.60-4.75 (m, 1H), 6.80-6.90 (m, 2H), 7.00 (t, 1H), 7.20-7.30 (m, 3H), 7.30-7.40 (m, 5H), 7.65 (dd, 1H), 7.70 (dd, 1H). MS m/z: 489/491 (M+1).

(±)-trans-1-(4-Methoxy-benzoyl)-2-methyl-1,2,3,4-tetrahydro-quinoline-4-carboxylic acid ethyl-(4-fluoro-phenyl)-amide (72)

(±)-trans-1-(4-Methoxy-benzoyl)-2-methyl-1,2,3,4-tetrahydro-quinoline-4-carboxylic acid ethyl-(4-fluoro-phenyl)-amide was made following general procedure B, substituting ethyl-(4-fluoro-phenyl)-amine for ethyl-benzyl-amine. The crude 1-(4-methoxy-benzoyl)-2-methyl-1,2,3,4-tetrahydro-quinoline-4-carboxylic acid ethyl-(4-fluoro-phenyl)-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid ethyl-(4-fluoro-phenyl)-amide. ¹H-NMR (CDCl₃) δ: 0.96 (d, 3H), 1.13 (t, 3H), 1.69-1.78 (m, 1H), 2.48-2.57 (m, 1H), 3.58-3.72 (m, 1H), 3.75 (s, 3H), 3.78-3.89 (m, 2H), 5.03-5.13 (m, 1H), 6.44 (d, 1H), 6.73-6.81 (m, 4H), 6.86-6.91 (m, 1H), 7.14-7.27 (m, 4H), 7.49 (d, 2H). MS m/z: 447 (M⁺).

rel-(2S,4S)-1-(4-Methoxy-benzoyl)-2-methyl-1,2,3,4-tetrahydro-quinoline-4-carboxylic acid (4-chloro-phenyl)-ethyl-amide (73) and rel-(2R,4R)-1-(4-Methoxy-benzoyl)-2-methyl-1,2,3,4-tetrahydro-quinoline-4-carboxylic acid (4-chloro-phenyl)-ethyl-amide (74)

rel-(2S,4S)- and rel-(2R,4R)-1-(4-Methoxy-benzoyl)-2-methyl-1,2,3,4-tetrahydro-quinoline-4-carboxylic acid (4-chloro-phenyl)-ethyl-amide were isolated from (±)-trans- 1-(4-methoxy-benzoyl)-2-methyl-1,2,3,4-tetrahydro-quinoline-4-carboxylic acid (4-chloro-phenyl)-ethyl-amide by preparative chiral HPLC. Analytical data for the individual enantiomers was identical to the racemate given above.

(±)-trans-1-(4-Methoxy-benzoyl)-2-methyl-1,2,3,4-tetrahydro-quinoline-4-carboxylic acid benzyl-phenyl-amide (77)

(±)-trans-1-(4-Methoxy-benzoyl)-2-methyl-1,2,3,4-tetrahydro-quinoline-4-carboxylic acid benzyl-phenyl-amide was made following general procedure B, substituting N-benzyl-aniline for ethyl-benzyl-amine. The crude 1-(4-methoxy-benzoyl)-2-methyl-1,2,3,4-tetrahydro-quinoline-4-carboxylic acid benzyl-phenyl-amide was isolated as a mixture of cis and trans isomers. Purification via HPLC yielded (±)-trans-1-(4-methoxy-benzoyl)-2-methyl-1,2,3,4-tetrahydro-quinoline-4-carboxylic acid benzyl-phenyl-amide. $^1$H-NMR (CDCl$_3$) δ: 0.96 (d, 3H), 1.76-1.84 (m, 1H), 2.54-2.63 (m, 1H), 3.77 (s, 3H), 3.88-3.93 (m, 1H), 4.95 (dd, 2H), 5.09-5.17 (m, 1H), 6.47 (d, 1H), 6.76-6.95 (m, 5H), 7.06-7.09 (m, 2H), 7.18-7.27 (m, 5H), 7.36-7.39 (m, 3H), 7.54-7.56 (m, 2H). MS m/z: 491 (M$^+$).

(±)-trans-1-(4-Fluoro-benzoyl)-2-methyl-1,2,3,4-tetrahydro-quinoline-4-carboxylic acid (4-chloro-phenyl)-ethyl-amide (78)

(±)-trans-1-(4-Fluoro-benzoyl)-2-methyl-1,2,3,4-tetrahydro-quinoline-4-carboxylic acid (4-chloro-phenyl)-ethyl-amide was made following general procedure A, substituting 4-fluoro-benzoyl chloride for 4-trifluoromethyl-benzoyl chloride. The crude 1-(4-fluoro-benzoyl)-2-methyl-1,2,3,4-tetrahydro-quinoline-4-carboxylic acid (4-chloro-phenyl)-ethyl-amide was isolated as a mixture of cis and trans isomers. Purification via HPLC yielded (±)-trans-1-(4-fluoro-benzoyl)-2-methyl-1,2,3,4-tetrahydro-quinoline-4-carboxylic acid (4-chloro-phenyl)-ethyl-amide (28%). $^1$H-NMR (CDCl$_3$) δ: 0.96 (d, 3H), 1.13 (t, 3H), 1.71-1.80 (m, 1H), 2.45-2.56 (m, 1H), 3.65 (m, 1H), 3.79-3.90 (m, 2H), 4.98-5.10 (m, 1H), 6.37-6.40 (d, 1H), 6.78-6.83 (t, 2H), 6.68-6.94 (t, 3H), 7.19-7.23 (t, 2H), 7.41-7.49 (d, 2H), 7.53-7.57 (m, 2H). MS m/z: 451 (M+1).

(±)-trans-4-(4-{[4-{[(4-Chlorophenyl)(ethyl)amino]carbonyl}-2-methyl-3,4-dihydroquinolin-1(2H)-yl]carbonyl}phenoxy)-2,2-difluorobutanoic acid (84)

Step 1. (±)-trans-Ethyl 4-(4-{[4-{[(4-chlorophenyl)(ethyl)amino]carbonyl}-2-methyl-3,4-dihydroquinolin-1(2H)-yl]carbonyl}phenoxy)-2,2-difluorobutanoate. Ethyl 2,2-difluoro-4-hydroxybutanoate (U.S. Pat. No. 4,421,690, 20 Dec. 1983) (314 mg, 1.9 mmol) and triphenylphosphine (262 mg, 1.9 mmol) were dissolved in toluene (10 mL) at room temperature. (±)-trans-1-(4-Hydroxy-benzoyl)-1,2,3,4-tetrahydro-quinoline-4-carboxylic acid (4-chloro-phenyl)-ethyl-amide (119 mg, 0.27 mmol) was added to the resulting mixture, followed by diethyl azodicarboxylate (323 mg, 1.9 mmol). The reaction mixture was stirred for 18 hours at room temperature and concentrated under reduced pressure. The crude residue was purified by silica gel chromatography (ethyl acetate/dichloromethane gradient) to afford crude (±)-trans-ethyl 4-(4-{[4-{[(4-chlorophenyl)(ethyl)amino]carbonyl}-2-methyl-3,4-dihydroquinolin-1(2H)-yl]carbonyl}phenoxy)-2,2-difluorobutanoate as yellow solid (190 mg). The crude material was used directly in the next step. MS m/z: 599 (M+1).

Step 2. (±)-trans-4-(4-{[4-{[(4-Chlorophenyl)(ethyl)amino]carbonyl}-2-methyl-3,4-dihydroquinolin-1(2H)-yl]carbonyl}phenoxy)-2,2-difluorobutanoic acid.

To a solution of (±)-trans-ethyl 4-(4-{[4-{[(4-chlorophenyl)(ethyl)amino]carbonyl}-2-methyl-3,4-dihydroquinolin-1(2H)-yl]carbonyl}phenoxy)-2,2-difluorobutanoate (190 mg, 0.32 mmol) in THF (4.4 mL) was added a solution of lithium hydroxide (15.2 mg, 0.63 mmol) in water (2 mL). To the resulting mixture was added methanol (2 mL) and the reaction stirred 18 hours at room temperature. The reaction mixture pH was adjusted to 2 via addition of 1N hydrochloric acid and extracted with ethyl acetate (3×25 mL). The combined organic layers were washed with brine, dried over magnesium sulfate and concentrated in vacuo to yield (±)-trans-4-(4-{[4-{[(4-chlorophenyl)(ethyl)amino]carbonyl}-2-methyl-3,4-dihydroquinolin-1(2H)-yl]carbonyl}phenoxy)-2,2-difluorobutanoic acid. $^1$H-NMR (CDCl$_3$) δ: 0.96 (d, 3H), 1.08 (t, 3H), 1.61-1.74 (m, 1H), 2.34-2.56 (m, 3H), 3.52-3.68 (m, 1H), 3.72-3.88 (m, 2H), 4.00-4.14 (m, 2H), 4.93-5.11 (m, 1H), 6.42-6.51 (m, 1H), 6.65-6.82 (m, 4H), 6.83-6.92 (m, 1H), 7.16-7.29 (m, 2H), 7.37-7.50 (m, 4H). MS m/z: 571 (M+1).

(±)-trans-N-Cyclopropyl-N-ethyl-1-(4-methoxybenzoyl)-2-methyl-1,2,3,4-tetrahydroquinoline-4-carboxamide (83)

(±)-trans-N-Cyclopropyl-N-ethyl-1-(4-methoxybenzoyl)-2-methyl-1,2,3,4-tetrahydroquinoline-4-carboxamide was made following general procedure A, substituting 4-methoxybenzoyl chloride for 4-trifluoromethyl-benzoyl chloride and N-ethylcyclopropanamine for N-ethyl-p-chloroaniline. N-Ethylcyclopropanamine was prepared by the reductive amination of cyclopropylamine using acetaldehyde and sodium triacetoxyborohydride in dichloromethane. The crude N-cyclopropyl-N-ethyl-1-(4-methoxybenzoyl)-2-methyl-1,2,3,4-tetrahydroquinoline-4-carboxamide was isolated as a mixture of cis and trans isomers. Purification via HPLC yielded (±)-trans-N-cyclopropyl-N-ethyl-1-(4-methoxybenzoyl)-2-methyl-1,2,3,4-tetrahydroquinoline-4-carboxamide. $^1$H-NMR (CDCl$_3$) δ: 0.81-0.95 (m, 2H), 0.96-1.07 (m, 2H), 1.17 (t, 3H), 1.21 (d, 3H), 1.95-2.07 (m, 1H), 2.41-2.55 (m, 1H), 2.80-2.92 (m, 1H), 3.38-3.64 (m, 2H), 3.75 (s, 3H), 4.68-4.82 (m, 1H), 5.08-5.23 (m, 1H), 6.44-6.53 (m, 1H), 6.70-6.84 (m, 3H), 6.88-7.01 (m, 2H), 7.45-7.55 (m, 2H). MS m/z: 393 (M+1).

(±)-trans-N-(4-Chlorophenyl)-1-(cyclopropylcarbonyl)-N-ethyl-2-methyl-1,2,3,4-tetrahydroquinoline-4-carboxamide (82)

(±)-trans-N-(4-Chlorophenyl)-1-(cyclopropylcarbonyl)-N-ethyl-2-methyl-1,2,3,4-tetrahydroquinoline-4-carboxamide was made following general procedure A, substituting cyclopropanecarbonyl chloride for 4-trifluoromethyl-benzoyl chloride. The crude N-(4-chlorophenyl)-1-(cyclopropylcarbonyl)-N-ethyl-2-methyl-1,2,3,4-tetrahydroquinoline-4-carboxamide was isolated as a mixture of cis and trans isomers. Purification via HPLC yielded (±)-trans-N-(4-chlorophenyl)-1-(cyclopropylcarbonyl)-N-ethyl-2-methyl-1,2,3,4-tetrahydroquinoline-4-carboxamide. $^1$H-NMR (CDCl$_3$) δ: 0.63-0.74 (m, 1H), 0.79-1.00 (m, 2H), 0.90 (d, 3H), 1.07 (t, 3H), 1.21-1.31 (m, 1H), 1.46-1.56 (m, 1H), 1.85-1.98 (m, 1H), 2.43-2.58 (m, 1H), 3.55-3.86 (m, 3H), 4.97-5.09 (m, 1H), 6.64-6.69 (m, 1H), 6.93-7.01 (m, 1H), 7.03-7.08 (m, 2H), 7.09-7.16 (m, 1H), 7.24-7.29 (m, 1H), 7.34-7.39 (m, 2H). MS m/z: 397 (M+1).

N-Ethyl-N-isopropyl-1-(4-methoxybenzoyl)-2-methyl-1,2,3,4-tetrahydroquinoline-4-carboxamide (81)

N-Ethyl-N-isopropyl-1-(4-methoxybenzoyl)-2-methyl-1,2,3,4-tetrahydroquinoline-4-carboxamide was made following general procedure B, substituting N-ethylpropan-2-amine for ethyl-benzyl-amine. Purification via HPLC yielded N-ethyl-N-isopropyl-1-(4-methoxybenzoyl)-2-methyl-1,2,3,4-tetrahydroquinoline-4-carboxamide as a mixture of cis and trans isomers. MS m/z: 395 (M+1).

rel-(2S,4S)-5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid (80) and rel-(2R,4R)-5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid (79)

Step 1. Methyl 5-[4-(chlorocarbonyl)phenyl]-2,2-dimethylpentanoate 2,2-Dimethyl-4-pentanoic acid (2 g, 15.6 mmol, 1.0 eq.) was dissolved in anhydrous methanol (40 ml). The solution was cooled down to 0° C.; a 2 M solution of trimethylsilyl diazomethane in hexanes (11 ml, 21.8 mmol, 1.4 eq.) was added slowly until the reaction mixture turned slight yellow indicating the reaction was complete. Reaction mixture was concentrated down to give methyl-2,2-dimethyl-4-pentanoate as a colorless oil (2 g, 91%).

Methyl-2,2-dimethyl-4-pentanoate (1.0 g, 7.0 mmol, 1 eq.) was dissolved in anhydrous dimethylformamide. The solution was purged with nitrogen, and 4-iodobenzoic acid (1.7 g, 7.0 mmol, 1 eq.), triethylamine (1.1 ml, 7.7 mmol, 1.1 eq.) and palladium acetate (79 mg, 0.35 mmol, 0.05 eq.) were sequentially added. Reaction was then heated to 80° C. under nitrogen for 18 h. Reaction mixture was concentrated under vacuo to leave a black oil which was partitioned between water and ethyl acetate and extracted. The aqueous layer was separated and the organic layer was washed with brine, dried over magnesium sulfate, filtered and concentrated to give a dark brown solid. The crude product was purified by silica gel chromatography (methylene chloride/methanol: 98/2→96/4 gradient) to provide 4-(4-methoxycarbonyl-4-methyl-pent-1-enyl)-benzoic acid as a light brown solid (915 mg, 50%).

4-(4-Methoxycarbonyl-4-methyl-pent-1-enyl)-benzoic acid (900 mg, 3.4 mmol, 1 eq.) was dissolved in ethanol (13 ml) and triethylamine (568 µl, 4.1 mmol, 1.2 eq.) and palladium on carbon (90 mg, 10% Pd/C) were then added. The mixture was stirred under hydrogen atmosphere for 20 h. Reaction mixture was filtered over celite and washed with ethanol. The filtrate was evaporated to yield a yellow oil. This oil was dissolved in ethyl acetate and washed with a 1N aqueous hydrochloric acid solution. The aqueous layer was removed and the organic layer was washed with water, and brine, then dried over magnesium sulfate, filtered and concentrated to give 4-(4-methoxycarbonyl-4-methyl-pentyl)-benzoic acid (763 mg, 85%).

4-(4-Methoxycarbonyl-4-methyl-pentyl)-benzoic acid (763 mg, 2.9 mmol, 1 eq.) was dissolved in methylene chloride (9 ml) and the solution was cooled down to 0° C. A 2 M solution of oxalyl chloride in methylene chloride (2.9 ml, 5.8 mmol, 2.0 eq.) was added followed by a catalytic amount of dimethylformamide. The reaction mixture was stirred at rt for 1 h, then concentrated to give the acid chloride as an oil. Methyl 5-[4-(chlorocarbonyl)phenyl]-2,2-dimethylpentanoate was used without further purification in subsequent steps.

Step 2. (±)-trans-Methyl 5-(4-{[4-{[(4-chlorophenyl)(ethyl)amino]carbonyl}-2-methyl-3,4-dihydroquinolin-1(2H)-yl]carbonyl}phenyl)-2,2-dimethylpentanoate (±)-trans-Methyl 5-(4-{[4-{[(4-chlorophenyl)(ethyl)amino]carbonyl}-2-methyl-3,4-dihydroquinolin-1(2H)-yl]carbonyl}phenyl)-2,2-dimethylpentanoate was made following general procedure A, substituting methyl 5-[4-(chlorocarbonyl)phenyl]-2,2-dimethylpentanoate for 4-trifluoromethyl-benzoyl chloride. Purification via silica gel chromatography (0-40% ethyl acetate/hexane gradient) yielded (±)-trans-methyl 5-(4-{[4-{[(4-chlorophenyl)(ethyl)amino]carbonyl}-2-methyl-3,4-dihydroquinolin-1(2H)-yl]carbonyl}phenyl)-2,2-dimethylpentanoate. MS m/z: 575 (M+1).

Step 3. (±)-trans-5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid To a solution of (±)-trans-methyl 5-(4-{[4-{[(4-chlorophenyl)(ethyl)amino]carbonyl}-2-methyl-3,4-dihydroquinolin-1(2H)-yl]carbonyl}phenyl)-2,2-dimethylpentanoate (500 mg, 0.87 mmol) in 1:1 THF/methanol (5.0 mL) was added a solution of sodium hydroxide (69.5 mg, 1.74 mmol) in water (1.0 mL). The resulting mixture was heated at 60° C. for 18-20 hours and concentrated. The resulting residue was dissolved in water (~50 mL), cooled to 0° C., and the solution acidified using 3N hydrochloric acid. The resulting precipitated material was collected via suction filtration, washed with 1N hydrochloric acid (3×25 mL), and dried to afford crude 5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid as a mixture of cis and trans isomers. Purification via HPLC yielded (±)-trans-5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid (23%).

Step 4. rel-(2S,4S)-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid and rel-(2R,4R)-(4-{[4-{[(4-chlorophenyl)(ethyl)amino]carbonyl}-2-methyl-3,4-dihydroquinolin-1(2H)-yl]carbonyl}phenyl)-2,2-dimethylpentanoic acid rel-(2S,4S)-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid and rel-(2R,4R)-(4-{[4-{[(4-chlorophenyl)(ethyl)amino]carbonyl}-2-methyl-3,4-dihydroquinolin-1(2H)-yl]carbonyl}phenyl)-2,2-dimethylpentanoic acid were isolated from (±)-trans-5-(4-{[4-{[(4-Chlorophenyl)(ethyl)amino]carbonyl}-2-methyl-3,4-dihydroquinolin-1(2H)-yl]carbonyl}phenyl)-2,2-dimethylpentanoic acid by preparative chiral HPLC. Data for single enantiomer (identical to enantiomer and to racemate), absolute stereochemistry unknown: $^1$H-NMR (CD$_3$Cl) δ: 0.95 (d, 3H), 1.12 (t, 3H), 1.14 (s, 6H), 1.30-1.43 (m, 1H), 1.45-1.59 (m, 4H), 1.67-1.77 (m, 1H), 2.47-2.63 (m, 2H), 3.58-3.74 (m, 1H), 3.76-3.92 (m, 2H), 5.01-5.16 (m, 1H), 6.40-6.50 (m, 1H), 6.70-6.81 (m, 2H), 6.84-6.94 (m, 1H), 6.99-7.08 (m, 2H), 7.17-7.21 (m, 2H), 7.40-7.52 (m, 4H). MS m/z: 561 (M+1).

Compounds 85-207, as shown in Table 1, can be prepared by the schemes set forth in Schemes 1-3 and by the general procedures A and B and others described herein. Those skilled in the art will be able to recognize, or be able to ascertain, using no more than routine experimentation, many equivalents to the specific embodiments of the invention described herein.

Biological Testing

This radioligand membrane binding assay evaluates the ability of compounds to inhibit [$^3$H] Prostaglandin D$_2$ (PGD$_2$) binding to the cloned human CRTH2 receptor stably expressed in HEK-293 cells (expressing human CRTh2 receptor and α subunit or the heterotrimeric G protein 16 were prepared by Biosignal Company) using Scintillation Proximity Assay.

A binding buffer containing 50 mM Tris-HCl (pH 7.5), 5 mM MgCl$_2$ and 1 mM EDTA is prepared immediately prior to performing the assay. A bead/membrane solution at twice the final assay concentration comprising membranes (membranes bought from Biosignal) from the HEK-293 cells cloned to express CRTH2 receptor bound to and [$^3$H] PGD$_2$ at two times the final assay concentration are prepared and stored on ice before adding to wells. Cold PGD$_2$ at twenty times the final assay concentration is prepared and stored on ice before adding to wells defining non-specific binding (NSB) coming plates #3653 are used for this assay.

10 mM stock concentrations of compounds in 100% DMSO are prepared and stored at room temperature. A 10 point concentration response curve is then constructed for each compound, starting at 10 μM (final assay concentration). The compounds are prepared at 40 times final assay concentrations with nine consequent-3-fold dilutions.

0.1 μl of each concentration of compound are added to the appropriate well of the 384 plate and 2 μl of cold PGD$_2$ is added into the wells defining NSB. 20 μl of [3H] PGD$_2$ and then 20 μl of 2× of bead/membrane solution are then added to each well.

The plates are allowed to incubate at room temperature for approximately 2 hours and then counted on Packard Topcount using SPA tritium protocol for 1 minute/well.

The percent inhibition of PGD$_2$ binding (PGD$_2$ used at the K$_D$ value or lower) to the HEK-293 cell membranes is determined, the assay is always run as duplicate for n=1 for a total of n=2 and shown below.

Compounds 1, 3, 6, 7, 9, 12, 13, 17-20, 22, 24-27, 30-32, 34, 36, 37, 40, 42, 45, 47, 48, 51, 55, 56, 58, 62-65, 67, 70, 72, 75, 77-78, 81-84 have K$_i$<10 uM.

Compounds 2, 5, 11, 15, 33, 35, 50, 57, 61, 76 have K$_i$<10 uM.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound represented by the following structural formula:

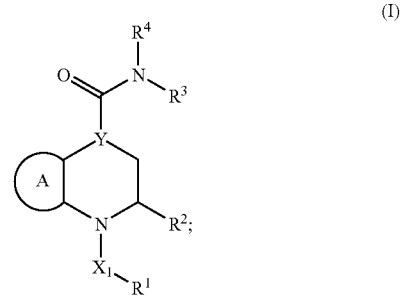

or a pharmaceutically acceptable salt thereof, wherein:

Ring A is an optionally substituted, fused 5-6 membered aryl or heteroaryl ring;

Y is >C(R$^x$)—;

X$_1$ is —C(=O)—, —SO$_2$—, —CONR—, —C(R)$_2$—, or —CO$_2$—,

R$^1$ is an optionally substituted group selected from a monocyclic or bicyclic aryl, a monocyclic or bicyclic heteroaryl, a monocyclic or bicyclic non-aromatic heterocyclic, or a monocyclic or bicyclic non-aromatic carbocylic group;

R$^2$ is a C$_1$-C$_3$ alkyl group, a C$_1$-C$_3$ haloalkyl group or C$_3$-C$_6$ cycloalkyl group wherein the C$_1$-C$_3$ alkyl group represented by R$^2$ is optionally substituted with R$^5$;

R$^3$ is hydrogen, C$_1$-C$_6$ alkyl optionally substituted by R$^6$, C$_1$-C$_6$ fluoroalkyl, or an optionally substituted group selected from a C$_3$-C$_8$ cycloalkyl, a monocyclic non-aromatic heterocyclic, a monocyclic aryl, or a monocyclic heteroaryl group;

R$^4$ is —[C(R$^7$)$_2$]$_m$—B; or R$^3$ and R$^4$ may be taken together with the intervening nitrogen atom to form an optionally substituted monocyclic or bicyclic heteroaryl or non-aromatic heterocyclic group; or R$^x$ and R$^4$ may be taken together with the intervening carbon and nitrogen atoms to form an optionally substituted monocyclic non-aromatic nitrogen-containing heterocyclic group;

R$^5$ is —OH, —O(C$_{1-4}$ aliphatic), —COOR' or —N(R')$_2$;

R$^6$ is —OH, —O(C$_{1-4}$aliphatic), —N(R')$_2$, —C(O)R', —COOR', C(O)N(R')$_2$, or an optionally substituted group selected from a monocyclic cycloalkyl, a monocyclic aryl, a monocyclic heteroaryl, or a monocyclic non-aromatic heterocyclic group;

each R$^7$ is independently hydrogen, fluoro, or C$_1$-C$_3$ alkyl;

each R, R$^x$ or R' is independently hydrogen or a C$_1$-C$_4$ aliphatic group or N(R')$_2$ is a monocyclic non-aromatic nitrogen-containing heterocyclic group;

m is zero or one; and

B is —H, —C(R$^7$)$_3$, —C(R$^7$)$_2$—C(R$^7$)$_3$, or an optionally substituted group selected from a monocyclic or bicyclic cycloalkyl, a monocyclic or bicyclic aryl, a monocyclic or bicyclic heteroaryl, or a monocyclic or bicyclic non-aromatic heterocyclic group.

2. The compound of claim 1 wherein the compound is represented by the following structural formula:

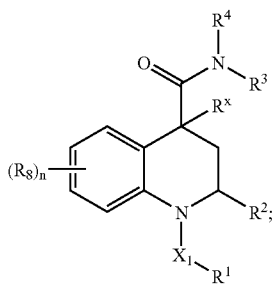

or a pharmaceutically acceptable salt thereof, wherein:
n is 0 or an integer from 1-4;
each $R^8$ is independently halo, —$OR^9$, —$SR^9$, —CN, —$NO_2$, —$N(R^{10})_2$, —$N(R^{10})C(O)R^9$, —$N(R^{10})CO_2R^{9a}$, —$N(R^{10})C(O)N(R^{10})_2$, —$C(O)N(R^{10})_2$, —$OC(O)R^9$, —$OC(O)N(R^{10})_2$, —$C(O)R^9$, —$CO_2R^9$, —$SO_2R^{9a}$, —$S(O)R^{9a}$, —$SO_2N(R^{10})_2$, —$N(R^{10})SO_2R^{9a}$ or an optionally substituted group selected from a $C_{1-8}$ aliphatic, a monocyclic aryl, a monocyclic heteroaryl, or a monocyclic non-aromatic heterocyclic group;
each $R^9$ is independently hydrogen or an optionally substituted $C_{1-6}$ aliphatic group;
each $R^{9a}$ is independently an optionally substituted $C_{1-6}$ aliphatic group; and
each $R^{10}$ is independently hydrogen, a $C_{1-6}$ aliphatic group, —$CO_2R^{9a}$, —$SO_2R^{9a}$, or —$C(O)R^9$, or $N(R^{10})_2$ is a monocyclic heteroaryl or a monocyclic non-aromatic heterocyclic group.

3. The compound of claim 2 wherein the compound is represented by the following structural formula:

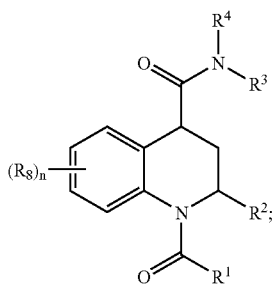

or a pharmaceutically acceptable salt thereof.
4. The compound of claim 3 wherein:
$R^1$ is an optionally substituted monocyclic or bicyclic aryl or heteroaryl group optionally substituted at any one or more substitutable ring carbon atoms with $R^{11}$;
each $R^{11}$ is independently halo, —$OR^{12}$, —$SR^{12}$, —CN, —$NO_2$, —$N(R^{12}R^{13})$, —$N(R^{13})C(O)R^{12}$, —$N(R^{13})CO_2R^{12a}$, —$N(R^{13})C(O)N(R^{12}R^{13})$, —$C(O)N(R^{12}R^{13})$, —$OC(O)R^{12}$, —$OC(O)N(R^{12}R^{13})$, —$C(O)R^{12}$, —$CO_2R^{12}$, —$SO_2R^{12a}$, —$S(O)R^{12a}$, —$SO_2N(R^{12}R^{13})$, —$N(R^{13})SO_2R^{12a}$, an optionally substituted group selected from a $C_{1-8}$ aliphatic, a monocyclic aryl, a monocyclic heteroaryl, or a monocyclic non-aromatic group;
each $R^{12}$ is independently hydrogen or an optionally substituted $C_{1-6}$ aliphatic group;

each $R^{12a}$ is an optionally substituted $C_{1-6}$ aliphatic group; and
each $R^{13}$ is independently hydrogen, a $C_{1-6}$ aliphatic group, —$CO_2R^{12a}$, —$SO_2R^{12a}$, or —$C(O)R^{12}$, or —$N(R^{12}R^{13})$ is a monocyclic heteroaryl or non-aromatic heterocyclic group.

5. The compound of claim 4 wherein:
B is a monocyclic aryl or heteroaryl group, or a monocyclic cycloalkyl group, each optionally substituted at any one or more substitutable ring carbon atoms with $R^{14}$; and
each $R^{14}$ is independently $C_1$-$C_4$ alkyl, $C_1$-$C_4$ haloalkyl, $C_1$-$C_4$ haloalkoxy, $R^{14a}$, $R^{14b}$, -T-$R^{14a}$, -T-$R^{14b}$, —V-$T_1$-$R^b$, —V-T-$R^{14a}$, —$V_1$-T-$R^{14a}$ or —$V_1$-$T_1$-$R^{14b}$;
V is —O—, —N(R)—, —C(O)N(R)— or —S(O)$_2$N(R)—;
$V_1$ is —S(O)$_2$, —C(O)—, —N(R)C(O)— or —N(R)SO$_2$—;
T is a $C_1$-$C_4$ optionally substituted alkylene;
$T_1$ is a $C_2$-$C_4$ optionally substituted alkylene;
each $R^{14a}$ is independently selected from —$OR^{15a}$, —$SR^{15a}$, —$C(O)N(R^{16})_2$, —$C(O)R^{15}$, —$CO_2R^{15}$, —$SO_2R^{15a}$, —$S(O)R^{15a}$, —$SO_2N(R^{16})_2$, an optionally substituted monocyclic aryl or heteroaryl group or an optionally substituted monocyclic non-aromatic heterocyclic group;
each $R^{14b}$ is independently selected from halo, —OH, —SH, —CN, —$NO_2$, —$N(R^{16})_2$, —$N(R^{16})C(O)R^{15}$, —$N(R^{16})CO_2R^{15a}$, —$N(R^{16})C(O)N(R^{16})_2$, —$OC(O)R^{15}$, —$OC(O)N(R^{16})_2$ or —$N(R^{16})SO_2R^{15a}$,
each $R^{15}$ is independently hydrogen or a $C_{1-6}$ aliphatic group;
each $R^{15a}$ is a $C_{1-6}$ aliphatic group; and
each $R^{16}$ is independently selected from hydrogen, a $C_{1-6}$ aliphatic group, —$CO_2R^{15a}$, —$SO_2R^{15a}$, or —$C(O)R^{15}$, or $N(R^{16})_2$ is a monocyclic heteroaryl or a monocyclic non-aromatic heterocyclic group.

6. The compound of claim 5 wherein
$R^2$ is $C_1$-$C_2$ alkyl or $C_3$-$C_6$ cycloalkyl;
$R^3$ is a $C_1$-$C_4$ alkyl group, and
$R^4$ is —(CH$_2$)$_m$—B.

7. The compound of claim 6 wherein $R^1$ is a phenyl, pyridyl, pyrimidyl, oxazolyl, isoxazolyl, thiazolyl, isothiazolyl, furanyl, thiophenyl, imidazolyl, pyrazolyl, pylori, tetrazolyl, indolyl, benzotriazolyl, benzothiazolyl, benzimidazolyl, benzothienyl, benzofuranyl, benzmorpholinyl or benzpiperazinyl, each optionally substituted at any one or more substitutable ring carbon atoms with $R^{11}$.

8. The compound of claim 7 wherein —C(O)NR$^3$R$^4$ and —R$^2$ are trans relative to one another.

9. The compound of claim 8 wherein the compound is represented by the following structural formula:

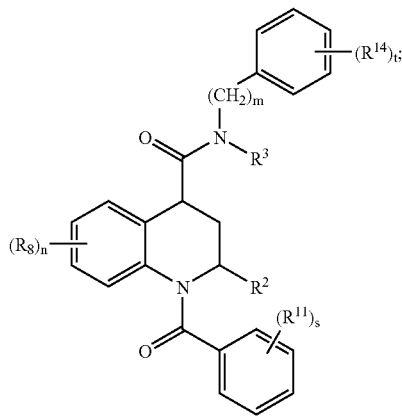

or a pharmaceutically acceptable salt thereof, wherein s and t are independently 0, 1, 2, 3 or 4.

10. The compound of claim 9 wherein $R^8$, $R^{11}$ and $R^{14}$, when present, are independently, halo, $CO_2R^{12}$, $CONR^{12}R^{13}$, $C_{1-3}$ alkyl, $C_{1-3}$ haloalkyl, hydroxyl, $C_{1-3}$ alkoxy, $C_{1-3}$ haloalkoxy, —CN, amine, $C_{1-3}$ alkyl amine, $C_{1-3}$ dialkylamine, $C_{1-3}$ hydroxyalkyl or $C_{1-3}$ aminoalkyl.

11. The compound of claim 3, wherein:
$R^1$ is a monocyclic aryl or heteroaryl group substituted with $T_2$-$V_2$-$T_3$-M-$R^Y$ and is further optionally substituted at any one or more substitutable ring carbon atoms with $R^{11}$;
each $R^{11}$ is independently halo, —$OR^{12}$, —$SR^{12}$, —CN, —$NO_2$, —$N(R^{12}R^{13})$, —$N(R^{13})C(O)R^{12}$, —$N(R^{13})CO_2R^{12a}$, —$N(R^{13})C(O)N(R^{12}R^{13})$, —$C(O)N(R^{12}R^{13})$, —$OC(O)R^{12}$, —$OC(O)N(R^{12}R^{13})$, —$C(O)R^{12}$, —$CO_2R^{12}$, —$SO_2R^{12a}$, —$S(O)R^{12a}$, —$SO_2N(R^{12}R^{13})$, —$N(R^{13})SO_2R^{12a}$, an optionally substituted group selected from a $C_{1-8}$ aliphatic, a monocyclic aryl, a monocyclic heteroaryl, or a monocyclic non-aromatic group;
each $R^{12}$ is independently hydrogen or an optionally substituted $C_{1-6}$ aliphatic group;
each $R^{12a}$ is an optionally substituted $C_{1-6}$ aliphatic group; and
each $R^{13}$ is independently hydrogen, a $C_{1-6}$ aliphatic group, —$CO_2R^{12a}$, —$SO_2R^{12a}$, or —$C(O)R^{12}$, or —$N(R^{12}R^{13})$ is a monocyclic heteroaryl or non-aromatic heterocyclic group;
$R^Y$ is —$C(O)OR^{18}$, —$C(O)R^{18}$, —$OC(O)R^{18}$, —$C(O)N(R^{19})_2$, —$NR^{19}C(O)R^{18}$, —$NR^{19}C(O)OR^{18a}$, —$S(O)_2R^{18a}$, —$S(O)_2COR^{18}$, —$S(O)_2N(R^{19})_2$, —$NR^{19}S(O)_2R^{18a}$, —$NR^{19}S(O)_2R^{18a}$, $S(O)_2OR^{18}$, —$S(O)OR^{18}$, —$S(O)R^{18a}$, —$SR^{18}$, —$C(O)NR^{19}S(O)_2R^{18a}$, —CN, —$NR^{19}C(O)N(R^{19})_2$, —$OC(O)N(R^{19})_2$, —$N(R^{19})_2$, —$OR^{18}$, an optionally substituted non-aromatic heterocyclic group or an optionally substituted heteroaryl group;
M is absent or an optionally substituted monocyclic arylene, an optionally substituted monocyclic non-aromatic carbocyclene or an optionally substituted monocyclic non-aromatic heterocyclene;
$V_2$ is absent, —O—, —C(O)—, —$N(R^{19})$—, —S—, —S(O)—, —$C(O)NR^{19}$—, —$NR^{19}C(O)$—, —$S(O)_2NR^{19}$—, —$NR^{19}S(O)_2$—, or —$S(O)_2$—;
$T_2$ is absent, or a $C_{1-10}$ straight chain alkylene;
$T_3$ is $C_{1-10}$ is a straight chain alkylene; provided that $T_3$ is a $C_{2-10}$ straight chained alkylene when M is absent and $V_2$ is —O—, —S—, —$N(R^{19})$—, —$C(O)N(R^{19})$— or —$S(O)_2N(R^{19})$— and $R^Y$ is —$NR^{19}S(O)_2R^{18a}$, —$NR^{19}S(O)_2R^{18a}$, —$NR^{19}C(O)R^{18}$, —$NR^{19}C(O)OR^{18a}$, —$NR^{19}C(O)NR^{19}_2$, —CN, —OH, —SH, —$N(R^{19})_2$;
wherein $T_2$ and $T_3$ together contain no more than 10 carbon atoms, and wherein $T_2$ and $T_3$ are optionally and independently substituted at any one or more substitutable carbon atoms with halide, alkyl, gem dialkyl, gem dihalo, haloalkyl, alkoxy, haloalkoxy, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;
each $R^{18}$ is independently hydrogen or $C_{1-6}$ aliphatic group;
each $R^{18a}$ is independently $C_{1-6}$ aliphatic group; and
each $R^{19}$ is independently selected from hydrogen, a $C_{1-6}$ aliphatic group, —$CO_2R^{18}$, —$SO_2R^{18}$, or —$C(O)R^{18}$, or —$NR^{19}$ is a monocyclic heteroaryl or a monocyclic non-aromatic heterocyclic group.

12. The compound of claim 11 wherein $T_2$ and M are absent.

13. The compound of claim 12 wherein:
B is a monocyclic aryl or heteroaryl group or a monocyclic cycloalkyl group, each optionally substituted at any one or more substitutable ring carbon atoms with $R^{14}$;
each $R^{14}$ is independently $C_1$-$C_4$ alkyl, $C_1$-$C_4$ haloalkyl, $C_1$-$C_4$ haloalkoxy, $R^{14a}$, $R^{14b}$, -T-$R^{14a}$, -T-$R^{14b}$, —V-T-$R^{14a}$, —V-$T_1$-$R^{14b}$, —$V_1$-T-$R^{14a}$ or —$V_1$-$T_1$-$R^{14b}$;
V is —O—, —N(R)—, —C(O)N(R)— or —$S(O)_2N(R)$—;
$V_1$ is —$S(O)_2$, —C(O)—, —N(R)C(O)— or —$N(R)SO_2$—;
T is a $C_1$-$C_4$ optionally substituted alkylene;
$T_1$ is a $C_2$-$C_4$ optionally substituted alkylene;
each $R^{14a}$ is independently selected from –$OR^{15a}$, —$SR^{15a}$, —$C(O)N(R^{16})_2$, —$CO_2R^{15}$, —$SO_2R^{15a}$, —$S(O)R^{15a}$, —$SO_2N(R^{16})_2$, an optionally substituted monocyclic aromatic group or an optionally substituted monocyclic non-aromatic heterocyclic group;
each $R^{14b}$ is independently selected from halo, —OH, —SH, —CN, —$NO_2$, —$N(R^{16})_2$, —$N(R^{16})C(O)R^{15}$, —$N(R^{16})CO_2R^{15a}$ or —$N(R^{16})C(O)N(R^{16})_2$, —$OC(O)R^{15}$, —$OC(O)N(R^{16})_2$ or —$N(R^{16})SO_2R^{15a}$;
each $R^{15}$ is independently hydrogen or a $C_{1-6}$ aliphatic group;
each $R^{15a}$ is a $C_{1-6}$ aliphatic group; and
each $R^{16}$ is independently selected from hydrogen, a $C_{1-6}$ aliphatic group, —$CO_2R^{15a}$, —$SO_2R^{15a}$, or —$C(O)R^{15}$, or $N(R^{16})_2$ is a monocyclic heteroaryl or a monocyclic non-aromatic heterocyclic group.

14. The compound of claim 13 wherein:
$R^2$ is $C_1$-$C_2$ alkyl or $C_3$-$C_6$ cycloalkyl;
$R^3$ is a $C_1$-$C_4$alkyl group, and
$R^4$ is —$(CH_2)_m$—B.

15. The compound of claim 14 wherein $R^1$ is a phenyl, pyridyl, pyrimidyl, oxazolyl, isoxazolyl, thiazolyl, isothiazolyl, furanyl, thiophenyl, imidazolyl, pyrazolyl, pyrollyl, tetrazolyl, indolyl, benzotriazolyl, benzothiazolyl, benzimidazolyl, benzothienyl, benzofuranyl, benzmorpholinyl or benzpiperazinyl, each substituted with —$V_2$-$T_3$-$R^Y$, and each optionally substituted at any one or more substitutable ring carbon atoms with $R^{11}$.

16. The compound of claim 15 wherein the compound is represented by structural formula:

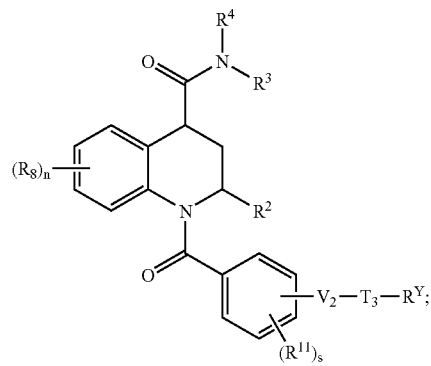

or a pharmaceutically acceptable salt thereof, wherein s is 0, 1, 2, 3, or 4.

17. The compound of claim 16 wherein —$C(O)NR^3R^4$ and —$R^2$ are trans relative to one another.

18. The compound of claim 17 wherein the compound is represented by the following structural formula:

or a pharmaceutically acceptable salt thereof.

19. The compound of claim 18 wherein:

$V_2$ is a covalent bond or —O—;

$T_3$ is $C_{1-6}$ is a straight chain alkylene optionally substituted at any one or more substitutable carbon atoms with halide, alkyl, gem dialkyl, gem dihalo, haloalkyl, spiro cycloalkyl, optionally N-substituted nitrogen containing spiro non-aromatic heterocyclic group, oxygen-containing spiro non-aromatic heterocyclic group, amine, alkylamine, dialkylamine, or hydroxyl;

$R^Y$ is —C(O)OR$^{18}$, —C(O)N(R$^{19}$)$_2$, —NR$^{19}$C(O)R$^{18}$, —NR$^{19}$C(O)OR$^{18a}$, —S(O)$_2$N(R$^{19}$)$_2$, —NR$^{19}$S(O)$_2$R$^{18a}$, —NR$^{19}$C(O)N(R$^{19}$)$_2$,) an optionally substituted non-aromatic heterocyclic group represented by $R^{20}$ or an optionally substituted heteroaryl group represented by $R^{21}$;

each $R^{18}$ is independently H or $C_1$-$C_3$ alkyl;

each $R^{18a}$ is independently $C_1$-$C_3$ alkyl;

each $R^{19}$ is H or alkyl or N(R$^{19}$)$_2$ is a nitrogen-containing non-aromatic heterocyclic group;

$R^{20}$ is an optionally substituted piperidinonyl, oxazolidinyl, oxazolidinonyl, thiazolidinyl, tetrahydrofuranyl, tetrahydropyranyl, thiazolidinyl, tetrahydrothiophene, morpholinyl, thiomorpholinyl, imidazolidinyl, imidazolidinonyl, dioxanyl, dioxolanyl, dithiolanyl, pyrrolidinyl, pyrrolidinonyl, piperazinyl, or piperidinyl; and $R^{21}$ is an optionally substituted furanyl, tetrazolyl, oxazolyl, isoxazolyl, oxadiazolyl, pyrrolyl, pyrazolyl, pyridinyl, pyrimidyl, thiazolyl, thienyl, or imidazolyl.

20. The compound of claim 19 wherein the compound is represented by the following structural formula:

or a pharmaceutically acceptable salt thereof, wherein t is 0, 1, 2, 3 or 4.

21. The compound of claim 20 wherein:

$R^Y$ is —C(O)OR$^{18}$, —C(O)N(R$^{19}$)$_2$, optionally N-substituted tetrazolyl or optionally N-substituted imidazolyl; and $R^{18}$ and each $R^{19}$ are independently —H, methyl, or ethyl.

22. The compound of claim 21 wherein $R^8$, $R^{11}$ and $R^{14}$, when present, are independently, halo, CO$_2$R$^{12}$, CONR$^{12}$R$^{13}$, $C_{1-3}$ alkyl, $C_{1-3}$ haloalkyl, hydroxyl, $C_{1-3}$ alkoxy, $C_{1-3}$ haloalkoxy, —CN, amine, $C_{1-3}$ alkyl amine, $C_{1-3}$ dialkylamine.

23. The compound of claim 3 wherein:

$R^1$ is a monocyclic aryl or heteroaryl group, substituted by —V$_3$—R$^{22}$ and wherein the aryl or heteroaryl group represented by $R^1$ optionally is further substituted at any one or more substitutable carbon atoms represented by $R^{11}$;

$V_3$ is a covalent bond, —O—, —C(O)—, —N(R$^{13}$)—, —S—, —S(O)—, —C(O)NR$^{13}$—, —NR$^{13}$C(O)—, —S(O)$_2$NR$^{13}$—, —NR$^{13}$S(O)$_2$—, or —S(O)$_2$—;

each $R^{11}$ is independently halo, —OR$^{12}$, —SR$^{12}$, —CN, —NO$_2$, —N(R$^{12}$R$^{13}$), —N(R$^{13}$)C(O)R$^{12}$, —N(R$^{13}$)CO$_2$R$^{12a}$, —N(R$^{13}$)C(O)N(R$^{12}$R$^{13}$), —C(O)N(R$^{12}$R$^{13}$), —OC(O)R$^{12}$, —OC(O)N(R$^{12}$R$^{13}$), —C(O)R$^{12}$, —CO$_2$R$^{12}$, —SO$_2$R$^{12a}$, —S(O)R$^{12a}$, —SO$_2$N(R$^{12}$R$^{13}$), —N(R$^{13}$)SO$_2$R$^{12a}$, or an optionally substituted group selected from a $C_{1-8}$ aliphatic, a monocyclic aryl, a monocyclic heteroaryl, or a monocyclic non-aromatic group;

each $R^{12}$ is independently hydrogen or an optionally substituted $C_{1-6}$ aliphatic group;

each $R^{12a}$ is an optionally substituted $C_{1-6}$ aliphatic group; and each $R^{13}$ is independently hydrogen, a $C_{1-6}$ aliphatic group, —CO$_2$R$^{12a}$, —SO$_2$R$^{12a}$, or —C(O)R$^{12}$, or —N(R$^{12}$R$^{13}$) is an optionally substituted monocyclic heteroaryl or non-aromatic heterocyclic group; and $R^{22}$ is an optionally substituted monocyclic or bicyclic non-aromatic carbocyclic or an optionally substituted monocyclic or bicyclic non-aromatic heterocyclic group.

24. The compound of claim 23 wherein:

B is a monocyclic aryl or heteroaryl group or a monocyclic cycloalkyl group, each optionally substituted at any one or more substitutable ring carbon atoms with $R^{14}$;

each $R^{14}$ is independently $C_1$-$C_4$ alkyl, $C_1$-$C_4$ haloalkyl, $C_1$-$C_4$ haloalkoxy, R$^{14a}$, R$^{14b}$, -T-R$^{14a}$, -T-R$^{14b}$, —V-T-R$^{14a}$, —V-T$_1$-R$^{14b}$, —V$_1$-T-R$^{14a}$ or —V$_1$-T$_1$-R$^{14b}$;

V is —O—, —N(R)—, —C(O)N(R)— or —S(O)$_2$N(R)—;

$V_1$ is —S(O)$_2$, —C(O)—, —N(R)C(O)— or —N(R)SO$_2$—;

T is a $C_1$-$C_4$ optionally substituted alkylene;

$T_1$ is a $C_2$-$C_4$ optionally substituted alkylene;

each $R^{14a}$ is independently selected from —OR$^{15a}$, —SR$^{15a}$, —C(O)N(R$^{16}$)$_2$, —CO$_2$R$^{15}$, —SO$_2$R$^{15a}$, —S(O)R$^{15a}$, —SO$_2$N(R$^{16}$)$_2$, an optionally substituted monocyclic aryl or heteroaryl group or an optionally substituted monocyclic non-aromatic heterocyclic group;

each $R^{14b}$ is independently selected from halo, —OH, —SH, —CN, —NO$_2$, —N(R$^{16}$)$_2$, —N(R$^{16}$)C(O)R$^{15}$, —N(R$^{16}$)CO$_2$R$^{15a}$, —N(R$^{16}$)C(O)N(R$^{16}$)$_2$, —OC(O)R$^{15}$, —OC(O)N(R$^{16}$)$_2$ or —N(R$^{16}$)SO$_2$R$^{15a}$;

each $R^{15}$ is independently hydrogen or a $C_{1-6}$ aliphatic group;

each $R^{15a}$ is a $C_{1-6}$ aliphatic group; and each $R^{16}$ is independently selected from hydrogen, a $C_{1-6}$ aliphatic group, $-CO_2R^{15a}$, $-SO_2R^{15a}$, or $-C(O)R^{15}$, or $N(R^{16})_2$ is a monocyclic heteroaryl or a monocyclic non-aromatic heterocyclic group.

25. The compound of claim 24 wherein:

$R^2$ is $C_1$-$C_2$ alkyl or $C_3$-$C_6$ cycloalkyl;

$R^3$ is a $C_1$-$C_4$ alkyl group, and $R^4$ is $-(CH_2)_m-B$.

26. The compound of claim 25 wherein $R^{22}$ is an optionally substituted monocyclic non-aromatic heterocyclic group.

27. The compound of claim 26 wherein the compound is represented by the following structural formula:

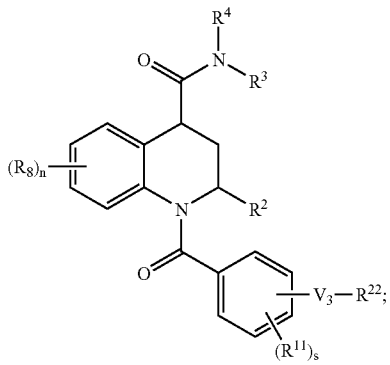

or a pharmaceutically acceptable salt thereof, wherein s is 0, 1, 2, 3, or 4.

28. The compound of claim 27 wherein $-C(O)NR^3R^4$ and $-R^2$ are trans relative to one another.

29. The compound of claim 28 wherein $R^{22}$ is an optionally substituted cyclohexanyl, oxazolidinyl, oxazolidinonyl, thiazolidinyl, tetrahydrofuranyl, tetrahydropyranyl, thiazolidinyl, tetrahydrothienyl, morpholinyl, thiomorpholinyl, imidazolidinyl, imidazolidinonyl, dioxanyl, dioxolanyl, dithiolanyl, pyrrolidinyl, pyrrolidinonyl, piperazinyl, isothiazolidinyl S,S, dioxide, or piperidinyl.

30. The compound of claim 29 wherein the compound is represented by the following structural formula:

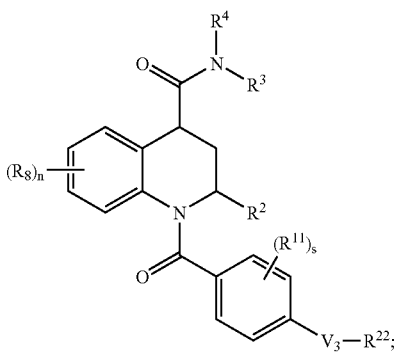

or a pharmaceutically acceptable salt thereof.

31. The compound of claim 30 wherein $V_3$ is absent.

32. The compound of claim 31 wherein $R^{22}$ is oxazolidinyl, thiazolidinyl, tetrahydrofuranyl, morpholinyl, imidazolidinyl, imidazolidinonyl, pyrrolidinyl, pyrrolidinonyl, piperazinyl, or piperidinyl, each optionally substituted at any substitutable carbon atom by alkyl, halide, haloalkyl, hydroxyalkyl, $-C(O)OR^{23}$, $-C(O)R^{23}$, $-OC(O)R^{23}$, or $-C(O)N(R^{23})_2$, and each optionally substituted at any substitutable nitrogen atom with alkyl, haloalkyl, hydroxyalkyl, $-C(O)OR^{23}$, $-C(O)R^{23}$, $-(CH_2)_qCO_2H$, $-(CH_2)_qC(O)N(R^{23})_2$, $-(CH_2)_qCH(CH_3)CON(R^{23})_2$; $-(CH_2)_qC(CH_3)_2CON(R^{23})_2$; $-(CH_2)_qC(CH_3)_2CO_2R^{23}$ or $-(CH_2)_qCH(CH_3)CO_2R^{23}$;

q is an integer from 1-4; and each $R^{23}$ is independently $-H$, alkyl, haloalkyl, or hydroxyalkyl.

33. The compound of claim 32 wherein the compound is represented by the following structural formula:

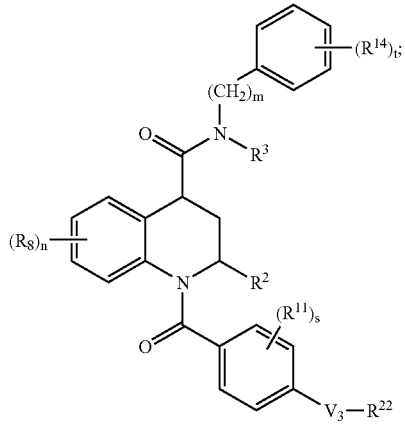

or a pharmaceutically acceptable salt thereof, wherein t is 0, 1, 2, 3 or 4.

34. The compound of claim 33 wherein $R^8$, $R^{11}$ and $R^{14}$, when present, are independently, halo, $C_{1-3}$ alkyl, $C_{1-3}$ haloalkyl, hydroxyl, $C_{1-3}$ alkoxy, $C_{1-3}$ haloalkoxy, $-CN$, amine, $C_{1-3}$ alkyl amine, $C_{1-3}$ dialkylamine.

35. A pharmaceutical composition comprising a pharmaceutically acceptable carrier or diluent and an effective amount of a compound represented by the compound of claim 1.

36. A method of treating an inflammatory disease in a subject, comprising the step of administering to the subject an effective amount of a compound represented by the compound of claim 1.

37. The method of claim 36, where the inflammatory disease is atopic dermatitis, allergic rhinitis, rheumatoid arthritis, multiple sclerosis, chronic obstructive pulmonary disorder (COPD), COPD exacerbations, or allergic asthma.

38. The method of claim 37, where the inflammatory disease, disorder or symptom is atopic dermatitis, chronic obstructive pulmonary disorder (COPD), COPD exacerbations, allergic rhinitis, or allergic asthma.

39. A method of inhibiting CRTH2 activity in: (a) a subject; or (b) a biological sample; which method comprises administering to said subject, or contacting said biological sample with a compound represented by claim 1.

* * * * *

UNITED STATES PATENT AND TRADEMARK OFFICE
CERTIFICATE OF CORRECTION

PATENT NO. : 7,951,950 B2
APPLICATION NO. : 11/360885
DATED : May 31, 2011
INVENTOR(S) : Jeremy D. Little et al.

Page 1 of 1

It is certified that error appears in the above-identified patent and that said Letters Patent is hereby corrected as shown below:

In Column 136, Claim 7, Line 41, delete, "pylori" and replace with -- pyrollyl --

Signed and Sealed this
Twelfth Day of March, 2013

Teresa Stanek Rea
*Acting Director of the United States Patent and Trademark Office*